(12) United States Patent
Hutchinson et al.

(10) Patent No.: US 8,785,393 B2
(45) Date of Patent: Jul. 22, 2014

(54) OPHTHALMIC PHARMACEUTICAL COMPOSITIONS OF DP2 RECEPTOR ANTAGONISTS

(75) Inventors: John Howard Hutchinson, San Diego, CA (US); Thomas Jon Seiders, San Diego, CA (US); Nicholas Simon Stock, San Diego, CA (US)

(73) Assignee: Panmira Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 13/387,064

(22) PCT Filed: Jul. 28, 2010

(86) PCT No.: PCT/US2010/043598
§ 371 (c)(1),
(2), (4) Date: Apr. 2, 2012

(87) PCT Pub. No.: WO2011/014587
PCT Pub. Date: Feb. 3, 2011

(65) Prior Publication Data
US 2012/0184496 A1      Jul. 19, 2012

Related U.S. Application Data

(60) Provisional application No. 61/230,565, filed on Jul. 31, 2009.

(51) Int. Cl.
*A61K 38/13* (2006.01)

(52) U.S. Cl.
USPC ........................................................ 514/20.5

(58) Field of Classification Search
None
See application file for complete search history.

(56) References Cited

U.S. PATENT DOCUMENTS

| | | | |
|---|---|---|---|
| 5,827,868 A | 10/1998 | Misra et al. | |
| 6,710,080 B2 | 3/2004 | Sundermann et al. | |
| 6,884,593 B1 | 4/2005 | Hirai et al. | |
| 7,144,913 B2 | 12/2006 | Wang et al. | |
| 7,205,329 B2 | 4/2007 | Chien et al. | |
| 7,321,001 B2 | 1/2008 | Fu et al. | |
| 7,687,664 B2 | 3/2010 | Matsuura et al. | |
| 8,067,445 B2 | 11/2011 | Hutchinson et al. | |
| 8,071,807 B2 | 12/2011 | Hutchinson et al. | |
| 8,168,678 B2 | 5/2012 | Hutchinson et al. | |
| 8,247,602 B2 | 8/2012 | Hutchinson et al. | |
| 8,338,484 B2 | 12/2012 | Hutchinson et al. | |
| 8,362,044 B2 | 1/2013 | Hutchinson et al. | |
| 2001/0047027 A1 | 11/2001 | Labelle et al. | |
| 2002/0198251 A1 | 12/2002 | Sundermann et al. | |
| 2004/0162323 A1 | 8/2004 | Krauss et al. | |
| 2004/0214888 A1 | 10/2004 | Matsura et al. | |
| 2004/0220237 A1 | 11/2004 | Fu et al. | |
| 2005/0154044 A1 | 7/2005 | Beaulieu et al. | |
| 2005/0171143 A1 | 8/2005 | Tanimoto et al. | |
| 2005/0272756 A1 | 12/2005 | Leblanc et al. | |
| 2006/0100425 A1 | 5/2006 | Bennani et al. | |
| 2006/0106081 A1 | 5/2006 | Bennani et al. | |
| 2008/0085891 A1 | 4/2008 | Fu et al. | |
| 2008/0306109 A1 | 12/2008 | Hynd et al. | |
| 2009/0186923 A1* | 7/2009 | Armer et al. .................. | 514/339 |
| 2009/0197959 A1 | 8/2009 | Hutchinson et al. | |
| 2010/0004331 A1 | 1/2010 | Hutchinson et al. | |
| 2010/0081673 A1 | 4/2010 | Hutchinson et al. | |
| 2010/0113503 A1 | 5/2010 | Hutchinson et al. | |
| 2010/0173313 A1 | 7/2010 | Bain et al. | |
| 2010/0280049 A1 | 11/2010 | Stearns et al. | |
| 2010/0298368 A1 | 11/2010 | Stearns et al. | |
| 2011/0021573 A1 | 1/2011 | Hutchinson et al. | |
| 2011/0034558 A1 | 2/2011 | Brittain et al. | |
| 2011/0039852 A1 | 2/2011 | Hutchinson et al. | |
| 2011/0098352 A1 | 4/2011 | Hutchinson et al. | |
| 2011/0144160 A1 | 6/2011 | Hutchinson et al. | |
| 2011/0245303 A1 | 10/2011 | Hutchinson et al. | |
| 2012/0059055 A1 | 3/2012 | Hutchinson et al. | |
| 2013/0053444 A1 | 2/2013 | Brittain et al. | |

FOREIGN PATENT DOCUMENTS

| | | |
|---|---|---|
| EP | 1170594 A2 | 1/2002 |
| GB | 2460597 B | 4/2010 |
| GB | 2461629 B | 5/2010 |
| GB | 2463788 B | 12/2010 |
| JP | 2004-182657 A | 7/2004 |
| WO | WO-99-11605 A1 | 3/1999 |
| WO | WO-2004-035543 A1 | 4/2004 |
| WO | WO-2004-058164 A2 | 7/2004 |
| WO | WO-2004-094372 | 11/2004 |
| WO | WO-2004-096777 A1 | 11/2004 |
| WO | WO-2005-040114 A1 | 5/2005 |
| WO | WO-2005-044260 A1 | 5/2005 |

(Continued)

OTHER PUBLICATIONS

Arima, M., and Fukuda, T., "Prostaglandin $D_2$ receptors DP and CRTH2 in the pathogenesis of asthma," Curr. Mol. Med. 8, 365-375 (2008).

Brannan et al., "Inhibition of Mast Cell PGD2 Release Protects Against Mannitol-Induced Airway Narrowing," Eur Respir J, 2006, vol. 27, No. 5, pp. 944-950, ERS Journals Ltd.

Cossette et al., "Agonist and Antagonist Effects of 15R-Prostaglandin (PG) $D_2$ and 11-Methylene-PGD$_2$ on Human Eosinophils and Basophils," Journal of Pharmacology and Experimental Therapeutics, 2007, pp. 173-179, vol. 320, No. 1, American Society for Pharmacology and Experimental Therapeutics, USA.

(Continued)

*Primary Examiner* — Marcela M Cordero Garcia
*Assistant Examiner* — Kaipeen Yang
(74) *Attorney, Agent, or Firm* — Wilson Sonsini Goodrich & Rosati

(57) ABSTRACT

Described herein are ophthalmic pharmaceutical compositions, wherein the ophthalmic pharmaceutical compositions are in a form suitable for administration to an eye of a mammal. Ophthalmic pharmaceutical compositions disclosed herein include at least one DP$_2$ receptor antagonist compound and are used to treat or prevent ophthalmic diseases or conditions.

22 Claims, 5 Drawing Sheets

(56) References Cited

FOREIGN PATENT DOCUMENTS

| WO | WO-2005-105727 A1 | 10/2005 |
|---|---|---|
| WO | WO-2006-005909 A1 | 1/2006 |
| WO | WO-2006-018325 A1 | 2/2006 |
| WO | WO-2006-037982 A2 | 4/2006 |
| WO | WO-2006-052798 A2 | 5/2006 |
| WO | WO 2006-066968 | 6/2006 |
| WO | WO-2006-070325 A2 | 7/2006 |
| WO | WO-2006-125596 A1 | 11/2006 |
| WO | WO-2007-037187 A1 | 4/2007 |
| WO | WO-2007-039736 A1 | 4/2007 |
| WO | WO-2007-047378 A2 | 4/2007 |
| WO | WO-2007-068894 A2 | 6/2007 |
| WO | WO-2007-107772 A1 | 9/2007 |
| WO | WO-2007-144127 A1 | 12/2007 |
| WO | WO-2008-017989 A1 | 2/2008 |
| WO | WO-2008-024746 A1 | 2/2008 |
| WO | WO-2008-137027 A2 | 11/2008 |
| WO | WO-2008-156780 A1 | 12/2008 |
| WO | WO-2009-004379 A1 | 1/2009 |
| WO | WO-2009-044147 A1 | 4/2009 |
| WO | WO-2009-063202 A2 | 5/2009 |
| WO | WO-2009-063215 A2 | 5/2009 |
| WO | WO-2009-089192 A1 | 7/2009 |
| WO | WO-2009-099901 A1 | 8/2009 |
| WO | WO-2009-099902 A1 | 8/2009 |
| WO | WO-2009-102893 A2 | 8/2009 |
| WO | WO-2009-108720 A2 | 9/2009 |
| WO | WO 2009108720 A2 * | 9/2009 |
| WO | WO-2009-145989 A2 | 12/2009 |
| WO | WO-2010-003120 A2 | 1/2010 |
| WO | WO-2010-003127 A2 | 1/2010 |
| WO | WO 2010003127 A2 * | 1/2010 |
| WO | WO-2010-037054 A2 | 4/2010 |
| WO | WO-2010-037059 A2 | 4/2010 |
| WO | WO-2010-039977 A2 | 4/2010 |
| WO | WO-2010-042652 A2 | 4/2010 |
| WO | WO-2010-057118 A2 | 5/2010 |
| WO | WO-2011-014587 A2 | 2/2011 |
| WO | WO-2011-014588 A2 | 2/2011 |
| WO | WO-2011-017201 A2 | 2/2011 |

OTHER PUBLICATIONS

Crosignani et al., "Discovery of a new class of potent, selective, and orally bioavailable CRTH2(DP2) receptor antagonists for the treatment of allergic inflammatory diseases" J Med Chem 51:2227-2243 (2008).
Evans et al., "Seeing the future of bioactive lipid drug targets," Nature Chem Biol 6:476-479 (2010).
Hata, A.N. and Breyer, R.M., "Pharmacology and signaling of prostaglandin receptors: multiple roles in inflammation and immune modulation," Pharmacal Ther. Aug.;103(2):147-66 (2004).
Jatakanon et al., "Neutrophilic Inflammation in Severe Persistent Asthma," Am J Respir Crit Care Med 1999, pp. 1532-1539, vol. 160, National Heart and Lung Institute, London, UK.
Johnston et al., "Prostaglandin $D_2$-Induced Bronchoconstriction Ts Mediated Only in Part by the Thromboxane Prostanoid Receptor," Eur Respir J, 1995, 8, pp. 411-415, ERS Journals Ltd, UK.
Kim et al., "Regulation of Immune Cells by Eicosanoid Receptors," The Scientific World Journal 7:1307-1328 (2007).
Kostenis, E. and Ulven, T., "Emerging roles of DP and CRTH2 in allergic inflammation," Trends Mol Med. Apr.;12(4):148-58 (2008).
Ly and Bacon, "Small-molecule CRTH2 antagonists for the treatment of allergic inflammation: an overview," Exp Opin Invest Drugs 14:769 (2005).
Medina, J. C. and Liu, J., "PGD2 Antagonists" Annual Reports in Medicinal Chemistry, vol. 41, 2006, pp. 221-235.
PCT/US10/43599 Search Report and Written Opinion mailed Apr. 28, 2011.
Pettipher et al., "Antagonism of the prostaglandin D2 receptors DPl and CRTH2 as an approach to treat allergic diseases," Nature Reviews/Drug Discovery 6:313-325 (2007).
Pettipher et al., "Antagonists of the prostaglandin D2 receptor CRTH2," Drug News Perspect 21:317-322 (2008).
Pettipher et al., "The roles of the prostaglandin D(2) receptors DP(I) and CRTH2 in promoting allergic responses," Br J Pharmacol 153:S191 (2008).
Sagel et al., "Sputum Biomarkers of Inflammation in Cystic Fibrosis Lung Disease," Proc Am Thorac Soc, 2007, vol. 4, pp. 406-417, www.atsjournals.org.
Sandham et al., "7-Azaindole-3-acetic acid derivatives: potent and selective CRTH2 receptor antagonists," Bioorg Med Chem Lett 19:4794-4798 (2009).
Sandig et al., "Contrary prostaglandins: the opposing roles of PGD2 and its metabolites in leukocyte function," J Leukocyte Biology 81:372-382 (2007).
Scott et al., "Discovery and optimization of a biphenylacetic acid series of prostaglandin D2 receptor DP2 antagonists with efficacy in a murine model of allergic rhinitis," Bioorg Med Chem Ltrs (2011), doi: 10.1016fj.bmcl.2011.01.024.
Stearns et al., "Novel tricyclic antagonists of the prostaglandin D2 receptor DP2 with efficacy in a murine model of allergic rhinitis," Bioorg Med Chem Ltrs 19:4647-4651 (2009).
Stebbins et al., "DP2 Receptor Antagonists: Novel Therapeutic Target for COPD," Mol Cell Pharmacol 2(3):89-96 (2010).
Stebbins et al., "Pharmacological Blockade of the DP2 Receptor Inhibits Cigarette Smoke-Induced Inflammation, Mucus Cell Metaplasia, and Epithelial Hyperplasia in the Mouse Lung," J Pharmacol Exp Ther 332(3):764-775 (2010).
Stebbins et al., "Therapeutic efficacy of AM156, a novel prostanoid DP2 receptor antagonist, in murine models of allergic rhinitis and house dust mite-induced pulmonary inflammation," Eur J Pharmacol 638:142-149 (2010).
Stock et al., "Sodium [2'-[(cyclopropanecarbonyl-ethyl-amino)-methyl]-4'-(6- ethoxy-pyridin-3-yl)-6-methoxy-biphenyl-3-yl]-acetate (AM432): A potent, selective prostaglandin D2 receptor antagonist," Bioorg Med Chem Ltrs 21:1036-1040 (2011).
Sugimoto et al., "An Orally Bioavailable Small Molecule Antagonist of CRTH2, Ramatroban (BAY u3405), Inhibits Prostaglandin $D_2$-Induced Eosinophil Migration in Vitro," Journal of Pharmacology and Experimental Therapeutics, 2003, pp. 347-352, vol. 305, No. 1, American Society for Pharmacology and Experimental Therapeutics, USA.
Takeshita et al., "CRTH2 is a prominent effector in contact hypersensitivity-induced neutrophil inflammation," Intl Immunol 16(7):947-959 (2004).
Tirouvanziam, R., et al., "Profound functional and signaling changes in viable inflammatory neutrophils homing to cystic fibrosis airways," Proc. Nat. Acad. Sci. USA 105:4335-4339 (2008).
Torisu et al. "Discovery of new chemical leads for prostaglandin $D_2$ receptor antagonists." Bioorganic & Medicinal Chemistry Letters, 2004, 14:4557-4562.
Ulven et al., "Minor Structural Modifications Cover the Dual TP/CRTH2," J Med Chem 48(4):897-900 (2005).
Ulven et al,. "Targeting the prostaglandin D2 receptors DP and CRTH2 for treatment of inflammation", Curr. Top. Med. Chem. 2006;6(13):1427-44.
Wardlaw et al., "New Insights into the Relationship Between Airway Inflammation and Asthma," Clinical Science, 2002, pp. 201-211, vol. 103, The Biochemical Society and the Medical Research Society, GB.
EP10805004 Supplementary European Search Report mailed May 17, 2013.
Bain, et al. "Pharmacodynamics, pharmacokinetics, and safety of AM211: a novel and potent antagonist of the prostaglandin D2 receptor type 2." J Clin Pharmacol. Oct. 2012;52(10):1482-93.
Bain, et al. "Pharmacology of AM211, a potent and selective prostaglandin D2 receptor type 2 antagonist that is active in animal models of allergic inflammation." J Pharmacol Exp Ther. Jul. 2011;338(1):290-301.
Stebbins, et al. "DP2 (CRTh2) antagonism reduces ocular inflammation induced by allergen challenge and respiratory syncytial virus." Int Arch Allergy Immunol. 2012;157(3):259-68.

* cited by examiner

* P<0.05 vs. smoke, one-tailed t-test

US 8,785,393 B2

OPHTHALMIC PHARMACEUTICAL COMPOSITIONS OF DP2 RECEPTOR ANTAGONISTS

RELATED APPLICATIONS

This application is filed pursuant to 35 U.S.C. §371 as a United States National Phase Application of International Application No. PCT/US2010/043598, entitled "OPHTHALMIC PHARMACEUTICAL COMPOSITIONS OF $DP_2$ RECEPTOR ANTAGONISTS" filed Jul. 28, 2010, which claims the benefit of U.S Provisional Patent Application No. 61/230,565 entitled "OPHTHALMIC PHARMACEUTICAL COMPOSITIONS OF $DP_2$ RECEPTOR ANTAGONISTS" filed on Jul. 31, 2009, all of which are incorporated by reference in their entirety.

FIELD OF THE INVENTION

Described herein are ophthalmic pharmaceutical compositions that include at least one $DP_2$ receptor antagonist compound and methods of use thereof in the treatment or prevention of ophthalmic diseases, disorders or conditions.

BACKGROUND OF THE INVENTION

Prostaglandins have a diverse range of activities and have a well recognized role in inflammation. Prostaglandin $D_2$ ($PGD_2$) is produced by mast cells, macrophages and Th2 lymphocytes in response to local tissue damage and/or inflammation and/or infection related to ocular diseases or conditions. $PGD_2$ binds to a number of receptors, which include the thromboxane-type prostanoid (TP) receptor, $PGD_2$ receptor (DP, also known as $DP_1$) and chemoattractant receptor-homologous molecule expressed on Th2 cells (CRTH2; also known as $DP_2$). In Th2 lymphocytes, IL-4, IL-5 and IL-13 cytokine production is stimulated. These cytokines have been implicated in numerous biological actions including, by way of example only, mucous secretion, inflammation and/or eosinophil recruitment. Ophthalmic pharmaceutical compositions comprising $DP_2$ receptor antagonists, administered to any ocular tissue of a mammal, are used to treat or prevent $DP_2$-dependent or $DP_2$-mediated diseases or conditions.

SUMMARY OF THE INVENTION

Described herein are ophthalmic pharmaceutical compositions comprising at least one $DP_2$ receptor antagonist. The ophthalmic pharmaceutical compositions comprising at least one $DP_2$ receptor antagonist are in a form that is for administration to an eye of a mammal. The ophthalmic pharmaceutical compositions are used in the treatment or prevention of ophthalmic diseases or conditions. In some embodiments, the ophthalmic disease or condition is an abnormal state of an eye and/or a related tissue. In some embodiments, the ophthalmic disease or condition is an inflammatory ophthalmic disease or condition. In some embodiments, the ophthalmic disease or condition is due to an allergic reaction or an infection of the eye. In some embodiments, the ophthalmic pharmaceutical composition is administered to the eye of a mammal to treat or prevent an immune disorder of the eye (e.g. an autoimmune disorder); a proliferative disorder of the eye (e.g., intraocular melanoma); contact of the eye with an allergen, and/or an irritant; a mast cell mediated ophthalmic diseases or condition (e.g., over-production of prostaglandin $D_2$); Th2-mediated ophthalmic disease or condition; or combinations thereof.

In some embodiments, the ophthalmic pharmaceutical compositions described herein are administered to the eye of a mammal to treat age-related macular degeneration, allergic conjunctivitis, eosinophilic keratitis, anterior segment scarring, blepharitis, blepharoconjunctivitis, a bullous disorder, cicatricial pemphigoid, conjunctival melanoma, conjunctivitis, contact lens-associated giant papillary conjunctivitis, diabetic retinopathy, dry eye, episcleritis, glaucoma, gliosis, granuloma annulare, Graves' ophthalmopathy, intraocular melanoma, keratitis, keratoconjunctivitis, pain, pinguecula, post-surgical pain, proliferative vitreoretinopathy, pterygia, scarring, scleritis, Sjögren's syndrome, uveitis, vernal keratoconjunctivitis or combinations thereof.

In some embodiments, the ophthalmic pharmaceutical compositions described herein are administered to the eye of the mammal before or after contact with an allergen and/or irritant and/or an infectious agent (e.g., a virus). In some embodiments, the ophthalmic pharmaceutical compositions described herein are administered to the eye of a mammal before or after a physical trauma (e.g., surgery). In some embodiments, the ophthalmic pharmaceutical compositions described herein are administered to the eye of a mammal to treat conditions associated with the outer surface of the eye. In other embodiments, the ophthalmic pharmaceutical compositions described herein are administered to the outer surface of the eye of a mammal but subsequently penetrate into the eye to treat a disease or condition associated with the interior of the eye. In other embodiments, the ophthalmic pharmaceutical compositions described herein are administered to the eye of a mammal in order to treat tissues in contact with or near the eye; non-limiting examples include the tear duct, the eye lid, the eye lash, and/or the eye socket.

Provided, in some embodiments, is an ophthalmic pharmaceutical composition comprising a $DP_2$ receptor antagonist compound in an amount effective for the treatment of a $DP_2$-dependent or $DP_2$-mediated disease or condition (e.g., a prostaglandin $D_2$-dependent or prostaglandin $D_2$-mediated disease or condition), and at least one pharmaceutically acceptable excipient to provide a solution, suspension, drops, emulsion, ointment, gel or an insert, wherein the ophthalmic pharmaceutical composition is in a form for administration to the eyes of a mammal.

Provided, in some embodiments, is an ophthalmic pharmaceutical composition comprising a $DP_2$ receptor antagonist compound in an amount effective for antagonizing $DP_2$ receptors in the eye of a mammal, and at least one pharmaceutically acceptable excipient to provide a solution, suspension, drops, emulsion, ointment, gel or an insert, wherein the formulation is in a form for administration to the eyes of a mammal.

In some embodiments, the $DP_2$ receptor antagonist is a compound of Formula (I), Formula (II), Formula (III), or Formula (IV), or a pharmaceutically acceptable salt, pharmaceutically acceptable solvate, metabolite, or prodrug thereof. In some embodiments, the $DP_2$ receptor antagonist is a compound of Formula (I), or a pharmaceutically acceptable salt, pharmaceutically acceptable solvate, metabolite, or prodrug thereof. In some embodiments, the $DP_2$ receptor antagonist is a $DP_2$ receptor antagonist disclosed herein.

In some embodiments, an ophthalmic pharmaceutical composition described herein further comprises a second therapeutic agent in addition to the $DP_2$ receptor antagonist. In some embodiments, the second therapeutic agent is an antibiotic, an anti-fungal agent, a steroid anti-inflammatory agent, a non-steroidal anti-inflammatory agent, an antiviral agent, an alpha agonist, a beta blocker, a carbonic anhydrase inhibitor, a prostaglandin, an anti-angiogenesis agent, loteprednol etabonate, a mast cell stabilizer, cyclosporine, a $cysLT_1R$ antagonist, a 5-LO inhibitor, a $BLT_1R$ antagonist, an $LTA_4$ hydrolase inhibitor or a FLAP inhibitor compound.

Provided herein is a method of treating a $DP_2$-dependent or $DP_2$-mediated disease or condition, comprising administering to an eye of an individual in need thereof an ophthalmic pharmaceutical composition comprising a therapeutically-effective amount of a $DP_2$ receptor antagonist compound.

In some embodiments, the ophthalmic pharmaceutical composition is in the form of a solution, suspension, drops, emulsion, ointment, gel or an insert. In some embodiments, the ophthalmic pharmaceutical composition is administered via implantation, insertion, injection, spraying, washing, or combinations thereof.

In some embodiments, the ophthalmic pharmaceutical composition is administered before contact with an irritant and/or allergen and/or an infectious agent. In some embodiments, the ophthalmic pharmaceutical composition is administered after contact with an irritant and/or allergen and/or an infectious agent.

In some embodiments, the ophthalmic pharmaceutical composition is administered to the eyes of a mammal to reduce or eliminate itching of the eyes (i.e. ocular itching). In some embodiments, ocular itching is results from contact with an irritant and/or allergen and/or an infectious agent. In some embodiments, ocular itching is a symptom of any of the diseases or conditions described herein. In some embodiments, ocular itching is a symptom of conjunctivitis. In some embodiments, ocular itching is a symptom of allergic conjunctivitis.

In some embodiments, described is a method of treating or preventing ocular itching in a mammal comprising administering to the mammal an ophthalmic pharmaceutical composition described herein. In some embodiments, the ocular itching is a symptom of allergies. In some embodiments, the ocular itching is caused by contact with an irritant, an allergen, an infectious agent or combinations thereof. In some embodiments, the ocular itching is a symptom of allergic conjunctivitis.

In some embodiments, described is a method of treating or preventing ocular inflammation in a mammal comprising administering to the mammal an ophthalmic pharmaceutical composition described herein. In some embodiments, the ocular inflammation is a symptom of allergies. In some embodiments, the ocular inflammation is caused by contact with an irritant, an allergen, an infectious agent or combinations thereof. In some embodiments, the ocular inflammation is a symptom of allergic conjunctivitis.

In some embodiments, described is a method of treating or preventing redness, irritation, swelling, lachrymal secretions, or a combination thereof in the eye of a mammal comprising administering to the mammal an ophthalmic pharmaceutical composition described herein. In some embodiments, the redness, irritation, swelling, lachrymal secretions, or a combination thereof is a symptom of allergies. In some embodiments, the redness, irritation, swelling, lachrymal secretions, or a combination thereof is caused by contact with an irritant, an allergen, an infectious agent or combinations thereof. In some embodiments, the redness, irritation, swelling, lachrymal secretions, or a combination thereof is a symptom of allergic conjunctivitis.

In some embodiments, the ophthalmic pharmaceutical composition comprises an excipient selected from a pH adjusting component, cosolvent, emulsifier, penetration enhancer, preservative system, and emollient, or combination thereof. In some embodiments, the ophthalmic pharmaceutical composition further comprises a tonicity adjusting component.

In some embodiments, the tonicity adjusting component is sodium borate, boric acid, sodium chloride, potassium chloride, mannitol, dextrose, glycerin, propylene glycol or mixtures thereof.

In some embodiments, the ophthalmic pharmaceutical composition is administered as an eye drop. In some embodiments, the ophthalmic pharmaceutical composition is administered as an eye ointment.

In some embodiments, the concentration of the $DP_2$ receptor antagonist in the ophthalmic pharmaceutical composition is about 0.1 to about 10% by weight of the ophthalmic pharmaceutical composition. In some embodiments, the concentration of the $DP_2$ receptor antagonist in the ophthalmic pharmaceutical composition is about 0.25 to about 5% by weight of the ophthalmic pharmaceutical composition.

Provided herein is a method of increasing the concentration of a $DP_2$ receptor antagonist in the eyes of a mammal comprising administering to a mammal in need thereof a therapeutically effective amount of an ophthalmic pharmaceutical composition described herein. In some embodiments, the mammal has at least one symptom of a prostaglandin $D_2$-dependent or prostaglandin $D_2$-mediated disease or condition affecting the eyes.

In one aspect is the use of a $DP_2$ receptor antagonist compound in the manufacture of an ophthalmic pharmaceutical composition. In one aspect is the use of a combination of a $DP_2$ receptor antagonist compound and a second therapeutic agent (e.g. a FLAP inhibitor compound) in the manufacture of an ophthalmic pharmaceutical composition.

In one aspect is the use of $DP_2$ receptor antagonist compound in the manufacture of an ophthalmic pharmaceutical composition for the treatment of an ophthalmic disease or condition. In one aspect is the use of a $DP_2$ receptor antagonist compound and a second therapeutic agent (e.g., a FLAP inhibitor compound) in the manufacture of an ophthalmic pharmaceutical composition for the treatment of an ophthalmic disease or condition.

In one aspect, $DP_2$ receptors are involved in the pathogenesis of ophthalmic diseases, disorders or conditions. In some embodiments, ophthalmic diseases, disorders or conditions are treated or prevented in a mammal comprising administering to the eyes of the mammal an ophthalmic pharmaceutical composition that includes a $DP_2$ receptor antagonist compound.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

Figure 1:
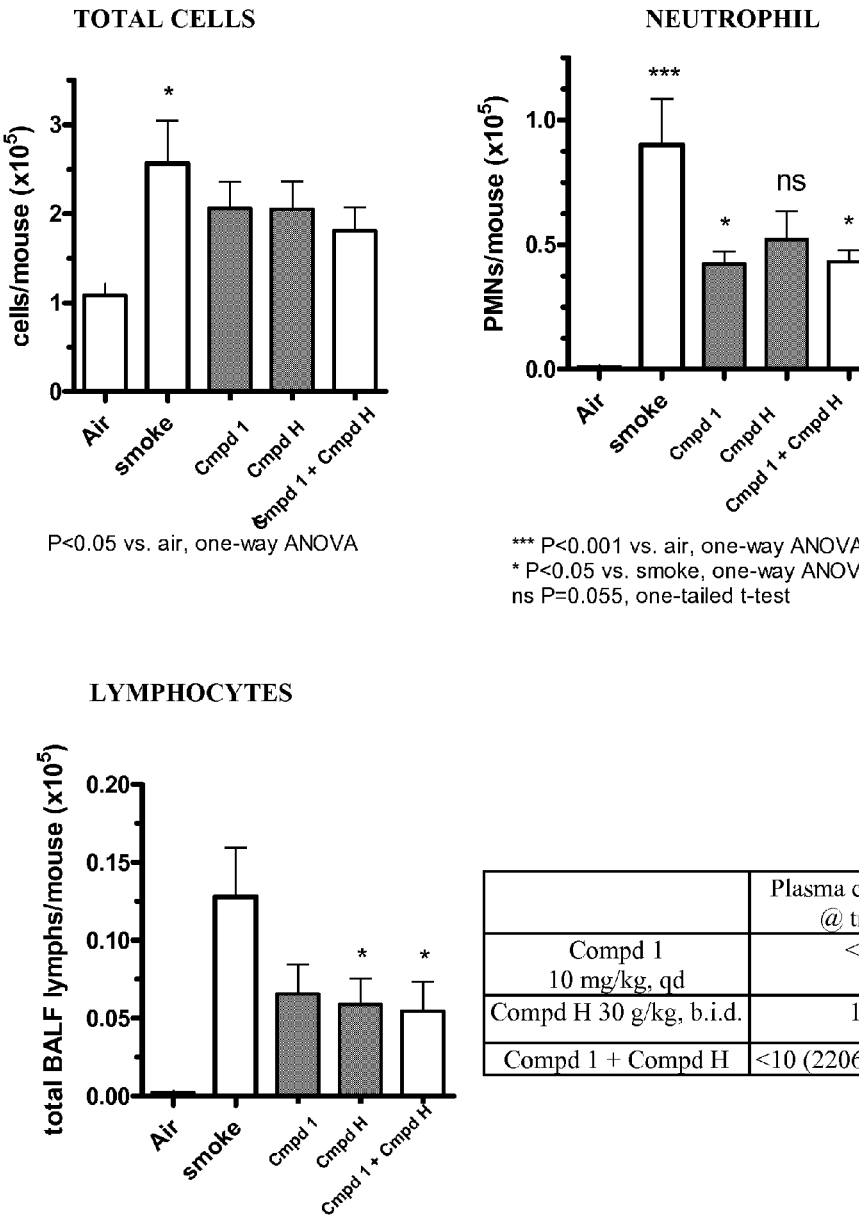
FIG. 1 illustrates the effect of $DP_2$ receptor antagonism, alone or in combination with FLAP inhibition, on the number of total cells, neutrophils and lymphocytes present in BALF in a mouse subchronic smoke model.

Prostaglandin $D_2$ ($PGD_2$) is an acidic lipid derived from the metabolism of arachidonic acid by cyclooxygenases and $PGD_2$ synthases. $PGD_2$ is produced by mast cells, macrophages and Th2 lymphocytes in response to local tissue damage as well as in response allergic inflammation and/or infection. $PGD_2$ exerts a variety of biologic actions in the eye; these include ocular hypotension and inflammatory effects on the conjunctiva.

Activation of $DP_2$ is associated with chemotaxis and activation of Th2 lymphocytes, eosinophils and basophils. $PGD_2$ binds to $DP_2$ receptors and mediates many of its effects through a $G_i$-dependent elevation of intracellular calcium levels and reduction of cyclic AMP. In Th2 lymphocytes, IL-4, IL-5 and IL-13 cytokine production are also stimulated by $DP_2$ receptor activation. These cytokines have been implicated in numerous biological actions including, by way of example only, immunoglobulin E production, mucous secretion, and eosinophil recruitment.

Chronic allergic eye diseases, such as vernal keratoconjunctivitis and atopic keratoconjunctivitis, have sight-threatening sequelae. T cells, eosinophils, and mast cells are all found in the conjunctiva, and are thought to play a role in disease pathogenesis.

$DP_2$ receptors provide a target for the treatment of $PGD_2$-dependent or $PGD_2$-mediated ophthalmic diseases, disorders or conditions, including, by way of example, age-related macular degeneration, allergic conjunctivitis, eosinophilic keratitis, anterior segment scarring, blepharitis, blepharoconjunctivitis, a bullous disorder, cicatricial pemphigoid, conjunctival melanoma, conjunctivitis, contact lens-associated giant papillary conjunctivitis, diabetic retinopathy, dry eye, episcleritis, glaucoma, gliosis, granuloma annulare, Graves' ophthalmopathy, intraocular melanoma, keratitis, keratoconjunctivitis, pain, pinguecula, post-surgical pain, proliferative vitreoretinopathy, pterygia, scarring, scleritis, Sjögren's syndrome, uveitis, atopic keratoconjunctivitis, or vernal keratoconjunctivitis.

Disclosed herein is the use of $DP_2$ receptor antagonist compounds in the manufacture of medicaments for administration to an eye of a mammal for the treatment or prevention of a $DP_2$-dependent or $DP_2$-mediated diseases or conditions (e.g., prostaglandin $D_2$-dependent or prostaglandin $D_2$-mediated ophthalmic diseases or conditions).

Described herein, in certain embodiments, are ophthalmic pharmaceutical compositions that include a $DP_2$ receptor antagonist compound, wherein the ophthalmic pharmaceutical compositions are administered to the eye of a mammal to treat or prevent an ophthalmic disease or condition. In one aspect, administration of the ophthalmic pharmaceutical compositions to the eye minimizes systemic absorption of the $DP_2$ receptor antagonist compound. In one aspect, ophthalmic administration of a $DP_2$ receptor antagonist compound provides for local treatment of an ophthalmic disease or condition. In one aspect, local treatment of an ophthalmic disease or condition with a $DP_2$ receptor antagonist compound reduces possible side effects associated with systemic administration of a $DP_2$ receptor antagonist compound.

In one aspect, the ophthalmic disease or condition is a result of the activation of $DP_2$ receptors by prostaglandin $D_2$. In one aspect, the ophthalmic disease or condition includes, but is not limited to, ophthalmic immune disorders, ophthalmic proliferative disorders, an ophthalmic disease or condition resulting from contact with an allergen and/or an irritant, an ophthalmic mast cell disorder, an infection or combinations thereof.

Ophthalmic immune disorders include, but are not limited to, age-related macular degeneration, allergic conjunctivitis, eosinophilic keratitis, anterior segment scarring, blepharitis, blepharoconjunctivitis, a bullous disorder, cicatricial pemphigoid, conjunctival melanoma, conjunctivitis, contact lens-associated giant papillary conjunctivitis, diabetic retinopathy, dry eye, episcleritis, glaucoma, gliosis, granuloma annulare, Graves' ophthalmopathy, intraocular melanoma, keratitis, keratoconjunctivitis, pain, pinguecula, post-surgical pain, proliferative vitreoretinopathy, pterygia, scarring, scleritis, Sjögren's syndrome, uveitis, vernal keratoconjunctivitis or combinations thereof.

Ophthalmic proliferative disorders include but are not limited to, intraocular melanoma and conjunctival melanoma. Ophthalmic infections include infections caused by bacteria (e.g., *Staphylococcus aureus*), viruses (e.g., Respiratory Syntactic Virus (RSV), chlamydia) or the like.

In certain instances, prostaglandin $D_2$ is involved in inflammation and/or recruitment of eosinophils. In one aspect, antagonism of $DP_2$ receptors inhibits the activity of and/or migration of eosinophils, and/or treats inflammation in the eye.

In one aspect, prostaglandin $D_2$ and/or cytokines are involved in the pathogenesis of ophthalmic diseases or conditions described herein. In some instances, antagonism of $DP_2$ receptors results in a decrease in secretion of cytokines (e.g., from Th2 lymphocytes). In some instances, antagonism of $DP_2$ receptors inhibits or decreases the symptoms associated with such ophthalmic diseases or conditions.

In one aspect, prostaglandin $D_2$ and/or cytokines (e.g., Interleukin 4 (IL-4) and the like) are involved in the pathogenesis of ophthalmic diseases or conditions described herein. In some instances, prostaglandin $D_2$ and/or cytokines cause accumulation of mucin in ocular tissues. In some instances, antagonism of $DP_2$ receptors in the eye results in a decrease in the production of IL-4. A reduction of IL-4 results in a decrease of the symptoms associated with such ophthalmic diseases or conditions. In some instances, a reduction of cytokine production reduces or inhibits the accumulation of mucin in ocular tissues.

In some instances, inflammation in the eye causes production of lachrymal secretions (e.g., mucus, mucin, pus or the like) that are associated with pathogenesis of ophthalmic diseases or conditions described herein. In some embodiments, administration of ophthalmic pharmaceutical compositions described herein results in a decrease in the production of lachrymal secretions. A reduction of lachrymal secretions (e.g. mucus production) results in a decrease of the symptoms associated with such ophthalmic diseases or conditions.

In some embodiments, any ophthalmic pharmaceutical composition described herein comprises a $DP_2$ receptor antagonist in combination with second therapeutic agent and is administered to an eye and/or a related tissue and treats, and/or inhibits or reduces the symptoms of any prostaglandin $D_2$-mediated or prostaglandin $D_2$-dependent disease or condition affecting the eyes.

As used herein, an ophthalmic disease or condition or disorder includes any abnormal state of an eye or a tissue related thereto. In certain instances, an ophthalmic disease or condition is caused or exacerbated by an immune disorder (e.g. an autoimmune disorder); a proliferation disorder; contact with an allergen, and/or an irritant; a mast cell disorder (e.g., over-production of prostaglandin $D_2$ and/or cytokines); or combinations thereof.

Ophthalmic diseases or conditions include, but are not limited to, age-related macular degeneration, allergic conjunctivitis, eosinophilic keratitis, anterior segment scarring, blepharitis, blepharoconjunctivitis, a bullous disorder, cicatricial pemphigoid, conjunctival melanoma, conjunctivitis, contact lens-associated giant papillary conjunctivitis, diabetic retinopathy, dry eye, episcleritis, glaucoma, gliosis, granuloma annulare, Graves' ophthalmopathy, intraocular melanoma, keratitis, keratoconjunctivitis, pain, pinguecula, post-surgical pain, proliferative vitreoretinopathy, pterygia, scarring, scleritis, Sjögren's syndrome, uveitis, atopic keratoconjunctivitis and vernal keratoconjunctivitis.

In some embodiments, an ophthalmic pharmaceutical composition described herein is administered to the eyes of a mammal before or after contact with an allergen and/or irritant and/or an infectious agent. In some embodiments, an ophthalmic pharmaceutical composition described herein is administered before or after a physical trauma (e.g., surgery). In some embodiments, administration of an ophthalmic pharmaceutical composition described herein to the eyes reduces or eliminates ocular itching that results from contact with an allergen and/or irritant and/or an infectious agent.

In some embodiments, an ophthalmic pharmaceutical composition described herein is administered to the eyes of a mammal to treat an ophthalmic disease or condition, wherein the ophthalmic disease or condition is conjunctivitis. In certain instances, conjunctivitis results from exposure to an allergen. In certain instances, conjunctivitis results from a bacterial, viral or chlamydial infection. In certain instances, prostaglandin $D_2$ and/or cytokines (e.g., IL-4) mediate some or all of the symptoms associated with conjunctivitis. In one aspect, symptoms associated with conjunctivitis include, but are not limited to, vessel dilation, edema, hyperemia. In some embodiments, an ophthalmic pharmaceutical composition described herein is administered to the eyes to treat allergic conjunctivitis. In some embodiments, an ophthalmic pharmaceutical composition described herein is administered to the eyes to treat itching associated with allergic conjunctivitis.

In some embodiments, an ophthalmic pharmaceutical composition described herein is administered to the eyes of a mammal to treat or prevent ocular itching. In some embodiments, ocular itching is a symptom of allergies. In some embodiments, ocular itching is a symptom of allergic conjunctivitis. In some embodiments, ocular itching is a symptom of any of the diseases or conditions described herein.

In some embodiments, an ophthalmic pharmaceutical composition described herein is administered to the eyes of a mammal to treat an ophthalmic disease or condition, wherein the ophthalmic disease or condition is keratitis. As used herein, keratitis is a disorder characterized by inflammation of the cornea. In certain instances, prostaglandin $D_2$ and/or cytokines (e.g., IL-4) mediate some or all of the symptoms associated with keratitis (e.g., vessel dilation, edema, hyperemia). In certain instances, antagonism of $DP_2$ receptors reduces the concentration of cytokines (e.g., IL-4) associated with keratitis. In some embodiments, antagonism of $DP_2$ receptors in the eye treats keratitis.

In some embodiments, an ophthalmic pharmaceutical composition described herein is administered to the eyes of a mammal to treat an ophthalmic disease or condition, wherein the ophthalmic disease or condition is keratoconjunctivitis (i.e., a combination of conjunctivitis and keratitis (i.e., corneal inflammation)). In certain instances, prostaglandin $D_2$ and/or cytokines (e.g., IL-4) mediate some or all of the symptoms associated with keratitis and conjunctivitis (e.g., vessel dilation, edema, hyperemia). In certain instances, antagonism of $DP_2$ receptors in the eye reduces the concentration of cytokines associated with keratitis and conjunctivitis. In some embodiments, antagonizing $DP_2$ receptors in the eye treats keratoconjunctivitis. In some embodiments, antagonizing $DP_2$ receptors in the eye treats vessel dilation, edema, hyperemia, or combinations thereof. In some embodiments, antagonizing $DP_2$ receptors in the eye reduces accumulation of mucin associated with keratitis and/or conjunctivitis.

In some embodiments, an ophthalmic pharmaceutical composition described herein is administered to the eyes of a mammal to treat an ophthalmic disease or condition, wherein the ophthalmic disease or condition is blepharitis. As used herein, blepharitis is an ophthalmic disorder characterized by inflammation of the eyelid margins. In certain instances, prostaglandin $D_2$ and/or cytokines (e.g., IL-4) mediate some or all of the symptoms associated with blepharitis (e.g., vessel dilation, edema, hyperemia). In certain instances, antagonizing $DP_2$ receptors in the eye reduces the concentration of cytokines associated with blepharitis. In some embodiments, antagonizing $DP_2$ receptors in the eye treats blepharitis and/or reduces mucin accumulation associated with blepharitis.

In some embodiments, an ophthalmic pharmaceutical composition described herein is administered to the eyes of a mammal to treat blepharoconjunctivitis (i.e., a combination of conjunctivitis and blepharitis (i.e., inflammation of an eyelid)). In certain instances, prostaglandin $D_2$ and/or cytokines mediate some or all of the symptoms associated with blepharitis and conjunctivitis (e.g., vessel dilation, edema, hyperemia). In certain instances, antagonizing $DP_2$ receptors in the eye reduces the concentration cytokines (IL-4) associated with blepharitis and conjunctivitis. In some embodiments, antagonizing $DP_2$ receptors in the eye treats blepharoconjunctivitis. In some embodiments, antagonizing $DP_2$ receptors in the eye treats mucin accumulation, vessel dilation, edema, hyperemia, or combinations thereof associated with blepharoconjunctivitis.

In some embodiments, an ophthalmic pharmaceutical composition described herein is administered to the eyes of a mammal to treat scleritis. As used herein, scleritis is a disorder characterized by inflammation of the sclera. In certain instances, prostaglandin $D_2$ and/or cytokines (e.g., IL-4) mediate some or all of the symptoms associated with scleritis (e.g., vessel dilation, edema, hyperemia). In certain instances, antagonizing $DP_2$ receptors in the eye reduces the concentration of cytokines associated with scleritis. In some embodiments, antagonizing $DP_2$ receptors in the eye treats scleritis.

In some embodiments, an ophthalmic pharmaceutical composition described herein is administered to the eyes of a mammal to treat episcleritis. As used herein, episcleritis is a disorder characterized by inflammation of the episclera. In certain instances, prostaglandin $D_2$ and/or cytokines (e.g., IL-4) mediate some or all of the symptoms associated with episcleritis (e.g., vessel dilation, edema, hyperemia). In certain instances, antagonizing $DP_2$ receptors in the eye reduces the concentration of cytokines associated with episcleritis. In some embodiments, antagonizing $DP_2$ receptors in the eye treats episcleritis.

In some embodiments, an ophthalmic pharmaceutical composition described herein is administered to the eyes of a mammal to treat uveitis. As used herein, uveitis is a disorder characterized by inflammation of the uvea. In certain instances, prostaglandin $D_2$ and/or cytokines (e.g., IL-4) mediate some or all of the symptoms associated with uveitis (e.g., vessel dilation, edema, hyperemia, mucin accumulation). In certain instances, antagonizing $DP_2$ receptors in the eye reduces the concentration of cytokines associated with uveitis. In some embodiments, antagonizing $DP_2$ receptors in the eye treats uveitis. In some embodiments, antagonizing $DP_2$ receptors in the eye treats vessel dilation, edema, hyperemia, or reduces mucin accumulation, or combinations thereof.

In some embodiments, an ophthalmic pharmaceutical composition described herein is administered to the eyes of a mammal to treat Sjögren's syndrome. In certain instances, Sjorgren's Syndrome is an autoimmune disorder in which immune cells attack and destroy the exocrine glands that produce tears. In certain instances, prostaglandin $D_2$ and/or cytokines (e.g., IL-4) mediate some or all of the symptoms associated with Sjorgren's Syndrome (e.g., vessel dilation, edema, hyperemia). In certain instances, antagonizing $DP_2$ receptors in the eye reduces the concentration of cytokines associated with Sjorgren's Syndrome. In some embodiments, antagonizing $DP_2$ receptors in the eye treats Sjorgren's Syndrome. In some instances, reducing $DP_2$ receptor activity inhibits the chemotaxis of eosinophils to tear ducts.

In some embodiments, an ophthalmic pharmaceutical composition described herein is administered to the eyes of a mammal to treat Graves' ophthalmopathy (also known as Graves' thyroid-associated or dysthyroid orbitopathy or exophthalmos). Graves' ophthalmopathy is an autoimmune inflammatory disorder affecting the orbit of an eye. In certain instances, an immune system identifies thyroid stimulating hormone receptor (TSH-R) an antigen and attacks it. In certain instances, prostaglandin $D_2$ and/or cytokines (e.g., IL-4) mediate some or all of the symptoms associated with Graves' ophthalmopathy (e.g., vessel dilation, edema, hyperemia). In certain instances, inhibiting binding of prostaglandin $D_2$ to $DP_2$ receptors reduces the concentration of cytokines associated with Graves' ophthalmopathy. In some embodiments, inhibiting $DP_2$ receptor activity treats Graves' ophthalmopathy. In some instances, reducing $DP_2$ receptor activity inhibits the chemotaxis of eosinophils to the orbit of the eye. In some embodiments, reducing $DP_2$ receptor activity treats vessel dilation, edema, hyperemia, or combinations thereof.

In some embodiments, an ophthalmic pharmaceutical composition described herein is administered to the eyes of a mammal to treat a bullous disorder. In certain instances, a bullous disorder is characterized by the formation of blisters (i.e., the accumulation of fluid between cells in a tissue). In certain instances, bullous disorders are autoimmune disorders. In certain instances, prostaglandin $D_2$ and/or cytokines (e.g., IL-4) mediate some or all of the symptoms associated with bullous disorders (e.g., induce the exudation of plasma from capillaries to tissues). In certain instances, inhibiting binding of prostaglandin $D_2$ to $DP_2$ receptors reduces the concentration of cytokines associated with bullous disorders. In some embodiments, inhibiting $DP_2$ receptor activity treats bullous disorders. In some instances, inhibiting $DP_2$ receptor activity inhibits the exudation of plasma from capillaries to tissues. In some instances, inhibiting $DP_2$ receptor activity inhibits mucin accumulation associated with bullous disorders.

In some embodiments, an ophthalmic pharmaceutical composition described herein is administered to the eyes of a mammal to treat scarring in the eye. In certain instances, a scar is an area of fibrous tissue that results from the overproduction of collagen. In certain instances, prostaglandin $D_2$ and/or cytokines (e.g., IL-4) mediate some or all of the symptoms associated with scarring (e.g., vessel dilation, edema, hyperemia). In certain instances, inhibiting binding of prostaglandin $D_2$ to $DP_2$ receptors reduces the concentration of cytokines associated with scarring. In some embodiments, inhibiting $DP_2$ receptor activity treats scarring (e.g., reduces inflammation at site of wound before or after surgery). In some embodiments, inhibiting $DP_2$ receptor activity treats mucin accumulation and/or fibrous tissue accumulation.

In some embodiments, an ophthalmic pharmaceutical composition described herein is administered to the eyes of a mammal to treat a melanoma in the eye (e.g., intraocular melanoma, and/or conjunctival melanoma). In certain instances, a melanoma is a proliferative disorder of melanocytes. In certain instances, prostaglandin $D_2$ and/or cytokines stimulate the growth of melanocytes. Further, in certain instances, inflammation facilitates the growth of a melanoma. In certain instances, prostaglandin $D_2$ mediates inflammation associated with a melanoma. In certain instances, prostaglandin $D_2$ and/or cytokines (e.g., IL-4) mediate some or all of the symptoms associated with melanoma (e.g., vessel dilation, edema, hyperemia). In certain instances, inhibiting binding of prostaglandin $D_2$ to $DP_2$ receptors reduces the concentration of cytokines associated with melanoma and slows and/or inhibits the growth of melanocytes associated with an intraocular melanoma. In some embodiments, inhibiting $DP_2$ receptor activity treats intraocular melanoma and/or conjunctival melanoma (e.g., reduces inflammation and/or proliferation).

In some embodiments, an ophthalmic pharmaceutical composition described herein is administered to the eyes of a mammal to treat an eye infection (e.g., a bacterial, viral or chlamydial infection). In certain instances, an infection causes the production of lachrymal secretions (e.g., mucus, mucin, pus or the like). In certain instances, prostaglandin D2 and/or cytokines (e.g. IL-4) mediate the production of mucus in an infected eye. In certain instances, inhibiting $DP_2$ receptor activity reduces the concentration of cytokines (e.g. IL-4) associated with lachrymal secretions and slows and/or inhibits the production of mucus associated with an ocular infection. In certain instances, inhibiting the binding of prostaglandin $D_2$ to $DP_2$ receptors reduces mucus production associated with an eye infection.

In some embodiments, any ophthalmic pharmaceutical composition described herein comprises a $DP_2$ receptor antagonist in combination with any second therapeutic agent and is administered to an eye for the treatment of any prostaglandin $D_2$-mediated or prostaglandin $D_2$-dependent disease or condition described herein. In some embodiments, the effects of a $DP_2$ receptor antagonist compound and the second therapeutic agent are additive, i.e., administration of a combination of a $DP_2$ receptor antagonist compound and the second therapeutic agent provides greater therapeutic benefit than administration of either compound alone.

$DP_2$ Receptor Antagonists

In one aspect, the ophthalmic pharmaceutical compositions disclosed herein comprise at least one $DP_2$ receptor antagonist compound. In some embodiments, the $DP_2$ receptor antagonist is selected from compounds disclosed in International Patent Application No. PCT/US09/35174 (entitled Antagonists of Prostaglandin $D_2$ receptors); International Patent Application No. PCT/US08/82056 (entitled Antagonists of PG $D_2$ receptors (entitled Antagonists of PG $D_2$ receptors"); International Patent Application No. PCT/US08/82082 (entitled Antagonists of PG $D_2$ receptors (entitled Antagonists of PG $D_2$ receptors"); International Patent Application No. PCT/US0932495 (entitled N,N-disubstituted aminoalkylbiphenyl antagonists of prostaglandin $D_2$ receptors); International Patent Application No. PCT/US09/32499 (entitled "N,N-disubstituted aminoalkylbiphenyl antagonists of prostaglandin $D_2$ receptors"); International Patent Application No. PCT/US09/33961 (entitled "Cyclic diaryl ether compounds as antagonists of prostaglandin $D_2$ receptors"); International Patent Application No. PCT/US09/38291 (entitled "Aminoalkylphenyl antagonists of prostaglandin $D_2$ receptors"); U.S. Provisional Application No. 61/078,311 (entitled "Heteroalkyl antagonists of prostaglandin $D_2$ receptors"); U.S. Provisional Application No. 61/101,074 (entitled "Heteroaryl antagonists of prostaglandin $D_2$ receptors"); U.S. Provisional Application No. 61/054,093 (entitled "Tricyclic antagonists of prostaglandin $D_2$ receptors"); U.S. Provisional Application No. 61/107,638 (entitled "Tricyclic antagonists of prostaglandin $D_2$ receptors"); U.S. Provisional Application No. 61/075,242 (entitled "Cycloaklane[B]indole antagonists of prostaglandin $D_2$ receptors"); U.S. provisional application No. 61/101,964 (entitled "Heteroaryl antagonists of prostaglandin $D_2$ receptors"); U.S. Provisional Application No. 61/103,872 (entitled "Heteroalkyl biphenyl antagonists of prostaglandin $D_2$ receptors"); U.S. Provisional Application No. 61/115,259 (entitled "Heterocyclic antagonists of prostaglandin $D_2$ receptors"); U.S. Provisional Application No. 61/112,044 (entitled "Cycloaklane[13]azaindole antagonists of prostaglandin D2 receptors"); U.S. Provisional Application No. 61/147,437 (entitled "Indolozine compounds as prostaglandin $D_2$ receptor antagonists"); U.S. Provisional Application No. 61/025,597; U.S. Provisional Application No. 61/110,496; U.S. application Ser. No. 12/362,439; International Patent Application No. PCT/US09/49621; International Patent Application No. PCT/US09/49631; U.S. application Ser. No. 12/497,343; International Patent Application No. PCT/US09/58655; International Patent Application No. PCT/US09/58663; U.S. application Ser. No. 12/568,571; International Patent Application No. PCT/US09/44219; International Patent Application No. PCT/US09/48327; International Patent Application No. PCT/US09/59256; International Patent Application No. PCT/US09/59891; International Patent Application No. PCT/US09/64630; International Patent Application No. PCT/US09/63439; International Patent Application No. PCT/US09/63438; U.S. application Ser. No. 12/613,424; International Patent Application No. PCT/US2010/22145; or pharmaceutically acceptable salt; pharmaceutically acceptable solvate; metabolite, prodrug or N-oxide thereof, each disclosure is incorporated by reference for such compounds.

In some embodiments, the $DP_2$ receptor antagonist is ramatroban, AMG 009, AMG 853, Compound 14 of WO 09/085,177, AZD1981, AZD8075, AZD5985, ARRY-005, ARRY-006, ARRY-063, ODC9101 (OC459), OC499, OC1768, OC2125, OC2184, QAV680, MLN6095, ACT-129968, ADC3680, SAR398171, S555739, AP768, [2'-(3-Benzyl-1-ethyl-ureidomethyl)-6-methoxy-4'-trifluoromethyl-biphenyl-3-yl]-acetic acid, {3-[2-tert-Butylsulfanylmethyl-4-(2,2-dimethyl-propionylamino)-phenoxy]-4-methoxy-phenyl}-acetic acid, TM30642, TM30643, TM30089, TM27632, and TM3170, {2'-[(N-cyclopropanecarbonyl-N-ethyl-amino)-methyl]-6-methoxy-4'-trifluoromethyl-biphenyl-3-yl}-acetic acid, [2'-[(N-cyclopropanecarbonyl-N-ethyl-amino)-methyl]-4'-(6-ethoxy-pyridin-3-yl)-6-methoxy-biphenyl-3-yl]-acetic acid, (5-{2-[(N-benzyloxycarbonyl-N-ethyl-amino)-methyl]-4-trifluoromethyl-phenyl}-pyridin-3-yl)-acetic acid, or {8-[(4-fluoro-benzenesulfonyl)-methyl-amino]-6,7,8,9-tetrahydro-pyrido[3,2-b]indol-5-yl}-acetic acid, or pharmaceutically acceptable salt; pharmaceutically acceptable solvate; metabolite, prodrug or N-oxide thereof.

In some embodiments, the $DP_2$ receptor antagonist is a compound having the structure of Formula (I), pharmaceutically acceptable salt, pharmaceutically acceptable solvates, or prodrug thereof:

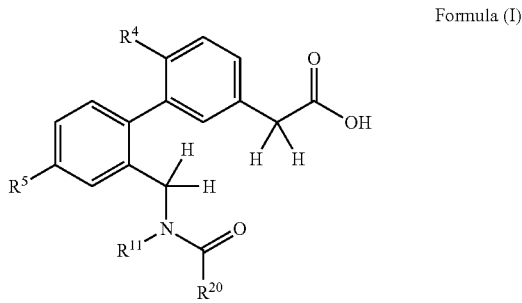

Formula (I)

wherein,
$R^4$ is H, halogen, —CN, —OH, $C_1$-$C_4$alkyl, $C_1$-$C_4$alkoxy, $C_1$-$C_4$-fluoroalkyl, $C_1$-$C_4$-fluoroalkoxy, or $C_1$-$C_4$heteroalkyl;
$R^5$ is H, halogen, —CN, —NO$_2$, —OH, —OR$^{13}$, —SR$^{12}$, —S(=O)R$^{12}$, —S(=O)$_2$R$^{12}$, —NHS(=O)$_2$R$^{12}$, —C(=O)R$^{12}$, —OC(=O)R$^{12}$, —CO$_2$R$^{13}$, —OCO$_2$R$^{13}$, —CH(R$^{13}$)$_2$, —(=O)N(R$^{13}$)$_2$, —OC(=O)N(R$^{13}$)$_2$, —NHC(=O)NH(R$^{13}$), —NHC(=O)R$^{12}$, —NHC(=O)OR$^{12}$, —C(OH)(R$^{13}$)$_2$, —C$_1$-C$_6$alkyl, C$_1$-C$_6$-fluoroalkyl, C$_1$-C$_6$-fluoroalkoxy, C$_1$-C$_6$alkoxy, or C$_1$-C$_6$heteroalkyl;
or $R^5$ is $C_3$-$C_{10}$cycloalkyl, a substituted or unsubstituted $C_2$-$C_{10}$heterocycloalkyl, a substituted or unsubstituted phenyl, a substituted or unsubstituted naphthyl, a substituted or unsubstituted monocyclic heteroaryl, or a substituted or unsubstituted bicyclic heteroaryl, wherein if $R^5$ is substituted, then $R^5$ is substituted with 1, or 2 $R^{21}$ groups
$R^{20}$ is $C_1$-$C_4$alkyl, $C_3$-$C_6$cycloalkyl, —CH$_2$O—C$_1$-C$_4$alkyl, —CH$_2$O-(substituted or unsubstituted phenyl), —CH(CH$_3$)—O-(substituted or unsubstituted phenyl), —C(CH$_3$)$_2$—O-(substituted or unsubstituted phenyl), —CH$_2$OCH$_2$-(substituted or unsubstituted phenyl), —OC$_1$-C$_4$alkyl, —O—CH$_2$-(substituted or unsubstituted phenyl), —O—CH(CH$_3$)-(substituted or unsubstituted phenyl), —NR$^{16}$C$_1$—C$_4$alkyl, —NR$^{16}$—CH$_2$-(substituted or unsubstituted phenyl), or —NR$^{16}$—CH(CH$_3$)-(substituted or unsubstituted phenyl), wherein if the phenyl of R$^{20}$ is substituted, then the phenyl is substituted with 1, or 2 $R^{21}$ groups;
each $R^{21}$ is independently selected from halogen, —OH, —OC$_1$-C$_4$alkyl, C$_1$-C$_4$alkyl, and —CF$_3$;
$R^{16}$ is H or $C_1$-$C_4$alkyl;
$R^{11}$ is $C_1$-$C_4$alkyl, $C_1$-$C_4$-fluoroalkyl, or $C_3$-$C_6$cycloalkyl;
$R^{12}$ is $C_1$-$C_4$alkyl, $C_1$-$C_4$heteroalkyl, or $C_1$-$C_4$-fluoroalkyl;
each $R^{13}$ is independently selected from H, $C_1$-$C_4$alkyl, $C_1$-$C_4$heteroalkyl, and $C_1$-$C_4$-fluoroalkyl.

In some embodiments, $R^{11}$ is —CH$_3$, —CH$_2$CH$_3$, —CF$_3$, —CH$_2$CF$_3$, cyclopropyl, cyclobutyl, or cyclopentyl. In some embodiments, $R^{11}$ is —CH$_2$CH$_3$ or —CH$_2$CF$_3$. In some embodiments, $R^{11}$ is —CH$_2$CH$_3$.

In some embodiments, $R^5$ is H, halogen, —CN, —NO$_2$, —OH, —OR$^{13}$, —SR$^{12}$, —S(=O)R$^{12}$, —S(=O)$_2$R$^{12}$, —NHS(=O)$_2$R$^{12}$, —C(=O)R$^{12}$, —OC(=O)R$^{12}$, —CO$_2$R$^{13}$, —OCO$_2$R$^{13}$, —N(R$^{13}$)$_2$, —C(=O)N(R$^{13}$)$_2$, —OC(=O)N(R$^{13}$)$_2$, —NHC(=O)NH(R$^{13}$), —NHC(=O) R$^{12}$, —NHC(=O)OR$^{12}$, —C(OH)(R$^{13}$)$_2$, —C$_1$-C$_4$alkyl, $C_1$-$C_4$fluoroalkyl, $C_1$-$C_4$fluoroalkoxy, $C_1$-$C_4$alkoxy, or $C_1$-$C_4$heteroalkyl; $R^{12}$ is $C_1$-$C_4$alkyl; each $R^{13}$ is independently selected from H, and $C_1$-$C_4$alkyl. In some embodiments, $R^5$ is H, —$CF_3$, —$CO_2H$, Br, —NH—C(=O)—$CH_3$, —NH—C(=O)—$OCH_3$, —NH—$SO_2CH_3$, —$SCH_3$, —$SO_2CH_3$, —NH—(C=O)—$CH_3$, —NH—$SO_2$—$CH_3$, or —C($CH_3$)$_2$—(OH).

In some embodiments, $R^{20}$ is $C_1$-$C_4$alkyl, $C_3$-$C_6$cycloalkyl, —$CH_2O$—$C_1$-$C_4$alkyl, —$CH_2O$-(substituted or unsubstituted phenyl), —CH($CH_3$)—O-(substituted or unsubstituted phenyl), —C($CH_3$)$_2$—O-(substituted or unsubstituted phenyl), —$CH_2OCH_2$-(substituted or unsubstituted phenyl), —O$C_1$-$C_4$alkyl, —O—$CH_2$-(substituted or unsubstituted phenyl), —O—CH($CH_3$)-(substituted or unsubstituted phenyl), —$NR^{16}C_1$-$C_4$alkyl, —$NR^{16}$—$CH_2$-(substituted or unsubstituted phenyl), or —$NR^{16}$—CH($CH_3$)-(substituted or unsubstituted phenyl), wherein if the phenyl of $R^{20}$ is substituted then the phenyl is substituted with 1 or 2 $R^{21}$ groups.

In some embodiments, $R^4$ is H, F, Cl, Br, —OH, —$CH_3$, —$OCH_3$, —$CF_3$, or —$OCF_3$; $R^5$ is H, halogen, —CN, —$NO_2$, —OH, —S(=O)$_2CH_3$, —NHS(=O)$_2CH_3$, —C(=O)$CH_3$, —OC(=O)$CH_3$, —$CO_2H$, —$CO_2CH_3$, —$CO_2CH_2CH_3$, —$NH_2$, —C(=O)$NH_2$, —NHC(=O)$CH_3$, —$CH_3$, —$CF_3$, —$OCF_3$, —$OCH_3$, —$CH_2OH$, or —C($CH_3$)$_2OH$.

In some embodiments, $R^{20}$ is —$CH_3$, —$CH_2CH_3$, cyclopropyl, cyclobutyl, cyclopentyl, cyclohexyl, —$CH_2OCH_3$, —$CH_2O$-(substituted or unsubstituted phenyl), —CH($CH_3$)—O-(substituted or unsubstituted phenyl), —C($CH_3$)$_2$—O-(substituted or unsubstituted phenyl), —$CH_2OCH_2$-(substituted or unsubstituted phenyl), wherein if the phenyl of $R^{20}$ is substituted then the phenyl is substituted with 1 or 2 $R^{21}$ groups.

In some embodiments, each $R^{21}$ is independently selected from F, Cl, Br, —OH, —$OCH_3$, —$OCH_2CH_3$, —$CH_2CH_3$, —$CH_3$, and —$CF_3$. In some embodiments, each $R^{21}$ is independently selected from F, Cl, Br, —OH, —$OCH_3$, —$CH_3$, and —$CF_3$.

In some embodiments, $R^4$ is H, F, Cl, Br, —$CH_3$, —$OCH_3$, —$CF_3$, or —$OCF_3$; $R^5$ is halogen, —$CH_3$, $CF_3$, —$OCF_3$, or —$OCH_3$.

In some embodiments, $R^{20}$ is —$CH_3$, —$CH_2CH_3$, cyclopropyl, cyclobutyl, cyclopentyl, cyclohexyl, —$CH_2OCH_3$, —$CH_2O$-(substituted or unsubstituted phenyl), —CH($CH_3$)—O-(substituted or unsubstituted phenyl), —C($CH_3$)$_2$—O-(substituted or unsubstituted phenyl), —$CH_2OCH_2$-(substituted or unsubstituted phenyl), wherein if the phenyl of $R^{20}$ is substituted, then the phenyl is substituted with 0, 1, or 2 $R^{21}$ groups.

In some embodiments, $R^{20}$ is —$CH_3$, cyclopropyl, —$CH_2OCH_3$, —$CH_2O$-(substituted or unsubstituted phenyl), —$CH_2OCH_2$-(substituted or unsubstituted phenyl), wherein if the phenyl of $R^{20}$ is substituted, then the phenyl is substituted with 1, or 2 $R^{21}$ groups. In some embodiments, $R^{20}$ is cyclopropyl.

In some embodiments, $R^{20}$ is —O—$C_1$-$C_4$alkyl, —O—$CH_2$-(substituted or unsubstituted phenyl), or —O—CH($CH_3$)-(substituted or unsubstituted phenyl); wherein if the phenyl of $R^{20}$ is substituted, then the phenyl is substituted with 1 or 2 $R^{21}$ groups.

In some embodiments, $R^{20}$ is —O—$CH_2$-(substituted or unsubstituted phenyl), wherein if the phenyl of $R^{20}$ is substituted, then the phenyl is substituted with 1, or 2 $R^{21}$ groups.

In some embodiments, $R^{20}$ is —$NR^{16}$ $C_1$-$C_4$alkyl, —$NR^{16}$—$CH_2$-(substituted or unsubstituted phenyl), or —$NR^{16}$—CH($CH_3$)-(substituted or unsubstituted phenyl), wherein if the phenyl of $R^{20}$ is substituted then the phenyl is substituted with 1, or 2 $R^{21}$ groups; $R^{16}$ is H, —$CH_3$, or —$CH_2CH_3$.

In some embodiments, $R^{20}$ is —NH—$CH_2$-(substituted or unsubstituted phenyl), wherein if the phenyl of $R^{20}$ is substituted, then the phenyl is substituted with 1, or 2 $R^{21}$ groups. In some embodiments, $R^{20}$ is —NH—$CH_2$-phenyl.

In some embodiments, $R^4$ is F, Cl, Br, —$CH_3$, —$OCH_3$, —$CF_3$, or —$OCF_3$.

In some embodiments, $R^5$ is F, Cl, Br, —$CH_3$, —$CF_3$, —$OCF_3$, or —$OCH_3$.

In some embodiments, $R^{11}$ is —$CH_3$, —$CH_2CH_3$, or —$CH_2CF_3$.

In some embodiments, each $R^{21}$ is independently selected from F, Cl, Br, —OH, —$OCH_3$, —$CH_3$, and —$CF_3$. In some embodiments, each $R^{21}$ is independently selected from F, Cl, Br, —OH, —$OCH_3$, —$OCH_2CH_3$, —$CH_3$, and —$CF_3$. In some embodiments, each $R^{21}$ is independently selected from F, Cl, and Br.

In some embodiments, $R^4$ is —$OCH_3$. In some embodiments, $R^5$ is —$CF_3$.

In some embodiments, $R^{11}$ is —$CH_3$, or —$CH_2CH_3$. In some embodiments, $R^{11}$ is —$CH_2CH_3$.

In some embodiments, $R^4$ is H, F, Cl, Br, —OH, —$CH_3$, —$OCH_3$, —$CF_3$, or —$OCF_3$;

In some embodiments, $R^{11}$ is cyclopropyl, cyclobutyl, or cyclopentyl.

In some embodiments, $R^5$ is cyclopropyl, cyclobutyl, cyclopentyl, cyclohexyl, pyrrolidinyl, piperidinyl, morpholinyl, piperazinyl, thiomorpholinyl, or a substituted or unsubstituted group selected from phenyl, naphthyl, furanyl, thienyl, pyrrolyl, oxazolyl, thiazolyl, imidazolyl, pyrazolyl, isoxazolyl, isothiazolyl, oxadiazolyl, triazolyl, tetrazolyl, pyridinyl, pyridazinyl, pyrazinyl, pyrimidinyl, triazinyl, indolyl, benzofuranyl, benzothienyl, indazolyl, benzimidaolyl, benzthiazolyl, quinolinyl, isoquinolinyl, cinnolinyl, phthalazinyl, quinazolinyl, and quinoxalinyl, where if $R^5$ is substituted, then $R^5$ is substituted with 1, or 2 $R^{21}$ groups.

In some embodiments, $R^5$ is a substituted or unsubstituted group selected from phenyl, naphthyl, pyrrolyl, oxazolyl, thiazolyl, imidazolyl, pyrazolyl, isoxazolyl, isothiazolyl, oxadiazolyl, triazolyl, tetrazolyl, pyridinyl, pyridazinyl, pyrazinyl, pyrimidinyl, triazinyl, indolyl, benzofuranyl, benzothienyl, indazolyl, benzimidaolyl, benzthiazolyl, quinolinyl, isoquinolinyl, cinnolinyl, phthalazinyl, quinazolinyl, and quinoxalinyl, where if $R^5$ is substituted, then $R^5$ is substituted with 1 or 2 $R^{21}$ groups.

In some embodiments, $R^5$ is a substituted or unsubstituted group selected from pyrrolyl, oxazolyl, thiazolyl, imidazolyl, pyrazolyl, isoxazolyl, isothiazolyl, oxadiazolyl, triazolyl, tetrazolyl, pyridinyl, pyridazinyl, pyrazinyl, pyrimidinyl, triazinyl, indolyl, benzofuranyl, benzothienyl, indazolyl, benzimidaolyl, benzthiazolyl, quinolinyl, isoquinolinyl, where if $R^5$ is substituted, then $R^5$ is substituted with 1 or 2 $R^{21}$ groups.

In some embodiments, $R^5$ is a substituted or unsubstituted pyridinyl, where if $R^5$ is substituted, then $R^5$ is substituted with 1 or 2 $R^{21}$ groups.

In some embodiments, $R^4$ is F, Cl, Br, —$CH_3$, —$OCH_3$, —$CF_3$, or —$OCF_3$; $R^{11}$ is —$CH_3$, —$CH_2CH_3$, or —$CH_2CF_3$;

In some embodiments, $R^4$ is —$OCH_3$; $R^{11}$ is —$CH_3$, or —$CH_2CH_3$.

In some embodiments, $R^5$ is a substituted or unsubstituted group selected from pyrrolyl, oxazolyl, thiazolyl, imidazolyl, pyrazolyl, isoxazolyl, isothiazolyl, pyridinyl, pyridazinyl, pyrazinyl, pyrimidinyl, quinolinyl, and isoquinolinyl, where if $R^5$ is substituted, then $R^5$ is substituted with 1, or 2 $R^{21}$ groups.

In some embodiments, $R^5$ is cyclopropyl, phenyl, pyrrolidin-1-yl, pyrazol-1-yl, 1H-pyrazol-4-yl, 1-methyl-1H-pyrazol-4-yl, oxazol-2-yl, pyridin-2-yl, 6-ethoxy-pyridin-3-yl, 5-fluoro-pyridin-2-yl, 5-methoxy-pyrimidin-2-yl, or quinolin-7-yl.

In some embodiments, $R^5$ is pyrazol-1-yl, 1H-pyrazol-4-yl, 1-methyl-1H-pyrazol-4-yl, oxazol-2-yl, pyridin-2-yl, 6-ethoxy-pyridin-3-yl, 5-fluoro-pyridin-2-yl, 5-methoxy-pyrimidin-2-yl, or quinolin-7-yl.

In some embodiments, $R^5$ is substituted or unsubstituted pyridin-2-yl, substituted or unsubstituted pyridin-3-yl, or substituted or unsubstituted pyridin-4-yl, where if $R^5$ is substituted, then $R^5$ is substituted with 1 or 2 $R^{21}$ groups. In some embodiments, $R^5$ is pyridin-2-yl, 6-ethoxy-pyridin-3-yl, 5-fluoro-pyridin-2-yl, or 5-methoxy-pyrimidin-2-yl. In some embodiments, $R^5$ is pyridin-2-yl, 6-methyl-pyridin-3-yl, 6-ethyl-pyridin-3-yl, 6-methoxy-pyridin-3-yl, 6-ethoxy-pyridin-3-yl, 5-fluoro-pyridin-2-yl, 5-methyl-pyridin-2-yl, 5-ethyl-pyridin-2-yl, 5-methoxy-pyrimidin-2-yl or 5-ethoxy-pyrimidin-2-yl. In some embodiments, $R^5$ is 6-ethoxy-pyridin-3-yl.

In some embodiments, the $DP_2$ receptor antagonist is [2'-(3-benzyl-1-ethyl-ureidomethyl)-6-methoxy-4'-trifluoromethyl-biphenyl-3-yl]-acetic acid, {2'-[(N-cyclopropanecarbonyl-N-ethyl-amino)-methyl]-6-methoxy-4'-trifluoromethyl-biphenyl-3-yl}-acetic acid, [2'-[(N-cyclopropanecarbonyl-N-ethyl-amino)-methyl]-4'-(6-ethoxy-pyridin-3-yl)-6-methoxy-biphenyl-3-yl]-acetic acid, or a pharmaceutically acceptable salt, pharmaceutically acceptable solvate, or prodrug thereof.

In some embodiments, the $DP_2$ receptor antagonist is a compound having the structure of Formula (II), pharmaceutically acceptable salt, pharmaceutically acceptable solvate, or prodrug thereof:

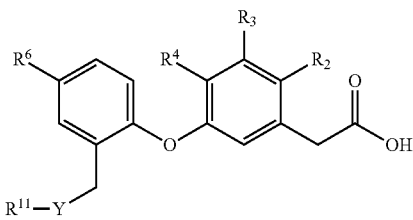

Formula (II)

wherein, each of $R^2$, $R^3$, and $R^4$ is independently H, F, Cl, Br, I, —CN, —OR$^{12}$, —C$_1$-C$_6$alkyl, C$_1$-C$_6$fluoroalkyl, C$_1$-C$_6$fluoroalkoxy, C$_1$-C$_6$alkoxy, or C$_1$-C$_6$heteroalkyl;

$R^6$ is F, Cl, Br, I, —CN, —NO$_2$, —OH, —O(C$_1$-C$_6$alkyl), —S(=O)$_2$R$^{12}$, —N(C$_1$-C$_4$alkyl)S(=O)$_2$R$^{12}$, —NHS(=O)$_2$R$^{12}$, —S(=O)$_2$N(R$^{13}$)$_2$, —C(=O)R$^{12}$, —CO$_2$(C$_1$-C$_6$alkyl), —NH$_2$, —C(=O)NH(R$^{13}$), —C(=O)N(R$^{13}$)$_2$, —OC(=O)NH(R$^{13}$), —OC(=O)N(R$^{13}$)$_2$, —N(C$_1$-C$_4$alkyl)C(=O)N(R$^{13}$)$_2$, —NHC(=O)N(R$^{13}$)$_2$, —NHC(=O)NH(R$^{13}$), —N(C$_1$-C$_4$alkyl)C(=O)R$^{12}$, —NHC(=O)R$^{12}$, —NH—C$_1$-C$_4$alkyl-C(=O)R$^{12}$, —N(C$_1$-C$_4$alkyl)C(=O)OR$^{12}$, —NHC(=O)OR$^{12}$, C$_1$-C$_6$alkyl, C$_1$-C$_6$fluoroalkyl, C$_1$-C$_6$fluoroalkoxy, C$_1$-C$_6$alkoxy, C$_1$-C$_6$heteroalkyl, a substituted or unsubstituted C$_2$-C$_{10}$heterocycloalkyl, a substituted or unsubstituted phenyl, or a substituted or unsubstituted monocyclic or bicyclic heteroaryl containing 0-3 heteroatoms selected from N, O or S;

$R^{11}$ is C$_1$-C$_6$alkyl, C$_1$-C$_6$haloalkyl, C$_1$-C$_6$heteroalkyl, a substituted or unsubstituted phenyl, a substituted or unsubstituted monocyclic or bicyclic heteroaryl containing 0-3 heteroatoms selected from N, O or S, a substituted or unsubstituted —C$_1$-C$_4$alkyl-phenyl, —C$_1$-C$_6$alkylene-N(R$^{17}$)$_2$, —C$_1$-C$_6$alkylene-C(=O)O—R$^{17}$, or —C$_1$-C$_6$alkylene-C(=O)N(R$^{17}$)$_2$;

$R^{17}$ is H, or C$_1$-C$_6$alkyl;

$R^{12}$ is C$_1$-C$_6$alkyl, C$_1$-C$_6$heteroalkyl, C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted phenyl, a substituted or unsubstituted benzyl, a substituted or unsubstituted monocyclic heteroaryl containing 0-3 heteroatoms selected from N, O or S, a substituted or unsubstituted —C$_1$-C$_4$alkyl-C$_3$-C$_{10}$cycloalkyl, a substituted or unsubstituted —C$_1$-C$_4$alkyl-phenyl, or a substituted or unsubstituted —C$_1$-C$_4$alkyl-(monocyclic heteroaryl containing 0 to 3 heteroatoms selected from N, O or S);

each $R^{13}$ is independently selected from H, C$_1$-C$_6$alkyl, C$_1$-C$_6$heteroalkyl, C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted phenyl, a substituted or unsubstituted benzyl, a substituted or unsubstituted monocyclic heteroaryl containing 0-3 heteroatoms selected from N, O or S., a substituted or unsubstituted —C$_1$-C$_4$alkyl-C$_3$-C$_{10}$cycloalkyl, a substituted or unsubstituted —C$_1$-C$_4$alkyl-C$_2$-C$_{10}$heterocycloalkyl, a substituted or unsubstituted —C$_1$-C$_4$alkyl-phenyl, and a substituted or unsubstituted —C$_1$-C$_4$alkyl-(monocyclic heteroaryl containing 0 to 3 heteroatoms selected from N, O or S); or two $R^{13}$ groups attached to the same N atom are taken together with the N atom to which they are attached to form a substituted or unsubstituted C$_2$-C$_{10}$heterocycloalkyl;

Y is —S—, —S(=O)—, or —S(=O)$_2$—.

In some embodiments, $R^6$ is F, Cl, Br, I, —CN, —NO$_2$, —S(=O)$_2$R$^{12}$, —N(C$_1$-C$_4$alkyl)S(=O)$_2$R$^{12}$, —NHS(=O)$_2$R$^{12}$, —S(=O)$_2$N(R$^{13}$)$_2$, —C(=O)R$^{12}$, —CO$_2$(C$_1$-C$_6$alkyl), —NH$_2$, —C(=O)NH(R$^{13}$), —C(=O)N(R$^{13}$)$_2$, —N(C$_1$-C$_4$alkyl)C(=O)N(R$^{13}$)$_2$, —NHC(=O)N(R$^{13}$)$_2$, —NHC(=O)NH(R$^{13}$), —N(C$_1$-C$_4$alkyl)C(=O)R$^{12}$, —NHC(=O)R$^{12}$, —NH—C$_1$-C$_4$alkyl-C(=O)R$^{12}$, —N(C$_1$-C$_4$alkyl)C(=O)OR$^{12}$, —NHC(=O)OR$^{12}$, C$_1$-C$_6$alkyl, C$_1$-C$_6$fluoroalkyl, C$_1$-C$_6$fluoroalkoxy, C$_1$-C$_6$alkoxy, C$_1$-C$_6$heteroalkyl, a substituted or unsubstituted C$_2$-C$_{10}$heterocycloalkyl, a substituted or unsubstituted phenyl, or a substituted or unsubstituted monocyclic heteroaryl containing 0-3 heteroatoms selected from N, O or S.

In some embodiments, $R^{11}$ is isopropyl, tert-butyl, —CH$_2$CF$_3$, —CH$_2$CO$_2$H, —CH$_2$CH$_2$N(CH$_3$)$_2$, phenyl, 4-chlorophenyl, benzyl, phenethyl, thiazol-2-yl, 5-methyl-[1,3,4]thiadiazol-2-yl, pyridin-2-yl, or quinolin-2-yl.

In some embodiments, $R^6$ is —NO$_2$, —N(C$_1$-C$_4$alkyl)S(=O)$_2$R$^{12}$, —NHS(=O)$_2$R$^{12}$, —N(R$^{13}$)$_2$, —N(C$_1$-C$_4$alkyl)C(=O)N(R$^{13}$)$_2$, —NHC(=O)N(R$^{13}$)$_2$, —N(C$_1$-C$_4$alkyl)C(=O)R$^{12}$, —NHC(=O)R$^{12}$, —NH—C$_1$-C$_4$alkyl-C(=O)R$^{12}$, —N(C$_1$-C$_4$alkyl)C(=O)OR$^{12}$, or —NHC(=O)OR$^{12}$.

In some embodiments, $R^6$ is —N(C$_1$-C$_4$alkyl)C(=O)R$^{12}$ or —NHC(=O)R$^{12}$.

In some embodiments, each of $R^2$, $R^3$, and $R^4$ is independently H, F, Cl, Br, I, —CN, —OCH$_3$, —CH$_3$, —CH$_2$CH$_3$, —CHCH$_2$, —CHF$_2$, —CF$_3$, —OCHF$_2$, or —OCF$_3$.

In some embodiments, $R^2$ is H. In some embodiments, $R^3$ is H.

In some embodiments, $R^4$ is H, halogen, —CN, —OH, C$_1$-C$_4$alkyl, C$_1$-C$_4$fluoroalkyl, C$_1$-C$_4$fluoroalkoxy, $C_1$-$C_4$alkoxy, or $C_1$-$C_4$heteroalkyl; $R^6$ is —$NR^{13}$S(=O)$_2R^{12}$, —S(=O)$_2$N($R^{12}$)($R^{13}$), —N($R^{12}$)($R^{13}$), —C(=O)N($R^{12}$)($R^{13}$), —NHC(=O)N($R^{12}$)($R^{13}$), —$NR^{13}$C(=O)$R^{12}$, or —$NR^{13}$C(=O)O$R^{12}$; $R^{11}$ is $C_1$-$C_6$alkyl, $C_1$-$C_6$haloalkyl, $C_1$-$C_6$heteroalkyl, $C_3$-$C_6$cycloalkyl, a substituted or unsubstituted phenyl, a substituted or unsubstituted naphthyl, a substituted or unsubstituted 5-membered heteroaryl, a substituted or unsubstituted 6-membered heteroaryl, or —$C_1$-$C_4$alkyl-(substituted or unsubstituted phenyl); $R^{12}$ is $C_1$-$C_6$alkyl, $C_1$-$C_6$heteroalkyl, $C_1$-$C_6$fluoroalkyl, $C_3$-$C_6$cycloalkyl, a substituted or unsubstituted phenyl, a substituted or unsubstituted naphthyl, a substituted or unsubstituted benzyl, a substituted or unsubstituted 6-membered heteroaryl, or —$C_1$-$C_4$alkyl-(substituted or unsubstituted phenyl); $R^{13}$ is H or $C_1$-$C_4$alkyl; or $R^{12}$ and $R^{13}$ attached to the same N atom are taken together with the N atom to which they are attached to form a substituted or unsubstituted $C_2$-$C_6$heterocycloalkyl.

In some embodiments, $R^4$ is H, F, Cl, Br, —OH, $C_1$-$C_4$alkyl, $C_1$-$C_4$fluoroalkyl, $C_1$-$C_4$fluoroalkoxy, or $C_1$-$C_4$alkoxy.

In some embodiments, $R^{11}$ is $C_1$-$C_6$alkyl, $C_1$-$C_6$haloalkyl, $C_3$-$C_6$cycloalkyl, a substituted or unsubstituted phenyl, or —$C_1$-$C_4$alkyl-(substituted or unsubstituted phenyl).

In some embodiments, $R^4$ is H, F, Cl, Br, —OCH$_3$, —CH$_3$, —CH$_2$CH$_3$, —CHCH$_2$, —CHF$_2$, —CF$_3$, —OCHF$_2$, or —OCF$_3$.

In some embodiments, $R^{12}$ is $C_1$-$C_6$alkyl, $C_1$-$C_6$heteroalkyl, $C_1$-$C_6$fluoroalkyl, $C_3$-$C_6$cycloalkyl, a substituted or unsubstituted phenyl, a substituted or unsubstituted benzyl, or —$C_1$-$C_4$alkyl-(substituted or unsubstituted phenyl); $R^{13}$ is H or —CH$_3$.

In some embodiments, $R^6$ is —$NR^{13}$S(=O)$_2R^{12}$, —N($R^{12}$)($R^{13}$), —C(=O)N($R^{12}$)($R^{13}$), —NHC(=O)N($R^{12}$)($R^{13}$), —$NR^{13}$C(=O)$R^{12}$, or —$NR^{13}$C(=O)O$R^{12}$.

In some embodiments, $R^{11}$ is $C_1$-$C_6$alkyl, $C_1$-$C_6$haloalkyl, a substituted or unsubstituted phenyl, or —$C_1$-$C_4$alkyl-(substituted or unsubstituted phenyl).

In some embodiments, $R^4$ is F, Cl, Br, —OCH$_3$, —CH$_3$, —CH$_2$CH$_3$, —CHCH$_2$, —CHF$_2$, —CF$_3$, —OCHF$_2$, or —OCF$_3$. In some embodiments, $R^4$ is —OCH$_3$.

In some embodiments, $R^6$ is —$NR^{13}$C(=O)$R^{12}$.

In some embodiments, $R^{12}$ is $C_1$-$C_6$alkyl, $C_3$-$C_6$cycloalkyl, a substituted or unsubstituted phenyl, or a substituted or unsubstituted benzyl.

In some embodiments, $R^{11}$ is —CH$_2$CH$_3$, —CH(CH$_3$)$_2$, —C(CH$_3$)$_3$, —CH$_2$CF$_3$, a substituted or unsubstituted phenyl, —$C_1$-$C_2$alkyl-(substituted or unsubstituted phenyl).

In some embodiments, $R^{12}$ is —CH(CH$_3$)$_3$, —C(CH$_3$)$_3$, —CH$_2$CH(CH$_3$)$_2$, —CH$_2$C(CH$_3$)$_3$, cyclopropyl, cyclobutyl, cyclopentyl, cyclohexyl, a substituted or unsubstituted phenyl, or a substituted or unsubstituted benzyl.

In some embodiments, $R^{11}$ is —CH$_2$CH$_3$, —CH(CH$_3$)$_2$, —C(CH$_3$)$_3$, or —CH$_2$CF$_3$; $R^{12}$ is —CH(CH$_3$)$_2$, —C(CH$_3$)$_3$, —CH$_2$CH(CH$_3$)$_2$, —CH$_2$C(CH$_3$)$_3$, or a substituted or unsubstituted phenyl; $R^{13}$ is H.

In some embodiments, $R^4$ is F, Cl, —OCH$_3$, —CF$_3$, or —OCF$_3$; $R^{11}$ is —C(CH$_3$)$_3$; $R^{12}$ is —C(CH$_3$)$_3$; $R^{13}$ is H.

In some embodiments, the DP$_2$ receptor antagonist is {3-[2-tert-butylsulfanylmethyl-4-(2,2-dimethyl-propionylamino)-phenoxy]-4-methoxy-phenyl}-acetic acid, or a pharmaceutically acceptable salt, pharmaceutically acceptable solvate, or prodrug thereof.

In some embodiments, the DP$_2$ receptor antagonist is a compound having the structure of Formula (III), pharmaceutically acceptable salt, pharmaceutically acceptable solvate, N-oxide, or prodrug thereof:

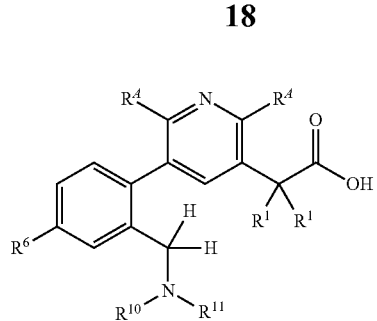

Formula (III)

wherein,
each $R^1$ is independently selected from H and —CH$_3$;
each $R^A$ is independently selected from H, halogen, —CN, —OH, —OR$^{12}$, —N(R$^{13}$)$_2$, $C_1$-$C_6$alkyl, $C_1$-$C_6$fluoroalkyl, $C_1$-$C_6$fluoroalkoxy, $C_1$-$C_6$alkoxy, and $C_1$-$C_6$heteroalkyl.
$R^6$ is selected from halogen, —CN, —NO$_2$, —OH, —OR$^{12}$, —SR$^{12}$, —S(=O)R$^{12}$, —S(=O)$_2$R$^{12}$, —NHS(=O)$_2$R$^{12}$, —N(C$_1$-C$_6$alkyl)S(=O)$_2$R$^{12}$, —S(=O)$_2$N(R$^{13}$)$_2$, —C(=O)R$^{12}$, —OC(=O)R$^{12}$, —CO$_2$R$^{13}$, —OCO$_2$R$^{13}$, —N(R$^{13}$)$_2$, —C(=O)N(R$^{13}$)$_2$, —OC(=O)N(R$^{13}$)$_2$, —NHC(=O)N(R$^{13}$)$_2$, —N(C$_1$-C$_6$alkyl)C(=O)N(R$^{13}$)$_2$, —NHC(=O)R$^{12}$, —N(C$_1$-C$_6$alkyl)C(=O)R$^{12}$, —NHC$_1$-C$_4$alkyl-C(=O)R$^{12}$, —C$_1$-C$_4$alkyl-N(R$^{13}$)$_2$, —C$_1$-C$_4$alkyl-NHC(=O)R$^{12}$, —C$_1$-C$_4$alkyl-NHS(=O)$_2$R$^{12}$, —NHC(=O)OR$^{12}$, —N(C$_1$-C$_6$alkyl)C(=O)OR$^{12}$, $C_1$-$C_6$alkyl, $C_1$-$C_6$fluoroalkyl, $C_1$-$C_6$fluoroalkoxy, $C_1$-$C_6$alkoxy, $C_1$-$C_6$heteroalkyl, a substituted or unsubstituted cycloalkyl, and a substituted or unsubstituted heterocycloalkyl;
$R^{10}$ is —C(=O)R$^{14}$, —C(=O)OR$^{15}$, or —C(=O)N(R$^{16}$)$_2$;
$R^{14}$ is $C_1$-$C_6$alkyl, $C_1$-$C_6$fluoroalkyl, $C_1$-$C_6$heteroalkyl, or a $C_3$-$C_6$cycloalkyl; or
$R^{14}$ is a substituted or unsubstituted aryl, a substituted or unsubstituted heteroaryl, a substituted or unsubstituted —$C_1$-$C_4$alkyl-aryl or a substituted or unsubstituted —$C_1$-$C_4$alkyl-heteroaryl;
$R^{15}$ is $C_1$-$C_6$alkyl, $C_1$-$C_6$fluoroalkyl, $C_1$-$C_6$heteroalkyl, or a $C_3$-$C_6$cycloalkyl; or
$R^{15}$ is a substituted or unsubstituted aryl, a substituted or unsubstituted heteroaryl, a substituted or unsubstituted —$C_1$-$C_4$alkyl-aryl, or a substituted or unsubstituted —$C_1$-$C_4$alkyl-heteroaryl;
each $R^{16}$ is independently H, —CN, $C_1$-$C_6$alkyl, $C_1$-$C_6$fluoroalkyl, $C_1$-$C_6$heteroalkyl, or a $C_3$-$C_6$cycloalkyl; or two $R^{16}$ groups attached to the same N atom are taken together with the N atom to which they are attached to form an optionally substituted heterocycloalkyl; or each $R^{16}$ is independently H, $C_1$-$C_6$alkyl, $C_1$-$C_6$fluoroalkyl, a substituted or unsubstituted aryl, a substituted or unsubstituted heteroaryl, a substituted or unsubstituted —$C_1$-$C_4$alkyl-aryl, or a substituted or unsubstituted —$C_1$-$C_4$alkyl-heteroaryl;
$R^{11}$ is a substituted or unsubstituted aryl, a substituted or unsubstituted heteroaryl, a substituted or unsubstituted —$C_1$-$C_4$alkyl-aryl, or a substituted or unsubstituted —$C_1$-$C_4$alkyl-heteroaryl; or
$R^{11}$ is $C_1$-$C_6$alkyl, $C_1$-$C_6$haloalkyl, or $C_1$-$C_6$heteroalkyl.

In some embodiments, each $R^A$ is H, halogen, —CN, —OH, $C_1$-$C_4$alkyl, $C_1$-$C_4$fluoroalkyl, $C_1$-$C_4$fluoroalkoxy, or $C_1$-$C_4$alkoxy; $R^6$ is H, halogen, —CN, tetrazolyl, —OH, —SR$^{13}$, —S(=O)R$^{12}$, —S(=O)$_2$R$^{12}$, —NHS(=O)$_2$R$^{12}$, —C(=O)R$^{12}$, —OC(=O)R$^{12}$, —CO$_2$R$^{13}$, —N(R$^{13}$)$_2$, —C(=O)N(R$^{13}$)$_2$, —NHC(=O)R$^{12}$, $C_1$-$C_4$alkyl, $C_1$-$C_4$fluoroalkyl, $C_1$-$C_4$fluoroalkoxy, $C_1$-$C_4$alkoxy, or $C_1$-$C_4$heteroalkyl; $R^{10}$ is —C(=O)$C_1$-$C_4$alkyl, —C(=O)$C_1$-$C_4$fluoroalkyl, —C(=O)$C_3$-$C_6$cycloalkyl, —C(=O) (a substituted or unsubstituted phenyl), —C(=O) (a substituted or unsubstituted 6-membered heteroaryl containing 1 or 2 N atom), —C(=O)$C_1$-$C_2$alkyl-(substituted or unsubstituted phenyl), —C(=O)—$C_1$-$C_2$alkyl-(substituted or unsubstituted 6-membered heteroaryl containing 1 or 2 N atom), —C(=O)$C_1$-$C_2$alkyl-O—$C_1$-$C_4$alkyl, —C(=O)—O—$C_1$-$C_4$alkyl, —C(=O)—O—$C_1$-$C_2$alkyl-(substituted or unsubstituted phenyl), —C(=O)—$NR^{16}C_1$-$C_4$alkyl, or —C(=O)—$NR^{16}C_1$-$C_2$alkyl-(substituted or unsubstituted phenyl); $R^{11}$ is $C_1$-$C_4$alkyl, $C_1$-$C_4$haloalkyl, $C_3$-$C_6$cycloalkyl, or substituted or unsubstituted benzyl; $R^{12}$ is $C_1$-$C_4$alkyl, $C_1$-$C_4$heteroalkyl, or $C_1$-$C_4$fluoroalkyl; each $R^{13}$ is independently selected from H, $C_1$-$C_4$alkyl, $C_1$-$C_4$heteroalkyl, $C_1$-$C_4$fluoroalkyl, or substituted or unsubstituted benzyl; $R^{16}$ is H or $C_1$-$C_4$alkyl; where each substituted phenyl or substituted heteroaryl is substituted with 1 or 2 $R^C$, where each $R^C$ is independently selected from halogen, —OH, $C_1$-$C_4$alkyl, $C_1$-$C_4$fluoroalkyl, $C_1$-$C_4$fluoroalkoxy, and $C_1$-$C_4$alkoxy.

In some embodiments, $R^{10}$ is —C(=O)$C_1$-$C_4$alkyl, —C(=O)$C_3$-$C_6$cycloalkyl, —C(=O)$C_1$-$C_2$alkyl-(substituted or unsubstituted phenyl), —C(=O)—$C_1$-$C_2$alkyl-(substituted or unsubstituted 6-membered heteroaryl containing 1 or 2 N atom), —C(=O)—O—$C_1$-$C_2$alkyl-(substituted or unsubstituted phenyl), or —C(=O)—$NR^{16}C_1$-$C_2$alkyl-(substituted or unsubstituted phenyl).

In some embodiments, $R^{10}$ is —C(=O)$C_1$-$C_4$alkyl, —C(=O)$C_3$-$C_6$cycloalkyl, —C(=O)$CH_2$-(substituted or unsubstituted phenyl), —C(=O)—$CH_2$-(substituted or unsubstituted 6-membered heteroaryl containing 1 or 2 N atom), —C(=O)—O—$CH_2$-(substituted or unsubstituted phenyl), or —C(=O)—$NHCH_2$-(substituted or unsubstituted phenyl). In some embodiments, $R^{10}$ is —C(=O)$C_1$-$C_4$alkyl, —C(=O)$C_3$-$C_6$cycloalkyl, —C(=O)$CH_2$-(substituted or unsubstituted phenyl), —C(=O)—O—$CH_2$-(substituted or unsubstituted phenyl), or —C(=O)—$NHCH_2$—(substituted or unsubstituted phenyl). In some embodiments, $R^{10}$ is —C(=O)-β-$CH_2$-(substituted or unsubstituted phenyl). In some embodiments, $R^{10}$ is —C(=O)$CH_3$, —C(=O)$CH_2CH_3$, —C(=O)cyclopropyl, —C(=O)$CH_2OCH_3$, or —C(=O)$CH_2OCH_2CH_3$.

In some embodiments, each $R^A$ is independently selected from H, F, Cl, Br, I, —CN, —OH, —$OCH_3$, —$OCH_2CH_3$, —$CH_3$, —$CH_2CH_3$, —$CF_3$, —$CHF_2$, —$CH_2F$, and —$OCF_3$.

In some embodiments, $R^6$ is H, —$CF_3$, —$CO_2H$, Br, —NH—C(=O)—$CH_3$, —NH—C(=O)—$OCH_3$, —NH—$SO_2CH_3$, —$SCH_3$, —$SO_2CH_3$, —NH—(C=O)—$CH_3$, —NH—$SO_2$—$CH_3$, or —C$(CH_3)_2$—(OH). In some embodiments, $R^6$ is F, Cl, —$CH_3$, —$CF_3$, —$OCF_3$, or —$OCH_3$. In some embodiments, $R^6$ is —$CF_3$.

In some embodiments, $R^{11}$ is $C_1$-$C_6$alkyl. In some embodiments, $R^{11}$ is —$CH_2CH_3$.

In some embodiments, the $DP_2$ receptor antagonist is (5-{2-[(N-benzyloxycarbonyl-N-ethyl-amino)-methyl]-4-trifluoromethyl-phenyl}-pyridin-3-yl)-acetic acid, or a pharmaceutically acceptable salt, pharmaceutically acceptable solvate, or prodrug thereof.

In some embodiments, the $DP_2$ receptor antagonist is a compound having the structure of Formula (IV), pharmaceutically acceptable solvate, pharmaceutically acceptable salt, N-oxide, or prodrug thereof:

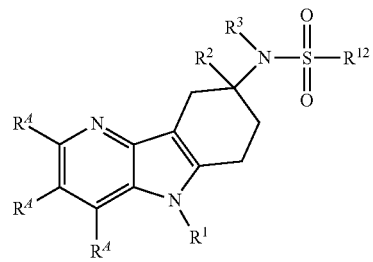

Formula (IV)

wherein, $R^1$ is $L^1$-$X^1$; $L^1$ is $C_1$-$C_6$alkyl; $X^1$ is $CO_2H$, or —$CO_2(C_1$-$C_6$alkyl);

each $R^A$ is independently selected from H, halogen, —CN, —OH, $C_1$-$C_6$alkyl, $C_1$-$C_6$fluoroalkyl, $C_1$-$C_6$fluoroalkoxy, and $C_1$-$C_6$alkoxy;

$R^2$ is H or —$CH_3$;

$R^3$ is H or $C_1$-$C_6$alkyl;

$R^{12}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted aryl, an optionally substituted heteroaryl, an optionally substituted —$C_1$-$C_6$alkyl-cycloalkyl, an optionally substituted —$C_1$-$C_6$alkyl-phenyl, or an optionally substituted —$C_1$-$C_6$alkyl-heteroaryl.

In some embodiments, $R^{12}$ is $C_1$-$C_6$alkyl, an optionally substituted phenyl, an optionally substituted naphthyl, or an optionally substituted heteroaryl containing 0-3 N atoms.

In some embodiments, $R^{12}$ is an optionally substituted phenyl, an optionally substituted naphthyl, an optionally substituted monocyclic heteroaryl containing 0-3 N atoms or an optionally substituted bicyclic heteroaryl containing 0-3 N atoms.

In some embodiments, each $R^A$ is independently selected from H, F, Cl, Br, I, —CN, —OH, —$OCH_3$, —$CH_3$, and —$CF_3$. In some embodiments, each $R^A$ is H.

In some embodiments, $L^1$ is —$CH_2$—, —CH($CH_3$)—, —C$(CH_3)_2$—, or —$CH_2CH_2$—. In some embodiments, $L^1$ is —$CH_2$— or —$CH_2CH_2$—. In some embodiments, $L^1$ is —$CH_2$—. In some embodiments, $L^1$ is —$CH_2CH_2$—.

In some embodiments, $R^{12}$ is a substituted or unsubstituted phenyl, where if $R^{12}$ is substituted then $R^{12}$ is substituted with 1 or 2 groups selected from F, Cl, Br, I, —CN, —$NH_2$, —OH, —NH($CH_3$), —N$(CH_3)_2$, —$CH_3$, —$CF_3$, —$OCH_3$, and —$OCF_3$. In some embodiments, $R^{12}$ is a substituted or unsubstituted phenyl, where if $R^{12}$ is substituted then $R^{12}$ is substituted with 1 group selected from F, Cl, Br, I, —CN, —$NH_2$, —OH, —NH($CH_3$), —N$(CH_3)_2$, —$CH_3$, —$CF_3$, —$OCH_3$, and —$OCF_3$. In some embodiments, $R^{12}$ is 4-fluorophenyl.

In some embodiments, the $DP_2$ receptor antagonist is {8-[(4-fluoro-benzenesulfonyl)-methyl-amino]-6,7,8,9-tetrahydro-pyrido[3,2-b]indol-5-yl}-acetic acid, (R)-{8-[(4-fluoro-benzenesulfonyl)-methyl-amino]-6,7,8,9-tetrahydro-pyrido[3,2-b]indol-5-yl}-acetic acid, (S)-{8-[(4-fluoro-benzenesulfonyl)-methyl-amino]-6,7,8,9-tetrahydro-pyrido[3,2-b]indol-5-yl}-acetic acid, or a pharmaceutically acceptable salt, pharmaceutically acceptable solvate, or prodrug thereof. In some embodiments, the $DP_2$ receptor antagonist is {8-[(4-fluoro-benzenesulfonyl)-methyl-amino]-6,7,8,9-tetrahydro-pyrido[3,2-b]indol-5-yl}-acetic acid, or a pharmaceutically acceptable salt, pharmaceutically acceptable solvate, or prodrug thereof. In some embodiments, the $DP_2$ receptor antagonist is (R)-{8-[(4-fluoro-benzenesulfonyl)-methyl-amino]-6,7,8,9-tetrahydro-pyrido[3,2-b]indol-5-yl}-acetic acid, or a pharmaceutically acceptable salt, pharmaceutically acceptable solvate, or prodrug thereof. In some embodiments, the $DP_2$ receptor antagonist is (S)-{8-[(4-fluoro-benzenesulfonyl)-methyl-amino]-6,7,8,9-tetrahydro-pyrido[3,2-b]indol-5-yl}-acetic acid, or a pharmaceutically acceptable salt, pharmaceutically acceptable solvate, or prodrug thereof.

Any combination of the groups described above for the various variables is contemplated herein. Throughout the specification, groups and substituents thereof are chosen by one skilled in the field to provide stable moieties and compounds.

In some embodiments, the $DP_2$ receptor antagonist compounds are included in the formulations described herein as pharmaceutically acceptable salts, and/or pharmaceutically acceptable solvates. In some embodiments, the $DP_2$ receptor antagonist compounds are included in the formulations described herein as pharmaceutically acceptable salts. In some embodiments, $DP_2$ receptor antagonist compounds are included in the formulations described herein in free acid form or free base form.

In some embodiments, the $DP_2$ receptor antagonist compounds described herein possess one or more stereocenters and each center exists independently in either the R or S configuration. The compounds presented herein include all diastereomeric, enantiomeric, and epimeric forms as well as the appropriate mixtures thereof.

Combination Therapy

In one aspect, pharmaceutical compositions and methods disclosed herein include an additional therapeutic agent. In one aspect, the additional therapeutic agent is a therapeutic agent other than a $DP_2$ receptor antagonist compound.

In one aspect, the ophthalmic pharmaceutical compositions disclosed herein that include a $DP_2$ receptor antagonist compound are co-administered with (either separately or in the same formulation) a therapeutic agent selected from: antibiotics (e.g., polymyxin B sulfate/bacitracin zinc, polymyxin B/neomycin/gramicidin, polymyxin B/trimethoprim, polymyxin B/bacitracin, fluoroquinolones (e.g., ciprofloxacin, moxifloxacin, ofloxacin, gatifloxacin, levofloxacin), aminoglycosides (e.g. tobramycin, azithromycin, gentamicin, erythromycin, bacitracin); anti-Fungal Agents (e.g., amphotericin B, intraconazole, fluconazole, voriconazole); steroid anti-inflammatory agents (e.g., fluorometholone acetate, prednisolone acetate, loteprednol etabonate, prednisolone sodium phosphate, prednisolone sodium, rimexolone, fluorometholone acetate); non-steroidal anti-inflammatory agents (e.g., nepafenac, ketorolac tromethamine, bromfenac, diclofenac sodium, ketorolac tromethamine, ketotifen fumarate); antihistamines (e.g., emedastine difumarate, olopatadine hydrochloride, epinastine HCl, azelastine hydrochloride, ketotifen fumarate); antivirals (e.g., acyclovir, vidarabine, trifluridine); alpha agonists (e.g., apraclonidine, brimonidine, bimatoprost); beta blockers (e.g., betaxolol hydrochloride, levobunolol hydrochloride, carteolol hydrochloride, metipranolol, timolol maleate, timolol hemihydrate); carbonic anhydrase inhibitors (e.g., brinzolamide, dorzolamide, acetazolamide); miotics (e.g., acetylcholine chloride, echothiophate); prostaglandins (e.g., travoprost, bimatoprost, latanoprost); anti-angiogenesis agents (e.g., pegaptanib sodium, ranibizumab, verteporfin); loteprednol etabonate, mast cell stabilizers (e.g., lodoxamide tromethamine, nedocromil sodium, cromolyn sodium, pemirolast potassium), cyclosporine, and leukotriene modulators (e.g. 5-LO inhibitors, FLAP inhibitor compounds, leukotriene receptor antagonist (e.g. $CysLT_1$ receptor antagonists)).

In some embodiments, the ophthalmic pharmaceutical compositions disclosed herein comprising a $DP_2$ receptor antagonist compound are co-administered with (either separately or in the same formulation) an antibiotic. Antibiotics include, but are not limited to polymyxin B sulfate/bacitracin zinc, polymyxin B/neomycin/gramicidin, polymyxin B/trimethoprim, polymyxin B/bacitracin, fluoroquinolones (e.g., ciprofloxacin, moxifloxacin, ofloxacin, gatifloxacin, levofloxacin), aminoglycosides (e.g. tobramycin, azithromycin, gentamicin, erythromycin, bacitracin).

In some embodiments, the ophthalmic pharmaceutical compositions disclosed herein comprising a $DP_2$ receptor antagonist compound are co-administered with (either separately or in the same formulation) an anti-fungal agent. Antifungal agents include, but are not limited to amphotericin B, intraconazole, fluconazole, and voriconazole.

In some embodiments, the ophthalmic pharmaceutical compositions disclosed herein comprising a $DP_2$ receptor antagonist compound are co-administered with (either separately or in the same formulation) a steroid anti-inflammatory agent. Steroid anti-inflammatory agents include but are not limited to, betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In some embodiments, the ophthalmic pharmaceutical compositions disclosed herein comprising a $DP_2$ receptor antagonist compound are co-administered with (either separately or in the same formulation) a non-steroidal anti-inflammatory agent (NSAID). NSAIDs include, but are not limited to, nepafenac, ketorolac, bromfenac, diclofenac, ketorolac, ketotifen.

In some embodiments, the ophthalmic pharmaceutical compositions disclosed herein comprising a $DP_2$ receptor antagonist compound are co-administered with (either separately or in the same formulation) an antihistamine. In some embodiments, antihistamines include, but are not limited to, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine, and triprolidine. In some embodiments, antihistamines include, but are not limited to, emedastine, olopatadine, epinastine, azelastine, ketotifen.

In some embodiments, the ophthalmic pharmaceutical compositions disclosed herein comprising a $DP_2$ receptor antagonist compound are co-administered with (either separately or in the same formulation) an antiviral agent. Antiviral agents include, but are not limited to, acyclovir, vidarabine, trifluridine.

In some embodiments, the ophthalmic pharmaceutical compositions disclosed herein comprising a DP$_2$ receptor antagonist compound are co-administered with (either separately or in the same formulation) and alpha agonist. Alpha agonists include, but are not limited to, apraclonidine, brimonidine, bimatoprost.

In some embodiments, the ophthalmic pharmaceutical compositions disclosed herein comprising a DP$_2$ receptor antagonist compound are co-administered with (either separately or in the same formulation) a beta blocker. Beta blockers include, but are not limited to, betaxolol, levobunolol, carteolol, metipranolol, timolol.

In some embodiments, the ophthalmic pharmaceutical compositions disclosed herein comprising a DP$_2$ receptor antagonist compound are co-administered with (either separately or in the same formulation) a carbonic anhydrase inhibitor. Carbonic anhydrase inhibitors include, but are not limited to, brinzolamide, dorzolamide, acetazolamide.

In some embodiments, the ophthalmic pharmaceutical compositions disclosed herein comprising a DP$_2$ receptor antagonist compound are co-administered with (either separately or in the same formulation) a miotic. Miotics include, but are not limited to, acetylcholine chloride, echothiophate.

In some embodiments, the ophthalmic pharmaceutical compositions disclosed herein comprising a DP$_2$ receptor antagonist compound are co-administered with (either separately or in the same formulation) a prostaglandin. Prostaglandins include, but are not limited to, travoprost, bimatoprost, latanoprost.

In some embodiments, the ophthalmic pharmaceutical compositions disclosed herein comprising a DP$_2$ receptor antagonist compound are co-administered with (either separately or in the same formulation) an anti-angiogenesis agent. Anti-angiogenesis agents include, but are not limited to, pegaptanib sodium, ranibizumab, verteporfin.

In some embodiments, the ophthalmic pharmaceutical compositions disclosed herein comprising a DP$_2$ receptor antagonist compound are co-administered with (either separately or in the same formulation) loteprednol etabonate.

In some embodiments, the ophthalmic pharmaceutical compositions disclosed herein comprising a DP$_2$ receptor antagonist compound are co-administered with (either separately or in the same formulation) a mast cell stabilizer. Mast cell stabilizers include, but are not limited to, lodoxamide tromethamine, nedocromil sodium, cromolyn sodium, pemirolast potassium.

In some embodiments, the ophthalmic pharmaceutical compositions disclosed herein comprising a DP$_2$ receptor antagonist compound are co-administered with (either separately or in the same formulation) cyclosporine.

In some embodiments, the ophthalmic pharmaceutical compositions disclosed herein comprising a DP$_2$ receptor antagonist compound are co-administered with (either separately or in the same formulation) a leukotriene modulator. Leukotriene modulators include, but are not limited to 5-lipoxygenase (5-LO) inhibitors inhibitors, 5-lipoxygenase activating protein (FLAP) inhibitor compounds and leukotriene receptor antagonist (e.g. CysLT$_1$ receptor antagonists).

In some embodiments, the second therapeutic agent is a leukotriene receptor antagonist selected from CysLT$_1$/CysLT$_2$ dual receptor antagonists, and CysLT$_1$ receptor antagonists. CysLT$_1$ receptor antagonists include, but are not limited to, zafirlukast, montelukast, prankulast, and derivatives or analogs thereof.

In some embodiments, the second therapeutic agent is a 5-LO inhibitor. 5-LO inhibitors include, but are not limited to zileuton.

In some embodiments, the second therapeutic agent is a FLAP inhibitor compound. In some embodiments, the FLAP inhibitor is selected from compounds described in U.S. patent application Ser. No. 11/538,762 (issued as U.S. Pat. No. 7,405,302); U.S. patent application Ser. No. 12/131,828; U.S. patent application Ser. No. 11/553,946 (published as 2007/0105866); U.S. patent application Ser. No. 11/925,841; U.S. patent application Ser. No. 12/089,706; U.S. patent application Ser. No. 12/089,707; U.S. patent application Ser. No. 12/092,570; U.S. patent application Ser. No. 11/744,555 (published as 2007/0219206); U.S. patent application Ser. No. 11/746,010 (published as 2007/0225285); U.S. patent application No. 11/745,387 (published as 2007/0244128); U.S. patent application Ser. No. 12/257,876; U.S. patent application No. 61/055,887; U.S. patent application No. 61/055,899; International Patent Application No. PCT/US07/86188; WO 07/047,207; WO07/056,021; WO07/056,220; WO07/056,228; International Patent Application No. PCT/US08/62310; International Patent Application No. PCT/US08/062,793; International Patent Application No. PCT/US08/62580; International Patent Application No. PCT/US2008/052960; International Patent Application No. PCT/US08/81190; International Patent Application No. PCT/US08/76225; each of which is herein incorporated by reference in its entirety.

In some embodiments, the second therapeutic agent is a FLAP inhibitor selected from: MK886 (also known as 3-[3-tert-butylsulfanyl-1-(4-chloro-benzyl)-5-isopropyl-1H-indol-2-yl]-2,2-dimethyl-propionic acid); MK591 (also known as 3-[3-tert-butylsulfanyl-1-(4-chloro-benzyl)-5-(quinolin-2-ylmethoxy)-1H-indol-2-yl]-2,2-dimethyl-propionic acid); and DG031 (also known as BAY X1005; cyclopentyl-[4-(quinolin-2-ylmethoxy)-phenyl]-acetic acid), Compound A (3-[3-tert-Butylsulfanyl-1-[4-(5-methoxy-pyrimidin-2-yl)-benzyl]-5-(5-methyl-pyridin-2-ylmethoxy)-1H-indol-2-yl]-2,2-dimethyl-propionic acid); Compound B (3-[3-tert-Butylsulfanyl-1-[4-(5-methoxy-pyrimidin-2-yl)-benzyl]-5-(5-methyl-pyrazin-2-ylmethoxy)-1H-indol-2-yl]-2,2-dimethyl-propionic acid); Compound C (3-{5-((S)-1-Acetyl-2,3-dihydro-1H-indol-2-ylmethoxy)-3-tert-butylsulfanyl-1-[4-(5-methoxy-pyrimidin-2-yl)-benzyl]-1H-indol-2-yl}-2,2-dimethyl-propionic acid); Compound D (3-[3-tert-Butylsulfanyl-1-[4-(6-methoxy-pyridin-3-yl)-benzyl]-5-(pyridin-2-ylmethoxy)-1H-indol-2-yl]-2,2-dimethyl-propionic acid); Compound E (3-[3-tert-Butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid); Compound F (3-[3-tert-Butylsulfanyl-1-[4-(5-fluoro-pyridin-2-yl)-benzyl]-5-(quinolin-2-ylmethoxy)-1H-indol-2-yl]-2,2-dimethyl-propionic acid); Compound G (2-[3-tert-Butylsulfanyl-1-[4-(5-methoxy-pyrimidin-2-yl)-benzyl]-5-(5-methyl-pyridin-2-ylmethoxy)-1H-indol-2-ylmethyl]-2-ethyl-butyric acid); Compound H (3-[3-tert-Butylsulfanyl-1-[4-(6-methoxy-pyridin-3-yl)-benzyl]-5-(5-methyl-pyridin-2-ylmethoxy)-1H-indol-2-yl]-2,2-dimethyl-propionic acid); Compound I (3-[5-((S)-1-Acetyl-pyrrolidin-2-ylmethoxy)-3-tert-butylsulfanyl-1-(4-chloro-benzyl)-1H-indol-2-yl]-2,2-dimethyl-propionic acid); and Compound J (3-[3-tert-butylsulfanyl-1-[4-(5-fluoro-pyridin-2-yl)-benzyl]-5-(pyridin-2-ylmethoxy)-1H-indol-2-yl]-2,2-dimethyl-propionic acid), Compound K (3-{5-((S)-1-Acetyl-2,3-dihydro-1H-indol-2-ylmethoxy)-3-tert-butylsulfanyl-1-[4-(5-ethoxy-pyrimidin-2-yl)-benzyl]-1H-indol-2-yl}-2,2-dimethyl-propionic acid), or pharmaceutically acceptable salt or N-oxide thereof.

In some embodiments, the second therapeutic agent is a FLAP inhibitor selected from compounds described in U.S. Pat. Nos. 4,929,626; 4,970,215; 5,081,138; 5,095,031; 5,204, 344; 5,126,354; 5,221,678; 5,229,516; 5,272,145; 5,283,252; 5,288,743; 5,292,769; 5,304,563; 5,399,699; 5,459,150; 5,512,581; 5,597,833; 5,668,146; 5,668,150; 5,691,351; 5,714,488; 5,783,586; 5,795,900; and 5,843,968, each of which is herein incorporated by reference for the disclosure of such FLAP inhibitors).

In one aspect, the $DP_2$ receptor antagonist compound described herein is used in combination with a second therapeutic agent compound for the treatment of any ophthalmic disease or condition described herein. In some embodiments, the ratio of the amount of the $DP_2$ receptor antagonist to the second therapeutic agent compound in any ophthalmic pharmaceutical composition described herein is from about 20:1 to about 1:20. In some instances, the ratio of the amount of the $DP_2$ receptor antagonist compound to the second therapeutic agent compound in any ophthalmic pharmaceutical composition described herein is about 20:1, about 15:1, 10:1, about 8:1, about 6:1, about 5:1, about 4:1, about 2:1, about 1:1, about 1:2, about 1:4, about 1:5, about 1:6, about 1:8, about 1:10, about 1:15, or about 1:20.

In some embodiments, the $DP_2$ receptor antagonist compound and the additional therapeutic agent are in the same pharmaceutical composition. In some embodiments, the $DP_2$ receptor antagonist compound and the additional therapeutic agent are in separate pharmaceutical compositions. In some embodiments, the $DP_2$ receptor antagonist compound and the additional therapeutic agent are administered at the same time. In some embodiments, the $DP_2$ receptor antagonist compound and the additional therapeutic agent are administered at different times.

Further Forms of Compounds

In some embodiments, the therapeutic agent(s) (e.g. DP2 receptor antagonist and/or second therapeutic agent) is present in the ophthalmic pharmaceutical composition as a pharmaceutically acceptable salt. In some embodiments, pharmaceutically acceptable salts are obtained by reacting the therapeutic agent(s) with an acid. In some other embodiments, pharmaceutically acceptable salts are obtained by reacting the therapeutic agent(s) with a base. In some embodiments, the therapeutic agents are used as pharmaceutically acceptable salts in the preparation of the opthalmic pharmaceutical compositions described herein. In other embodiments, the therapeutic agents are used as free-acid or free-base form in the manufacture of the ophthalmic pharmaceutical compositions described herein. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, the therapuetic agent(s) is/are reacted with an organic base, such as, but not limited to, ethanolamine, diethanolamine, triethanolamine, tromethamine, N-methylglucamine, dicyclohexylamine, tris(hydroxymethyl)methylamine. In other cases, the therapeutic agent(s) form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like. In some embodiments, a pharmaceutically acceptable salt of a compound disclosed herein is a sodium salt.

In some embodiments, the therapeutic agents disclosed herein possess one or more stereocenters and each center exists independently in either the R or S configuration. The compounds presented herein include all diastereomeric, enantiomeric, and epimeric forms as well as the appropriate mixtures thereof.

In some embodiments, sites on the therapeutics agents disclosed herein are susceptible to various metabolic reactions Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

In some embodiments, the compounds described herein are labeled isotopically (e.g. with a radioisotope) or by another other means, including, but not limited to, the use of chromophores or fluorescent moieties, bioluminescent labels, or chemiluminescent labels. In some embodiments, compounds described herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. In this application, the use of "or" or "and" means "and/or" unless stated otherwise. Furthermore, use of the term "including" as well as other forms, such as "include", "includes," and "included," is not limiting.

"Alkoxy" refers to (alkyl)O—, where alkyl is as defined herein.

"Alkyl" refers to an aliphatic hydrocarbon group. The alkyl may be saturated or unsaturated. In one aspect, alkyl groups are selected from methyl, ethyl, propyl, iso-propyl, n-butyl, iso-butyl, sec-butyl, and t-butyl.

"Cycloalkyl" refers to a monocyclic aliphatic, non-aromatic radical, wherein each of the atoms forming the ring (i.e. skeletal atoms) is a carbon atom. Cycloalkyl groups include, for example, cyclopropyl, cyclobutyl, cyclopentyl, and cyclohexyl.

"Halo", "halogen" or "halide" means fluoro, chloro, bromo or iodo.

"Fluoroalkyl" refers to an alkyl in which one or more hydrogen atoms are replaced by a fluorine atom. In one aspect, a fluoroalkyl is selected from —$CF_3$, —$CHF_2$, —$CH_2F$, —$CH_2CF_3$ and —$CF_2CF_3$.

"Fluoroalkoxy" refers to (fluoroalkyl)O—, where fluoroalkyl is as defined herein.

"Heteroalkyl" refers to an alkyl group in which one or more skeletal atoms of the alkyl are selected from an atom other than carbon, e.g., oxygen, nitrogen (e.g. NH or Nalkyl), sulfur, or combinations thereof. In one aspect, heteroalkyl refers to an alkyl group in which one of the skeletal atoms of the alkyl is oxygen, nitrogen, or sulfur. In another aspect, heteroalkyl refers to an alkyl group in which one of the skeletal atoms of the alkyl is oxygen.

"6-Membered heteroaryl" includes pyridinyl, pyridazinyl, pyrimidinyl, pyrazinyl and triazinyl.

"Aryl" refers to phenyl or naphthalenyl. In some embodiments, an aryl is a phenyl.

The term "haloalkyl" refers to an alkyl group in which one or more hydrogen atoms are replaced by one or more halide atoms. In one aspect, a haloalkyl is a $C_1$-$C_4$haloalkyl.

The terms "heteroaryl" or, alternatively, "heteroaromatic" refers to an aryl group that includes one or more ring heteroatoms selected from nitrogen, oxygen and sulfur. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. In one aspect, the heteroaryl is a $C_1$-$C_{10}$heteroaryl. In another aspect, the heteroaryl is a $C_2$-$C_9$heteroaryl. In some cases, the heteroaryl includes at least one N atom in the ring. In some cases, the heteroaryl includes 1 or 2 N atom in the ring. In some cases, the heteroaryl includes 1 to 4 heteroatoms in the ring selected from O, N, and S. In one aspect, monocyclic heteroaryl is a $C_1$-$C_5$heteroaryl. In one aspect, bicyclic heteroaryl is a $C_5$-$C_{10}$heteroaryl.

A "heterocycloalkyl" or "heteroalicyclic" group refers to a cycloalkyl group that includes at least one heteroatom selected from nitrogen, oxygen and sulfur. Examples of heterocycloalkyl groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl includes 1 or 2 heteroatoms in the ring selected from O, S, and N.

The term "optionally substituted" or "substituted" means that the referenced group may be substituted with one or more additional group(s) individually and independently selected from halogen, —OH, —CN, $C_1$-$C_4$alkyl, $C_1$-$C_4$fluoroalkyl, $C_1$-$C_4$alkoxy, $C_1$-$C_4$fluoroalkoxy, —$NH_2$, —NH($C_1$-$C_4$alkyl), —N($C_1$-$C_4$alkyl)$_2$, and $C_1$-$C_4$heteroalkyl. In some cases, substituted groups are substituted with one or more substituents selected from halogen, —OH, —O$C_1$-$C_4$alkyl, $C_1$-$C_4$alkyl, $C_1$-$C_4$heteroalkyl, $C_1$-$C_4$fluoroalkyl and —O$C_1$-$C_4$fluoroalkyl. For example, in some embodiments, a referenced substituted group is substituted with at least one group selected from halogen, —OH, —CN, —$CH_3$, —$CH_2CH_3$, —$CF_3$, —$OCH_3$, —$OCH_2CH_3$, and —$OCF_3$. In some cases, the referenced substituted group is substituted with 1 or 2 of the aforementioned groups.

"Prodrug" refers to an agent that is converted into the parent drug in vivo. In some situations, prodrugs are often useful because they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of carboxylic acid containing compound which is administered as an ester (the "prodrug") and then is metabolically hydrolyzed to the carboxylic acid. In some embodiments, a prodrug is an alkyl ester prodrug. In some embodiments, a prodrug is a $C_1$-$C_4$alkyl ester prodrug. In some embodiments, a prodrug is a methyl ester or ethyl ester prodrug. A further example of a prodrug might be a short peptide (polyaminoacid) bonded to an acid group where the peptide is metabolized to reveal the active moiety. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. In certain embodiments, the prodrug of a compound described herein is bioavailable by oral administration whereas the parent is not. Furthermore, in some embodiments, the prodrug of a compound described herein has improved solubility in pharmaceutical compositions over the parent drug. Prodrug forms of the herein described compounds, wherein the prodrug is metabolized in vivo to produce a derivative as set forth herein are included within the scope of the claims. Indeed, some of the herein-described compounds are a prodrug for another derivative or active compound.

The terms "individual," "patient," or "subject" are used interchangeably. As used herein, "individual," "patient," or "subject" mean any mammal. In some embodiments, the mammal is a human. In some embodiments, the mammal is a non-human primate such as chimpanzee, and other apes and monkey species. In some embodiments, the mammal is a farm animal such as cattle, horse, sheep, goat, or swine. In some embodiments, the mammal is a domestic animal such as rabbit, dog, or cat. In some embodiments, the mammal is a laboratory animal, including rodents, such as rats, mice and guinea pigs, and the like.

The terms "treat," "treating" or "treatment," and other grammatical equivalents as used herein, include alleviating, abating, inhibiting, reducing, ameliorating, delaying the onset of, arresting the progression of, and/or inducing the regression of a disorder, disease or condition and/or the symptoms of the disorder, disease or condition. The terms also include prophylactic treatment of a disorder, disease or condition. The terms further include achieving any therapeutic benefit. Therapeutic benefit means the eradication or amelioration of the underlying disorder, disease or condition being treated, and/or the eradication or amelioration of one or more of the physiological symptoms associated with the underlying disorder, disease or condition such that an improvement is observed in the individual.

The terms "prevent," "preventing" or "prevention," and other grammatical equivalents as used herein include inhibiting (arresting or stopping) the development of a disorder, disease or condition, and/or inhibiting (arresting or stopping) the further progression of a disorder, disease or condition. These terms are intended to include prophylaxis. For prophylactic benefit, a formulation disclosed herein is administered to an individual at risk of developing a particular disorder, disease or condition, or to an individual reporting one or more of the physiological symptoms of a disorder, disease or condition, or to an individual at risk of reoccurrence of the disorder, disease or condition.

The terms "effective amount" or "therapeutically effective amount" as used herein, refer to an amount of an agent (e.g. $DP_2$ receptor antagonist compound) being administered which achieves a desired result, e.g., to relieve to some extent one or more symptoms of a disease, disorder or condition being treated. In certain instances, the result is a reduction and/or alleviation of at least one sign, symptom, or cause of a disease, or any other desired alteration of a biological system.

The terms "administer," "administering," "administration," and the like, as used herein, refer to the methods that are used to enable delivery of $DP_2$ receptor antagonists to the desired site of biological action (e.g., the site of an ophthalmic disease or condition). These methods include any suitable method for topical administration of a $DP_2$ receptor antagonist compound to an eye.

"Ophthalmic pharmaceutical composition" as used herein refers to a pharmaceutical composition that is in a form suitable for administration to the eye of a mammal. Unless otherwise noted, ophthalmic pharmaceutical composition comprises a $DP_2$ receptor antagonist.

The term "eye" as used herein, includes without limitation, the outer surface and the interior of the eye, the blood vessels in contact with the eye, the orbit and socket of the eye, the epidermal surface and tissues that surround the eye, the eyelid, eyelashes, and fatty deposits surrounding the eye.

Ophthalmic Pharmaceutical Compositions

In some embodiments, an ophthalmic pharmaceutical composition disclosed herein facilitates the delivery of a $DP_2$ receptor antagonist compound to the eye, or a tissue related thereto, for a local effect in ocular tissues (i.e., an effect that is limited to the eye or a tissue related thereto). In certain instances, local administration of a $DP_2$ receptor antagonist compound reduces or eliminates side-effects that are associated with systemic administration of a $DP_2$ receptor antagonist.

In some embodiments, a $DP_2$ receptor antagonist is formulated as an ophthalmic pharmaceutical composition for administration to an eye of a mammal. In some embodiments, the ophthalmic pharmaceutical composition is formulated as a solution, a suspension (e.g., an aqueous suspension), an ointment, a gel, a cream, a liposome, a niosome, a pharmacosome, a nanoparticle, or combinations thereof. In some embodiments, the ophthalmic pharmaceutical composition is administered to the eye of a mammal via implantation, insertion (e.g., via an insoluble insert or a soluble insert), injection, spraying, washing, or combinations thereof.

In some embodiments, the ophthalmic pharmaceutical composition comprising a $DP_2$ receptor antagonist is formulated as a solution, suspension, cream, lotion, ointment, and/or gel. In one embodiment, the ophthalmic pharmaceutical composition is administered as eye drops that are applied to an eye (or a tissue related thereto) of a mammal. In one embodiment, the ophthalmic pharmaceutical composition is administered to the eye of a mammal as an eye wash that can be applied on an eye (or a tissue related thereto) of a mammal, including a human.

Solutions and Suspensions

In some embodiments, the ophthalmic pharmaceutical composition disclosed herein is in the form of a solution that is suitable for administration to the eye of a mammal. In some embodiments, the ophthalmic pharmaceutical composition disclosed herein is in the form of a suspension that is suitable for administration to the eye of a mammal. In certain instances, an ophthalmic solution or suspension also rehydrates the ocular tissues and is thus especially useful for the treatment or prevention of ophthalmic diseases or conditions characterized by loss or reduction of hydration.

Creams and Lotions

In some embodiments, the ophthalmic pharmaceutical composition disclosed herein is in the form of a cream that is suitable for administration to the eye of a mammal. In certain instances, creams are semisolid (e.g., soft solid or thick liquid) formulations that include a $DP_2$ receptor antagonist compound dispersed in an oil-in-water emulsion or a water-in-oil emulsion. In some embodiments, the ophthalmic pharmaceutical composition disclosed herein is in the form of a lotion that is suitable for administration to the eye of a mammal. In certain instances, lotions are fluid emulsions (e.g., oil-in-water emulsions or water-in-oil emulsions). In some embodiments, the ophthalmic lotion or cream comprises a hydrophobic component. In some embodiments, the hydrophobic component of the lotion or cream is from an animal (e.g., lanolin, cod liver oil, and ambergris), from a plant (e.g., safflower oil, castor oil, coconut oil, cottonseed oil, menhaden oil, palm kernel oil, palm oil, peanut oil, soybean oil, rapeseed oil, linseed oil, rice bran oil, pine oil, sesame oil, or sunflower seed oil), or petroleum (e.g., mineral oil, or petroleum jelly).

In certain instances, lotions and creams have a "drying" effect in ophthalmic diseases or conditions (e.g., some or all fluid exuded from an eye and/or a tissue related thereto is miscible in the ointment) and are thus useful for ophthalmic diseases or conditions characterized by the exudation of fluids.

Ointments

In some embodiments, the ophthalmic pharmaceutical composition disclosed herein is in the form of an ointment that is suitable for administration to the eye of a mammal. In certain instances, ointments are semisolid preparations that soften or melt at body temperature (including the temperature of an eye and/or a tissue related thereto). In certain instances, ointments re-hydrate a tissue and are thus useful for ophthalmic diseases or conditions characterized by loss of moisture.

Gels

In some embodiments, the ophthalmic pharmaceutical composition disclosed herein is in the form of a gel that is suitable for administration to the eye of a mammal. In certain instances, gels are semisolid (or semi-rigid) systems consisting of dispersions of large organic molecules dispersed in a liquid. In certain instances, gels are water-soluble and are removed using warm water or saline. In certain instances, gels re-hydrate tissues and are thus useful for ophthalmic diseases or conditions characterized by loss of moisture.

Ocular-Acceptable Delivery Devices

In some embodiments, the ophthalmic pharmaceutical compositions disclosed herein are administered to the eye of a mammal via a device that can be inserted between an eye and eyelid or in the conjunctival sac, where the device releases the ophthalmic pharmaceutical composition comprising the $DP_2$ antagonist compound. In some embodiments, the ophthalmic pharmaceutical composition is released into the lacrimal fluid that bathes the surface of the cornea, or directly to the cornea itself, with which the solid article is generally in intimate contact. Any suitable device in used with the ophthalmic pharmaceutical compositions disclosed herein and methods disclosed herein (e.g., an eyegate applicator).

Ocular-Acceptable Injectable Depot Preparations

In some embodiments, ophthalmic pharmaceutical compositions are administered via an injectable depot preparation. As used herein, a depot preparation is a controlled-release formulation that is injected in the eye of a mammmal or a tissue related thereto (e.g., the sclera). For example, depot preparation is injected subcutaneously, intramuscularly, intravitreally, or within the subconjunctiva. The ratio of $DP_2$ receptor antagonist to controlled-release matrix and the nature of the matrix employed control the rate of drug release.

In some embodiments, a depot preparation is formulated by forming microencapsulated matrices (also known as microencapsule matrices) of a $DP_2$ receptor antagonist in biodegradable polymers. In some embodiments, a depot preparation is formulated by entrapping a $DP_2$ receptor antagonist in liposomes or microemulsions.

Ocular-Acceptable Excipients

An ophthalmic pharmaceutical composition for administration to an eye has an ophthalmically acceptable tonicity. In certain instances, lacrimal fluid has an isotonicity value equivalent to that of a 0.9% sodium chloride solution. In certain instances, an isotonicity value from about 0.6% to about 1.8% sodium chloride equivalency is suitable for administration to an eye. In certain instances, an ophthalmic pharmaceutical composition for administration to an eye disclosed herein has an osmolarity from about 200 to about 600 mOsm/L. In some embodiments, an ophthalmic pharmaceutical composition for administration to an eye disclosed herein is hypotonic and thus requires the addition of any suitable to attain the proper tonicity range. Ophthalmically acceptable substances that modulate tonicity include, but are not limited to, sodium chloride, potassium chloride, sodium thiosulfate, sodium bisulfite and ammonium sulfate.

An ophthalmic pharmaceutical composition for administration to an eye has an ophthalmically acceptable clarity. In certain instances, a formulation that lacks suitable clarity interferes with the proper functioning of an eye. Examples of ophthalmically-acceptable clarifying agents include, but are not limited to, polysorbate 20, polysorbate 80, and the like.

In some embodiments, an ophthalmic pharmaceutical composition for administration to an eye of a mammal comprises an ophthalmically acceptable viscosity enhancer. In certain instances, a viscosity enhancer increases the time a formulation disclosed herein remains in an eye. In certain instances, increasing the time a formulation disclosed herein remains in the eye allows for greater drug absorption and effect. Non-limiting examples of mucoadhesive polymers include carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, an ophthalmic pharmaceutical composition for administration to an eye is administered or delivered to the posterior segments of an eye (e.g., to the retina, choroid, vitreous and optic nerve). In some embodiments, an ophthalmic pharmaceutical composition for administration to an eye of a mammal comprises a solubilizing agent, for example, a glucan sulfate and/or a cyclodextrin. Glucan sulfates which can be used include, but are not limited to, dextran sulfate, cyclodextrin sulfate and β-1,3-glucan sulfate, both natural and derivatives thereof, or any compound which can temporarily bind to and be retained at tissues which contain fibroblast growth factor (FGF), which improves the stability and/or solubility of a drug, and/or which improves penetration and opthalmic absorption of the ophthalmic pharmaceutical composition. Cyclodextrin derivatives that can be used as a solubilizing agent include, but are not limited to, α-cyclodextrin, β-cyclodextrin, γ-cyclodextrin, hydroxyethyl β-cyclodextrin, hydroxypropyl γ-cyclodextrin, hydroxypropyl β-cyclodextrin, sulfated β-cyclodextrin, sulfated α-cyclodextrin, sulfobutyl ether β-cyclodextrin.

An ophthalmic pharmaceutical composition for administration to an eye of a mammal is formulated in any suitable manner. Any suitable technique, carrier, and/or excipient is contemplated for use with the $DP_2$ receptor antagonist compounds disclosed herein. For a summary of formulations for administration to an eye described herein see Kaur, I. P., Kanwar, M., *Drug Dev Industrial Pharmacy,* 2002, 28, 473-493; Lang, J. C., *Adv Drug Delivery Rev.,* 1995, 16, 39-43; Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), which are herein incorporated by reference for such disclosures.

In some embodiments, any ophthalmic pharmaceutical composition described herein comprises between about 0.1 to about 25%, between about 0.1 to about 20%, between about 0.1 to about 15%, between about 0.1 to about 10%, between about 0.1 to about 5%, or between about 0.1 to about 1% of a $DP_2$ receptor antagonist by weight of the ophthalmic pharmaceutical composition.

Dosing

Disclosed herein, in certain embodiments, is an ophthalmic pharmaceutical composition that is administered to the eye of a mammal to treat or prevent an ophthalmic disease or condition (i.e. prophylactic and/or therapeutic treatments). In certain instances, amounts effective for this use will depend on the severity and course of the disease, disorder or condition, previous therapy, the individual's health status and response to the drugs, and the judgment of the treating physician. In some embodiments, the dose is about 0.001% by weight to about 10% by weight per kg of a mammal.

The compounds described herein are optionally administered to any portion of the eye, generally referred to as "ophthalmic administration." Ophthalmic administration to the eye encompasses, but is not limited to, intraocular injection, subretinal injection, intravitreal injection, periocular administration, subconjuctival injections, retrobulbar injections, intracameral injections (including into the anterior or vitreous chamber), sub-Tenon's injections or implants, ophthalmic solutions, ophthalmic suspensions, ophthalmic ointments, ocular implants and ocular inserts, intraocular solutions, use of iontophoresis, incorporation in surgical irrigating solutions, and packs (by way of example only, a saturated cotton pledget inserted in the formix).

Administration of an ophthalmic pharmaceutical composition disclosed herein generally results in direct contact of a $DP_2$ receptor antagonist compound with the cornea, through which at least a portion of a $DP_2$ receptor antagonist passes. In certain instances, an ophthalmic pharmaceutical composition disclosed herein has an effective residence time in an eye of about 2 to about 24 hours, more typically about 4 to about 24 hours and most typically about 6 to about 24 hours.

Useful ophthalmic pharmaceutical compositions are in the form of an aqueous solution, suspension or solution/suspension, which can be presented in the form of eye drops. A desired dosage can be administered via a set number of drops into an eye. For example, for a drop volume of 25 μl, administration of 1-6 drops will deliver 25-150 μl of the ophthalmic pharmaceutical composition. Aqueous ophthalmic pharmaceutical compositions typically contain from about 0.01% to about 50%, about 0.1% to about 20%, about 0.2% to about 10%, or about 0.5% to about 5%, weight/volume of a $DP_2$ receptor antagonist compound.

In some embodiments, where an ophthalmic disease or condition does not improve, an ophthalmic pharmaceutical composition disclosed herein is administered chronically to the eye of the mammal (i.e., for an extended period of time, including throughout the duration of the individual's life). In some embodiments, where an ophthalmic disease or condition does improve, the ophthalmic pharmaceutical composition is given continuously; alternatively, the dose of $DP_2$ receptor antagonist being administered is temporarily reduced or temporarily suspended for a certain length of time (i.e., a "drug holiday"). In some embodiments, a drug holiday lasts between 2 days and 1 year, including all integers in between. In some embodiments, the dose reduction during a drug holiday is from about 10% to about 100%, including all integers in between.

In some embodiments, where an ophthalmic disease or condition does improve, the ophthalmic pharmaceutical composition is administered as a maintenance dose. In some embodiments, where an ophthalmic disease or condition does improve, the ophthalmic pharmaceutical composition is administered with reduced frequency or at a reduced dose.

In one embodiment, the ophthalmic pharmaceutical composition is formulated for immediate release of a $DP_2$ receptor antagonist compound. In some embodiments, a $DP_2$ receptor antagonist is released immediately from the ophthalmic pharmaceutical composition, or within 1 minute, or within 5 minutes, or within 10 minutes, or within 15 minutes, or within 30 minutes, or within 60 minutes or within 90 minutes.

In one embodiment, the ophthalmic pharmaceutical composition is formulated for delayed (or controlled) release of a $DP_2$ receptor antagonist. In some embodiments, a $DP_2$ receptor antagonist compound is released from the ophthalmic pharmaceutical composition over a time period exceeding 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

EXAMPLES

These examples are provided for illustrative purposes only and not to limit the scope of the claims provided herein.

Example 1

Synthesis of [2'-[(Cyclopropanecarbonyl-ethyl-amino)-methyl]-4'-(6-ethoxy-pyridin-3-yl)-6-methoxy-biphenyl-3-yl]-acetic acid

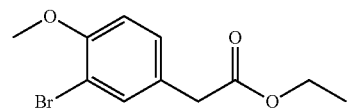

Step 1: (3-Bromo-4-methoxy-phenyl)-acetic acid ethyl ester

To (3-bromo-4-methoxy-phenyl)-acetic acid (24 g, 97.9 mmol) in ethanol (240 mL) was added thionyl chloride (78 mL, 107.7 mmol) and the reaction was stirred at room temperature for 1.5 hours. Once no starting material was seen by analytical LCMS, saturated $NaHCO_3$ (aq.) was added until the reaction was basic. The mixture was extracted twice with dichloromethane and the combined organic layers were washed with water, dried over magnesium sulfate, filtered, and concentrated to give the title compound.

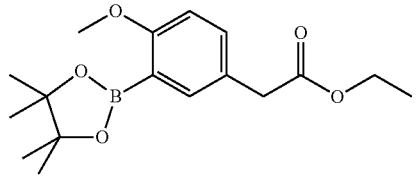 [SMILES: CCOC(=O)Cc1ccc(OC)c(B2OC(C)(C)C(C)(C)O2)c1]

Step 2: [4-Methoxy-3-(4,4,5,5-tetramethyl-[1,3,2] dioxaborolan-2-yl)-phenyl]-acetic acid ethyl ester (3-Bromo-4-methoxy-phenyl)-acetic acid ethyl ester (27.4 g, 100.3 mmol), bis(pinacolato)diboron (25.47 g, 100.3 mmol), and potassium acetate (24.6 g, 250.8 mmol) were combined in 1,4-dioxane (250 mL) under nitrogen. The solution was purged with nitrogen, and then (1,1'-bis(diphenylphosphino)ferrocene)-dichloropalladium(II) (4.10 g, 5.02 mmol) was added and the reaction was heated to 110° C. overnight. The mixture was filtered through Celite and partitioned between EtOAc and brine. The aqueous layer was separated and extracted twice with EtOAc, and the combined organic layers were dried and concentrated. The residue was purified by silica gel chromatography (20-60% EtOAc in hexanes) to give the title compound.

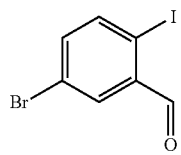

Step 3: 5-Bromo-2-iodobenzaldehyde

To 5-bromo-2-iodobenzonitrile (7.49 g, 24.2 mmol) in tetrahydrofuran (40 mL) at −78° C. was added diisobutylaluminum hydride (1.0M in hexanes; 24.2 mL, 24.2 mmol) over 5 minutes, and the reaction was allowed to warm to room temperature and monitored by analytical TLC. After stirring overnight at room temperature, starting material was still present, so the mixture was cooled to 0° C. and additional diisobutylaluminum hydride (1.0M in hexanes; 10.0 mL, 10.0 mmol) was added. After stirring for 2 hours at room temperature, no starting material was seen by analytical TLC, so the mixture was carefully quenched with freshly saturated aqueous sodium sulfate and diluted with ethyl acetate. The mixture was stirred vigorously for 1 hour and then filtered through Celite. The filtrate was concentrated, and the resulting oil solidified on standing. The solid was stirred vigorously in dichloromethane and 1N aqueous hydrochloric acid, and the aqueous layer was separated and extracted with dichloromethane. The combined organic layers were dried over magnesium sulfate, filtered, and concentrated to give the title compound.

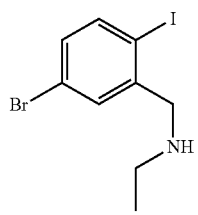

Step 4: (5-Bromo-2-iodo-benzyl)-ethyl-amine

To 5-bromo-2-iodo-benzaldehyde (5.0 g, 16.1 mmol) in methanol (20 mL) was added ethylamine (2M in methanol; 16 mL, 24.0 mmol), followed by acetic acid (1.0 mL, 17.8 mmol), and the mixture was stirred at room temperature for 30 minutes. Sodium cyanoborohydride (2.0 g, 31.8 mmol) was then added over 5 minutes, and the reaction was stirred at room temperature over the weekend. The mixture was concentrated and partitioned between ethyl acetate and saturated aqueous sodium bicarbonate. The aqueous layer was extracted with ethyl acetate, and the combined organic layers were dried over magnesium sulfate, filtered, and concentrated. The residue was purified by silica gel chromatography (0-5% methanol in dichloromethane) to give the title compound.

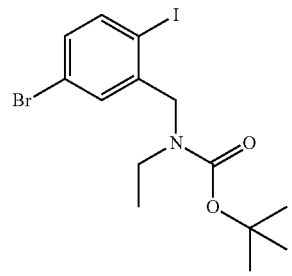 [SMILES: CCN(Cc1cc(Br)ccc1I)C(=O)OC(C)(C)C]

Step 5: (5-Bromo-2-iodo-benzyl)-ethyl-carbamic acid tert-butyl ester (5-Bromo-2-iodo-benzyl)-ethyl-amine (4.05 g, 11.9 mmol) in dichloromethane (30 mL) was treated with di-tert-butyl dicarbonate (3.12 g, 14.3 mmol) at room temperature overnight. The mixture was diluted with dichloromethane, washed with water and brine, and dried over magnesium sulfate then filtered and concentrated to give the title compound.

Step 6: {4'-Bromo-2'-[(tert-butoxycarbonyl-ethyl-amino)-methyl]-6-methoxy-biphenyl-3-yl}-acetic acid ethyl ester (5-Bromo-2-iodo-benzyl)-ethyl-carbamic acid tert-butyl ester (2.0 g, 4.54 mmol), [4-methoxy-3-(4,4,5,5-tetramethyl-[1,3,2]dioxaborolan-2-yl)-phenyl]-acetic acid ethyl ester (1.67 g, 5.21 mmol), and potassium carbonate (1.57 g, 11.4 mmol) were combined in DME:H$_2$O (2:1) under nitrogen. The mixture was purged with nitrogen, and then tetrakis(triphenylphosphine)palladium(0) (0.150 g, 0.13 mmol) was added, and the reaction was heated to 80° C. for 36 hours. Once no starting material was seen by analytical LCMS, the mixture was cooled to room temperature and diluted with dichloromethane and water. The aqueous layer was separated and extracted with dichloromethane, and the combined organic layers were dried over magnesium sulfate, filtered, and concentrated. The residue was purified by silica gel chromatography (0-100% ethyl acetate in hexanes) to give the title compound.

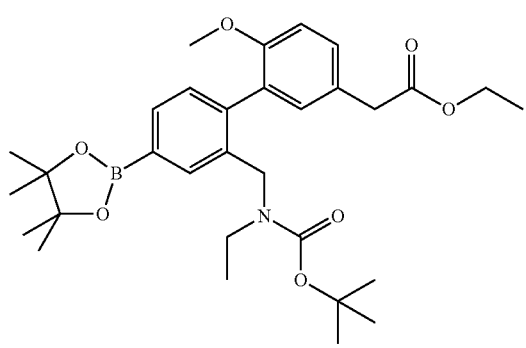 [SMILES: CCOC(=O)Cc1ccc(OC)c(-c2ccc(B3OC(C)(C)C(C)(C)O3)cc2CN(CC)C(=O)OC(C)(C)C)c1]

Step 7: [2'-[(tert-Butoxycarbonyl-ethyl-amino)-methyl]-6-methoxy-4'-(4,4,5,5-tetramethyl-[1,3,2]dioxaborolan-2-yl)-biphenyl-3-yl]-acetic acid ethyl ester {4'-Bromo-2'-[(tert-butoxycarbonyl-ethyl-amino)-methyl]-6-methoxy-biphenyl-3-yl}-acetic acid ethyl ester (1.55 g, 3.06 mmol), bis(pinacolato)diboron (1.0 g, 3.9 mmol), and potassium acetate (0.901 g, 6.5 mmol) were combined in 1,4-dioxane (12 mL) under N₂. The solution was purged with nitrogen, and then (1,1'-bis(diphenylphosphino)ferrocene-dichloropalladium(II) (0.125 g, 0.15 mmol) was added and the reaction was heated to 55° C. overnight. The reaction was monitored by analytical LCMS and upon completion the mixture was filtered through Celite and partitioned between ethyl acetate and brine. The aqueous layer was separated and extracted twice with ethyl acetate, and the combined organic layers were dried and concentrated. The residue was purified by silica gel chromatography (ethyl acetate in hexanes gradient) to give the title compound.

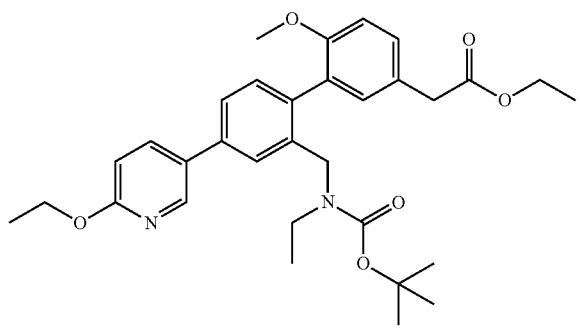 [SMILES: CCOC(=O)Cc1ccc(OC)c(-c2ccc(-c3ccc(OCC)nc3)cc2CN(CC)C(=O)OC(C)(C)C)c1]

Step 8: [2'-[(tert-Butoxycarbonyl-ethyl-amino)-methyl]-4'-(6-ethoxy-pyridin-3-yl)-6-methoxy-biphenyl-3-yl]-acetic acid ethyl ester 5-Bromo-2-ethoxypyridine (0.235 g, 1.16 mmol), [2'-[(tert-butoxycarbonyl-ethyl-amino)-methyl]-6-methoxy-4'-(4,4,5,5-tetramethyl-[1,3,2]dioxaborolan-2-yl)-biphenyl-3-yl]-acetic acid ethyl ester (0.500 g, 0.903 mmol), and potassium carbonate (0.313 g, 2.3 mmol) were combined in DME (5 mL) and water (2.5 mL) under nitrogen. The mixture was purged with nitrogen, and then tetrakis(triphenylphosphine)palladium(0) (0.052 g, 0.045 mmol) was added, and the reaction was heated to 85° C. for 6 hours. Once no starting material was seen by analytical LCMS, the mixture was cooled to room temperature and diluted with ethyl acetate and water. The aqueous layer was separated and extracted with ethyl acetate, and the combined organic layers were dried over magnesium sulfate, filtered, and concentrated. The residue was purified by silica gel chromatography (0-40% ethyl acetate in hexanes) to give the title compound.

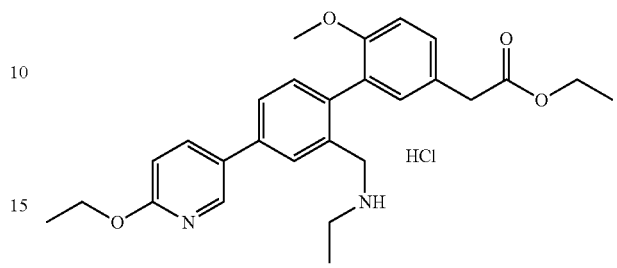

Step 9: [4'-(6-Ethoxy-pyridin-3-yl)-2'-ethylaminomethyl-6-methoxy-biphenyl-3-yl]-acetic acid ethyl ester hydrochloride

[2'-[(tert-Butoxycarbonyl-ethyl-amino)-methyl]-4'-(6-ethoxy-pyridin-3-yl)-6-methoxy-biphenyl-3-yl]-acetic acid ethyl ester (0.404 g, 0.736 mmol) in dichloromethane (3 mL) was treated with 4N hydrochloric acid in 1,4-dioxane (2.5 mL, 10 mmol) at room temperature, until complete conversion was seen by analytical LCMS. The mixture was concentrated to give the title compound.

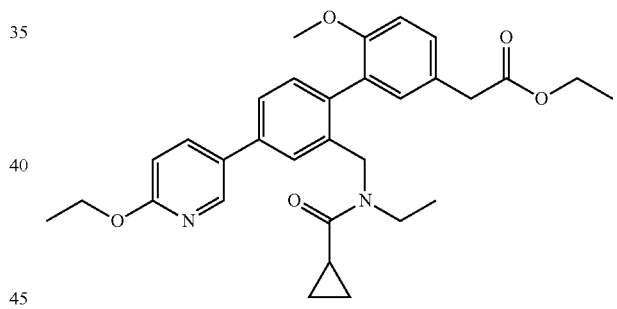

Step 10: [2'-[(Cyclopropanecarbonyl-ethyl-amino)-methyl]-4'-(6-ethoxy-pyridin-3-yl)-6-methoxy-biphenyl-3-yl]-acetic acid ethyl ester To [4'-(6-ethoxy-pyridin-3-yl)-2'-ethylaminomethyl-6-methoxy-biphenyl-3-yl]-acetic acid ethyl ester hydrochloride (0.357 g, 0.736 mmol) and N,N-diisopropylethylamine (0.75 mL, 4.3 mmol) in dichloromethane (4 mL) was added cyclopropanecarbonyl chloride (0.074 mL, 0.814 mmol), and the reaction was stirred at room temperature. Once no starting material was seen by analytical LCMS, the mixture was diluted with dichloromethane and water, and the aqueous layer was extracted with dichloromethane. The combined organic layers were dried over magnesium sulfate, filtered, and concentrated, and the residue was purified by silica gel chromatography (ethyl acetate in hexanes gradient) to give the title compound.

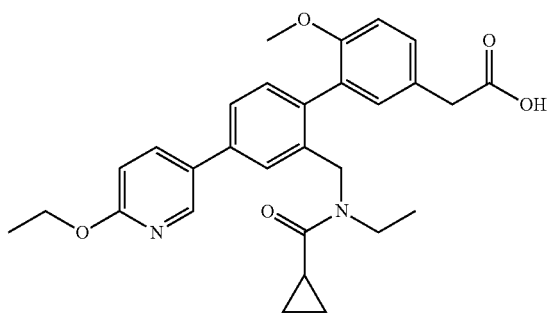 [SMILES: CCOc1ccc(-c2ccc(-c3cc(CC(=O)O)ccc3OC)c(CN(CC)C(=O)C3CC3)c2)cn1]

Step 11: [2'-[(Cyclopropanecarbonyl-ethyl-amino)-methyl]-4'-(6-ethoxy-pyridin-3-yl)-6-methoxy-biphenyl-3-yl]-acetic acid

[2'-[(Cyclopropanecarbonyl-ethyl-amino)-methyl]-4'-(6-ethoxy-pyridin-3-yl)-6-methoxy-biphenyl-3-yl]-acetic acid ethyl ester (0.296 g, 0.573 mmol) in tetrahydrofuran (5 mL) and water was treated with lithium hydroxide (0.090 g, 2.14 mmol) and the reaction was stirred at room temperature. When the reaction was complete by analytical LCMS, the mixture was acidified with 1N aqueous hydrochloric acid and extracted three times with ethyl acetate. The combined organic layers were dried and concentrated, and the residue was purified by preparative HPLC to give the title compound.

Example 2

Alternative Synthesis of [2'-[(Cyclopropanecarbonyl-ethyl-amino)-methyl]-4'-(6-ethoxy-pyridin-3-yl)-6-methoxy-biphenyl-3-yl]-acetic acid

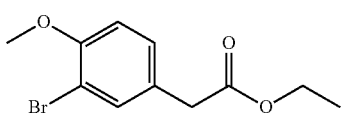

Step 1: (3-Bromo-4-methoxy-phenyl)-acetic acid ethyl ester

To (3-Bromo-4-methoxy-phenyl)-acetic acid (24 g, 97.9 mmol) in ethanol (240 mL) was added thionyl chloride (78 mL, 107.7 mmol) and the reaction was stirred at room temperature for 1.5 hours. Once no starting material was seen by analytical LCMS, saturated sodium bicarbonate (aqueous) was added until the reaction was of basic pH. The mixture was extracted twice with dichloromethane and the combined organic layers were washed with water, dried over magnesium sulfate, filtered, and concentrated to give the title compound.

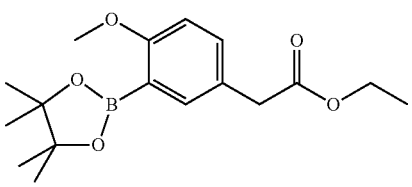 [SMILES: CCOC(=O)Cc1ccc(OC)c(B2OC(C)(C)C(C)(C)O2)c1]

Step 2: [4-Methoxy-3-(4,4,5,5-tetramethyl-[1,3,2]dioxaborolan-2-yl)-phenyl]-acetic acid ethyl ester (3-Bromo-4-methoxy-phenyl)-acetic acid ethyl ester (27.4 g, 100.3 mmol), bis(pinacolato)diboron (25.47 g, 100.3 mmol), and potassium acetate (24.6 g, 250.8 mmol) were combined in 1,4-dioxane (250 mL) under nitrogen. The solution was purged with nitrogen, and then (1,1'-bis(diphenylphosphino)ferrocene)-dichloropalladium(II) (4.10 g, 5.02 mmol) was added and the reaction was heated to 110° C. overnight. The mixture was filtered through Celite and partitioned between ethyl acetate and brine. The aqueous layer was separated and extracted twice with ethyl acetate, and the combined organic layers were dried (magnesium sulfate), filtered and concentrated. The residue was purified by silica gel chromatography (20-60% ethyl acetate in hexanes) to give the title compound.

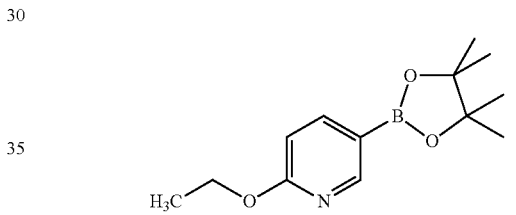

Step 3: 2-Ethoxy-5-(4,4,5,5-tetramethyl-[1,3,2]dioxaborolan-2-yl)-pyridine 5-bromo-2-ethoxypyridine (25.0 g, 123.7 mmol), bis(pinacolato)diboron (34.6 g, 148.5 mmol), and potassium acetate (36.5 g, 371.9 mmol) were combined in 1,4-dioxane (250 mL) under nitrogen. The solution was purged with nitrogen and then (1,1'-bis(diphenylphosphino)ferrocene)-dichloropalladium(II) (0.750 g, 0.92 mmol) was added and the reaction was heated to 80° C. for 16 hours. The mixture was cooled and concentrated then partitioned between ethyl acetate and water. The aqueous layer was separated and extracted twice with ethyl acetate, and the combined organic layers were dried with magnesium sulfate, filtered and concentrated. The residue was purified by silica gel chromatography (0-15% ethyl acetate in hexanes) to give the title compound.

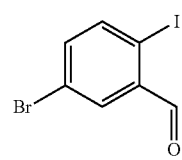

Step 4: 5-Bromo-2-iodobenzaldehyde 5-bromo-2-iodobenzonitrile (25.2 g, 81.8 mmol) in tetrahydrofuran (140 mL) was cooled to −78° C. and diisobutylaluminum hydride (1.0M in hexanes; 115 mL, 115 mmol) over 10 minutes, and the reaction was allowed to warm to room temperature and left stirring overnight. Analytical LCMS indicated consumption of starting material so the mixture was carefully quenched with ethyl acetate and methanol. After 1.5 hours the solution was concentrated then diluted with dichloromethane. 1N Aqueous hydrochloric acid was added and a precipitate formed as the reaction was stirred vigorously for 1 hour. The precipitate was filtered off and the filtrate was evaporated then triturated with dichloromethane and hexanes, which caused more precipitate to form. The mixture was filtered and the organic portions were set aside while the combined precipitates were suspended in tetrahydrofuran and 6N hydrochloric acid (aqueous). The reaction was stirred vigorously for 1 hour at which point analytical TLC indicated complete formation of the product. The reaction was extracted with dichloromethane and combined with the previous organic portions. The mixture was dried over magnesium sulfate then filtered, evaporated, and purified by silica gel chromatography (0-15% dichloromethane in hexanes) to yield the title compound.

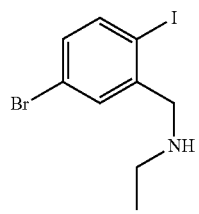

Step 5: (5-Bromo-2-iodo-benzyl)-ethyl-amine

To 5-bromo-2-iodo-benzaldehyde (15.0 g, 48.3 mmol) in methanol (60 mL) was added ethylamine (2.0M in methanol; 48 mL, 72.0 mmol), followed by acetic acid (3.0 mL, 53.4 mmol), and the mixture was stirred at room temperature for 30 minutes, after which a precipitate formed. Sodium cyanoborohydride (6.00 g, 95.4 mmol) was then added in 3 portions and the precipitate disappeared. The reaction was stirred at room temperature for 24 hours then quenched with saturated aqueous sodium bicarbonate. The resulting mixture was evaporated then diluted with dichloromethane and washed with water, dried over magnesium sulfate, filtered, and concentrated. The residue was purified by silica gel chromatography (0-4% methanol in dichloromethane) to give the title compound.

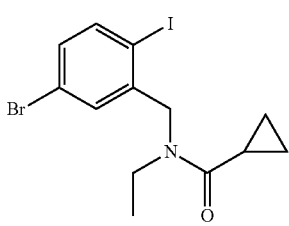 [SMILES: CCN(Cc1cc(Br)ccc1I)C(=O)C1CC1]

Step 6: Cyclopropanecarboxylic acid (5-bromo-2-iodo-benzyl)-ethyl-amide (5-Bromo-2-iodo-benzyl)-ethyl-amine (5.0 g, 14.7 mmol) was dissolved in dichloromethane (75 mL) along with N,N-diisopropylethylamine (5.12 mL, 29.4 mmol). The solution was cooled to 0° C. and cyclopropanecarbonyl chloride (1.41 mL, 15.4 mmol) was added. The reaction was monitored by analytical LCMS and after 15 minutes water was added and the layers were separated. The organic layer was dried with magnesium sulfate then filtered and concentrated to afford the title compound, which was used without further purification.

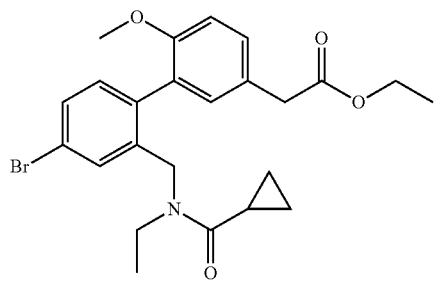 [SMILES: CCOC(=O)Cc1ccc(OC)c(-c2ccc(Br)cc2CN(CC)C(=O)C2CC2)c1]

Step 7: {4'-Bromo-2'-[(cyclopropanecarbonyl-ethyl-amino)-methyl]-6-methoxy-biphenyl-3-yl}-acetic acid ethyl ester Cyclopropanecarboxylic acid (5-bromo-2-iodo-benzyl)-ethyl-amide (6.0 g, 14.7 mmol), [4-methoxy-3-(4,4,5,5-tetramethyl-[1,3,2]dioxaborolan-2-yl)-phenyl]-acetic acid ethyl ester (5.2 g, 16.2 mmol), and potassium carbonate (5.09 g, 36.8 mmol) were combined in DME (50 mL) and water (20 mL) under nitrogen. The mixture was purged with nitrogen, and then tetrakis(triphenylphosphine)palladium(0) (0.85 g, 0.74 mmol) was added, and the reaction was heated to 75° C. The reaction was monitored by analytical LCMS and an additional portion of the boronic ester (0.500 g, 1.56 mmol) was added to push the reaction to completion. When the starting material was consumed, the mixture was cooled to room temperature and diluted with ethyl acetate and water. The aqueous layer was separated and extracted with ethyl acetate, and the combined organic layers were dried over magnesium sulfate, filtered, and concentrated. The residue was purified by silica gel chromatography (0-25% ethyl acetate in hexanes) to give the title compound.

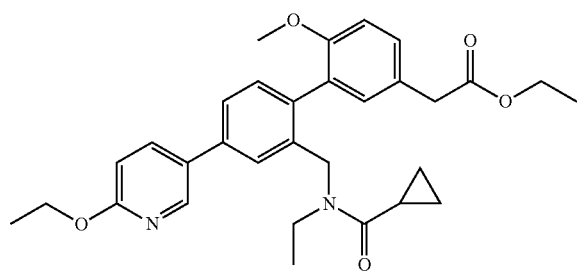 [SMILES: CCOC(=O)Cc1ccc(OC)c(-c2ccc(-c3ccc(OCC)nc3)cc2CN(CC)C(=O)C2CC2)c1]

Step 8: [2'-[(Cyclopropanecarbonyl-ethyl-amino)-methyl]-4'-(6-ethoxy-pyridin-3-yl)-6-methoxy-biphenyl-3-yl]-acetic acid ethyl ester {4'-Bromo-2'-[(cyclopropanecarbonyl-ethyl-amino)-methyl]-6-methoxy-biphenyl-3-yl}-acetic acid ethyl ester (14.5 g, 30.6 mmol) was dissolved in DME (100 mL) and water (50 mL) along with 2-ethoxy-5-(4,4,5,5-tetramethyl-[1,3,2]dioxaborolan-2-yl)-pyridine (9.1 g, 36.5 mmol) and potassium carbonate (10.7 g, 77.4 mmol) under $N_2$ atmosphere. The mixture was purged with $N_2$, and then tetrakis(triphenylphosphine)palladium(0) (0.500 g, 0.43 mmol) was added and the reaction was heated to 80° C. The reaction was monitored by analytical LCMS and when the starting material was consumed, the mixture was cooled to room temperature and diluted with ethyl acetate and water. The aqueous layer was separated and extracted with ethyl acetate, and the combined organic layers were dried over magnesium sulfate, filtered, and concentrated. The residue was purified by silica gel chromatography (0-35% ethyl acetate in hexanes) to afford the title compound.

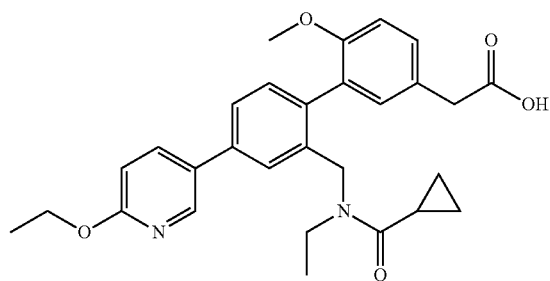 [SMILES: CCOc1ccc(-c2ccc(-c3cc(CC(=O)O)ccc3OC)c(CN(CC)C(=O)C3CC3)c2)cn1]

Step 9: [2'-[(Cyclopropanecarbonyl-ethyl-amino)-methyl]-4'-(6-ethoxy-pyridin-3-yl)-6-methoxy-biphenyl-3-yl]-acetic acid

[2'-[(cyclopropanecarbonyl-ethyl-amino)-methyl]-4'-(6-ethoxy-pyridin-3-yl)-6-methoxy-biphenyl-3-yl]-acetic acid ethyl ester (32.7 g, 63.3 mmol) in tetrahydrofuran (150 mL) and water (75 mL) was treated with lithium hydroxide (8.0 g, 190.6 mmol) and the reaction was stirred at room temperature overnight. When the reaction was complete by analytical LCMS, the mixture was acidified with 1N aqueous hydrochloric acid to pH 3 and extracted 2 times with dichloromethane. The combined organic layers were dried over magnesium sulfate and concentrated to afford the title compound as an off-white foam.

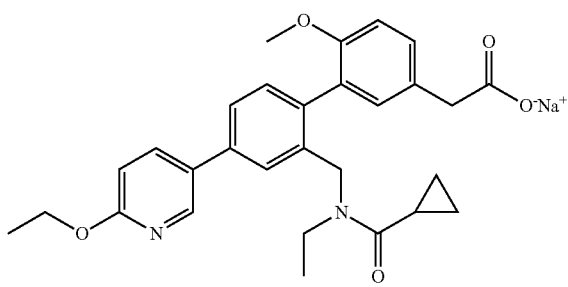

Step 10: [2'-[(Cyclopropanecarbonyl-ethyl-amino)-methyl]-4'-(6-ethoxy-pyridin-3-yl)-6-methoxy-biphenyl-3-yl]-acetic acid sodium salt

[2'-[(Cyclopropanecarbonyl-ethyl-amino)-methyl]-4'-(6-ethoxy-pyridin-3-yl)-6-methoxy-biphenyl-3-yl]-acetic acid (26.0 g, 53.2 mmol) was dissolved in ethanol (180 mL), sodium hydroxide (53.2 mL, 1N aq.) was added and the reaction was stirred at room temperature for 1 hour. The solution was filtered to remove solid impurities then concentrated. The residue was dissolved in water (~150 mL) then frozen and lyophilized to afford the title compound.

Example 3

Formulation of a $DP_2$ Receptor for Antagonist Compound

In one aspect, aqueous ophthalmic solutions that include a $DP_2$ receptor antagonist compound are prepared by dissolving a $DP_2$ receptor antagonist compound in 10% beta-hydroxypropyl cyclodextrin (BHPC) in water.

Example 4

Solution of $DP_2$ Receptor Antagonist Compound 1.5 g of a $DP_2$ receptor antagonist compound is dissolved in 25 mL of PBS buffer. Boric acid (50 mg) is added to the solution followed by addition of 100 μL of benzalkonium chloride. Polyvinyl alcohol (1.5 mL) and Polysorbate (1 mL) are added to the mixture and the pH is adjusted to pH 7.1 using 1N hydrochloric acid or 1N sodium hydroxide. The final volume of the solution is adjusted to 100 mL with saline.

Example 5

Solution of $DP_2$ Receptor Antagonist Compound (Preservative Free)

1.5 g of a $DP_2$ receptor antagonist compound is dissolved in 25 mL of citrate buffer. Mannitol (50 mg) is added to the solution followed by addition of tyloxapol (1 mL) and the pH is adjusted to 6.9 using 1N hydrochloric acid or 1N sodium hydroxide. The final volume of the solution is adjusted to 100 mL with saline.

Example 6

Ointment of $DP_2$ Receptor Antagonist Compound 1.5 g of a $DP_2$ receptor antagonist compound is dissolved in 1.5 mL mineral oil. White petrolatum (500 mg) is added to the mixture followed by addition of chlorobutanol (10 μl). The ointment is filled in sterile tubes.

Example 7

$DP_2$/CRTH2 Binding Assay

The ability of a compound to bind to the human $DP_2$ receptor is assessed via a radioligand binding assay using [$^3$H]PGD$_2$. HEK293 cells stably expressing recombinant human $DP_2$ are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol to approximately 5 mg protein/ml. Membranes (2-10 μg protein/well) are incubated in 96-well plates with 1 nM [$^3$H]PGD$_2$ and test compound in Assay Buffer (50 mM Hepes, 10 mM MnCl$_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polythylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 µM $PGD_2$. $IC_{50}$s were determined using GraphPad prism analysis of drug titration curves.

Example 8

$DP_1$ Binding Assay

The ability of a compound to bind to the human DP1 receptor was evaluated via a radioligand membrane binding assay using the $DP_1$ selective synthetic ligand [$^3$H] BWA868C. Packed human platelets (Biological Specialty Corporation), were resuspended in 6 volumes of Hepes/HBSS buffer (10 mM Hepes, 1 mM DTT in Hanks Balanced Salt Solution (HBSS)), lysed and centrifuged at 75,000×g to pellet the membranes. Membranes were resuspended in Hepes/HBSS buffer to approximately 12 mg protein/ml. Membranes (20 µg protein/well) are incubated in 96-well plates with 2 nM [$^3$H]BWA868C and test compound in Assay Buffer (50 mM Hepes, 10 mM $MnCl_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polethylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 µM BW A868C. $IC_{50}$s were determined using GraphPad prism analysis of drug titration curves.

Representative data for compounds tested in Example 7 and Example 8 is presented in the following table.

TABLE 1

Representative Biological Data

| Compound | hDP2 µM | hDP1 µM |
|---|---|---|
| [2'-(3-Benzyl-1-ethyl-ureidomethyl)-6-methoxy-4'-trifluoromethyl-biphenyl-3-yl]-acetic acid | A | C |
| {3-[2-tert-Butylsulfanylmethyl-4-(2,2-dimethyl-propionylamino)-phenoxy]-4-methoxy-phenyl}-acetic acid | A | C |
| {2'-[(N-cyclopropanecarbonyl-N-ethyl-amino)-methyl]-6-methoxy-4'-trifluoromethyl-biphenyl-3-yl}-acetic acid | A | C |
| [2'-[(N-cyclopropanecarbonyl-N-ethyl-amino)-methyl]-4'-(6-ethoxy-pyridin-3-yl)-6-methoxy-biphenyl-3-yl]-acetic acid | A | C |
| (5-{2-[(N-benzyloxycarbonyl-N-ethyl-amino)-methyl]-4-trifluoromethyl-phenyl}-pyridin-3-yl)-acetic acid | A | C |
| {8-[(4-fluoro-benzenesulfonyl)-methyl-amino]-6,7,8,9-tetrahydro-pyrido[3,2-b]indol-5-yl}-acetic acid | A | C |
| Ramatroban | B | C |

A = less than 0.3 µM;
B = greater than 0.3 µM but less than 1 µM;
C = greater than 1 µM.

Example 9

Rat Model of Allergic Conjunctivitis

A rat model of allergic conjunctivitis is used to test the effect of topical administration of a $DP_2$ receptor antagonist compound to the eye on the development of allergic conjunctivitis. Male wistar rats (250-350 g) are sensitized by injection with 0.6 mL saline containing ovalbumin (OVA, 1 mg), alum (2 mg) and $10^{10}$ killed *B. pertussis* cells into all four footpads on day 1. Five days later they are boosted by subcutaneous injection with 1 ml of saline containing OVA (0.5 mg) in 10 sites on the back. Local sensitization is performed daily from days 14 to day 42 by instilling OVA in saline (10 mg/ml, 5 µl) into the bilateral eyes using a micropipette. Rats are treated with systemic or ocular $DP_2$ receptor antagonist on days 14 to 42 (as appropriate). The frequency of eye scratching behavior is counted for 20 min post OVA on selected days. Twenty-four hours following OVA challenge on days 14, 21, 28, 35 and 42 rats are anesthetized and the conjunctiva removed and fixed with 10% neutral buffered formalin. 4-µm thick frontal sections are stained and eosinophils counted. The inhibition of eye scratching behavior and conjunctiva eosinophils following topical treatment with a $DP_2$ receptor antagonist compound to the eye(s) is recorded and plotted using Graphpad Prizm.

Example 10

Guinea Pig Model of Allergic Conjunctivitis

A guinea pig model of allergic conjunctivitis is used to test the effect of topical administration of a $DP_2$ receptor antagonist to the eye on the development of allergic conjunctivitis. Male Hartley Guinea pigs ages 4-8 weeks (300-500 grams) at the beginning of the experiment were sensitized by intraperitoneal injection of ovalbumin [0.5 ml of a 100 µg/ml solution in Imject Alum. An additional 0.5 ml of the ovalbumin (OVA) solution is injected subcutaneous in the proximity of the lymph nodes (Muise et al., 2002). Twenty one days after sensitization, guinea pigs received an ocular challenge. Briefly, animals were secured within a towel and placed in a lateral recumbent position. Ten microliters of saline or OVA (2.5% in Saline) was topically applied to each eye, followed by 2-3 manually forced blinks. This procedure is repeated again on day 23. Clinical scoring of redness (using a scale of 0-3), edema (using a scale of 0-3) and discharge (using a scale of 0-4) were evaluated 90 minutes after challenge on day 23. The itch/scratch response was observed and recorded (using a scale of 0-3) for the first 30 minutes after challenge on day 23. The $DP_2$ receptor antagonist (compound 2; {2'-[(N-cyclopropanecarbonyl-N-ethyl-amino)-methyl]-6-methoxy-4'-trifluoromethyl-biphenyl-3-yl}-acetic acid) was administered on days 21-23 by topical application using the procedure described above in a concentration of 300 ng/eye in PBS vehicle. Oral administration was also evaluated by gavage of compound 2 (10 mg/kg) prepared in 0.5% Methylcellulose or water. The means±standard error of the mean were plotted and analyzed by one-way ANOVA using Graphpad Prizm.

Figure 3:
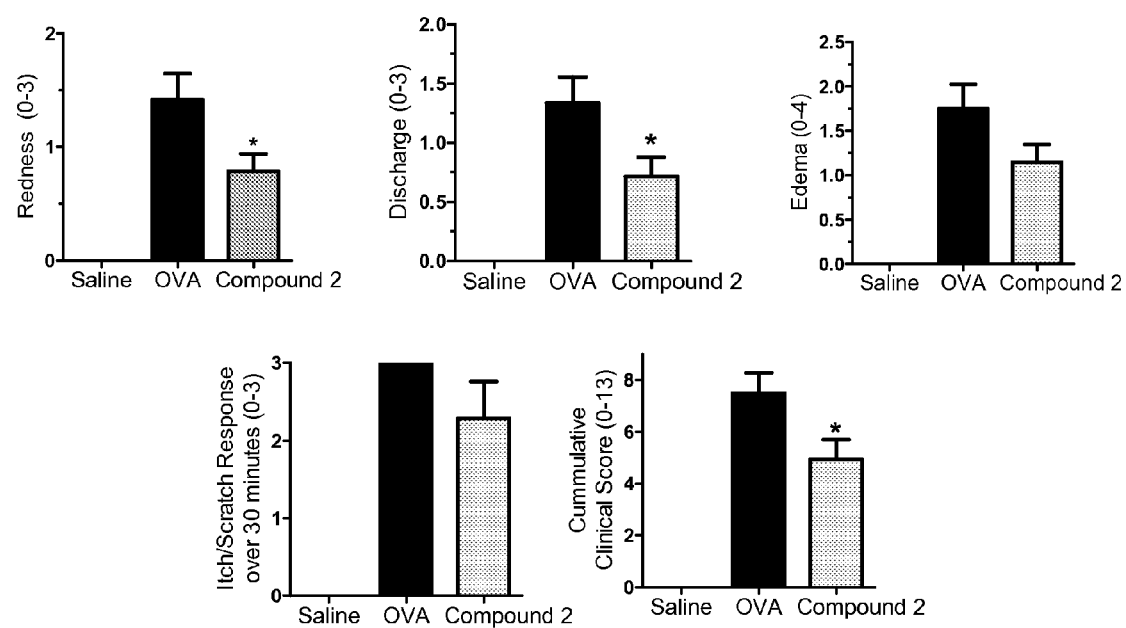
FIG. 3 illustrates the effect of topical administration of a $DP_2$ receptor antagonist to the eyes on the development of allergic conjunctivitis in a guinea pig model of allergic conjunctivitis.

FIG. 3 shows that topical administration of compound 2 significantly reduced redness, discharge and cummulative clinical score following ocular antigen challenge. Ocular edema and the itch/scratch response showed a trend toward reduction. Oral administration of compound 2 failed to impact any endpoint.

Example 11

Mouse Ragweed Allergic Conjunctivitis

A mouse model of ragweed-induced allergic conjunctivitis was used to test the efficacy of topical administration of a $DP_2$ receptor antagonist to the eye on the development of allergic conjunctivitis. Compound 2 was evaluated in a mouse model of ocular allergy. In this model, a systemic sensitization with an allergen (Short Ragweed, SRW) was followed by topical challenge with the same allergen. For sensitization a suspension of 50 μg of short ragweed allergen (SRW, Greer, Lenoir, NC, USA) 25 μl of Aluminum Hydroxide (13 mg/ml, Sigma Aldrich) was injected into both hind rear footpads (Day 0). On days 9 through 15, topical treatment with compound 2 (0.3% in PBS), positive control (Prednisolone Acetate 1% in hypromellose), or vehicle control (PBS) was administered three times daily. Mice were dosed topically to the central cornea using a calibrated micropipette, with a 5 μL drop of treatment in each eye. On days 13 through 15 mice were challenged with topical doses of 1000 μg SRW suspension in 5 μl PBS in each eye. SRW was prepared fresh daily, and used within 3 hours of mixing, and mixed well before administration to ensure homogeneity. Thirty minutes after the final challenge (Day 15) clinical signs (discharge, lid swelling hyperemia, chemosis, and squinting) were evaluated using the aid of a dissecting microscope. A cumulative score was also recorded including all parameters measured with the exception of squinting.

Figure 5:
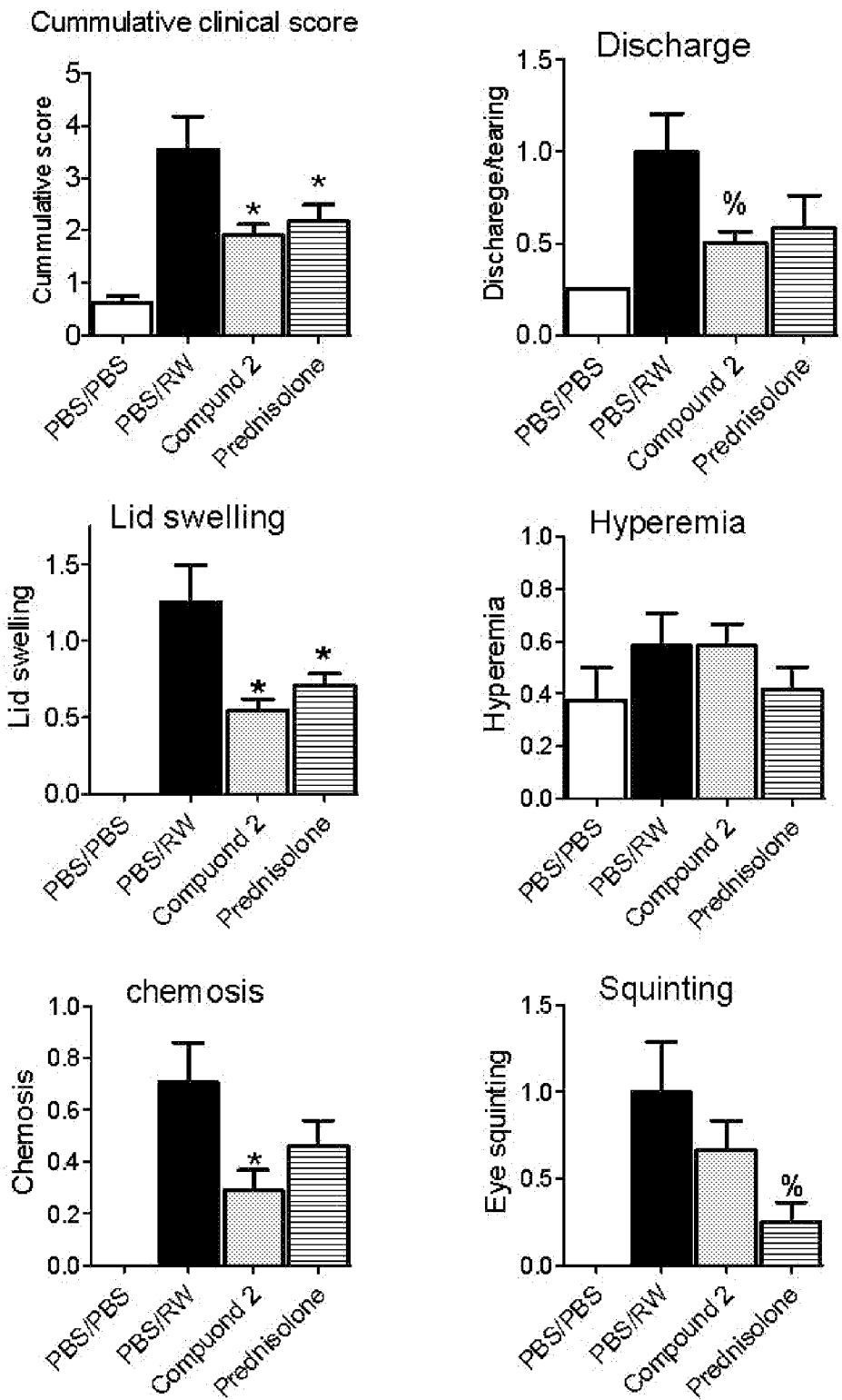
FIG. 5 illustrates the effect of topical administration of a $DP_2$ receptor antagonist to the eyes in a mouse model of ocular allergy.

FIG. 5 shows that topical administration of compound 2 significantly reduced discharge, lid swelling, chemosis, and cumulative clinical score following ocular antigen challenge. * $P<0.05$ versus PBS/RW, Newman-Keuls post hoc following ANOVA; % $P<0.05$ versus PBS/RW, t-test.

Example 12

Mouse Model of RSV-Infected Eye

A mouse model of respiratory syncytial virus (RSV) eye infection is used to test the effects of ocular application of $DP_2$ receptor antagonist compound on RSV-induced ocular immunopathology (Bitko V, et al., *J. Virol.* 2007; 81(2):783-90; Bitko V, et al., *Nat. Med.* 2005; 11(1):50-5). Each mouse eye is topically treated with 60 ng $DP_2$ receptor antagonist compound or vehicle (sterile saline) in a volume of 2 μl. The $DP_2$ receptor antagonist compound is instilled 40 min after virus inoculum and then once daily over the entire duration of the protocol (14 days).

Instillation of virus and inhibitor in the eye. Female BALB/c mice, 6 to 8 weeks old, are purchased from Charles River Laboratories. RSV (Long strain, serotype A) is grown on HEp-2 cells and purified on sucrose layers to a concentration of $10^{11}$ PFU (Bitko et al., *Nat. Med.* 11:50-55, 2005). Dilutions are done in phosphate-buffered saline (PBS) immediately before use to a final concentration of $10^4$ PFU/2 μL as needed. A similarly diluted sucrose solution is used in sham-infected control mice. Mice are anesthetized by intraperitoneal injection of pentobarbital (50 mg/kg), and virus in 2 μL PBS is dropped into the corneal surface and massaged in with closed eyelids. The day of the inoculation is considered day 0. The $DP_2$ receptor antagonist compound is diluted in PBS to 60 ng/2 μL just prior to application of 2 μL 40 minutes after the RSV inoculation on day 0 and then each day.

Duration of the experiment: Eyes are visually examined daily, and harvested on each of the following days post-RSV inoculation: Day 2, 4, 6, 8, 9, 10, 12, 14=a total of 8 time points. Three animals are used for each data point i.e. 24 mice treated with a $DP_2$ receptor antagonist compound and 24 mice treated with vehicle control (for a total of 48 mice used in the study).

Ocular pathology. Ocular disease is evaluated with a slit lamp biomicroscope (Bitko V, et al., *J. Virol.* 2007; 81(2):783-90)15; Girgis et al., Invest. Ophthal. Vis. Sci. 44:1591-1597, 2003). Pathology is scored on a scale of 0 to 5 as follows: 0=clear eye; 1=slight redness in the corners; 2=moderate redness and injection; 3=conjunctival and corneal injection with ciliary flush; 4=extensive injection, generally associated with some mucus; 5=most extensive injection, associated with mucus. Eyes are examined in a coded fashion with the reader unaware of the treatment given. The presence of gummy residue or mucin in the eyes is recorded. Pathology scores after ocular application of the $DP_2$ receptor antagonist compound are recorded on all observation days, i.e, days 2-14 after RSV challenge. A therapeutically effective $DP_2$ receptor antagonist compound reduces gummy residue and/or mucin build up in infected eyes.

Interleukin-4 (IL-4) measurements. Eye tissues are homogenized in 1-3 ml lysis buffer (0.5% Triton-X-100, 15 mM Tris Cl pH 7.4) using a polytron homogenizer. The homogenate is centrifuged at 10,000×g for 10 min at 4 degrees celsius and supernatant frozen at −80 degrees celsius prior to processing for IL-4 extractions. Supernatant samples are thawed and precipitated with final volume 10% ice cold methanol, held on ice for 30 minutes, then centrifuged at 10,000×g for 15 minutes. Eye extract as described above is used to determine levels of IL-4 in the extracts.

RSV RNA and protein: RSV is assayed in the ocular tissue on various days using both Western blot and viable virus assay (plaque forming unit; pfu) as described before. IL-5 is quantified by RT-PCR. RSV RNA and protein are measured in the eye and lung (Urnowey et al., BMC Microbiol. 6:26, 2006).

Infection of an eye eventually transmits into the lung, causing a standard respiratory infection. In some instances, eye serves as a portal of entry for RSV in to the lung. Thus, it is of interest to monitor the lung infection to determine if the ocular application of the $DP_2$ receptor antagonist compound has any effect on virus replication and quantity of virus in the lung. The mice lung tissue is harvested, homogenates made and assayed for viral titer and Western blot (Matsuse H, et al. *Allergology International* 2007; 56:165-169; Bitko V, et al., *J. Virol.* 2007; 81(2):783-90.

Statistical Analysis. The pathology scores and ocular IL-4 concentrations are subjected to a two-way ANOVA followed by bonferroni post hoc analysis using GraphPad Prism software (GraphPad Software, San Diego, Calif.).

Figure 4:
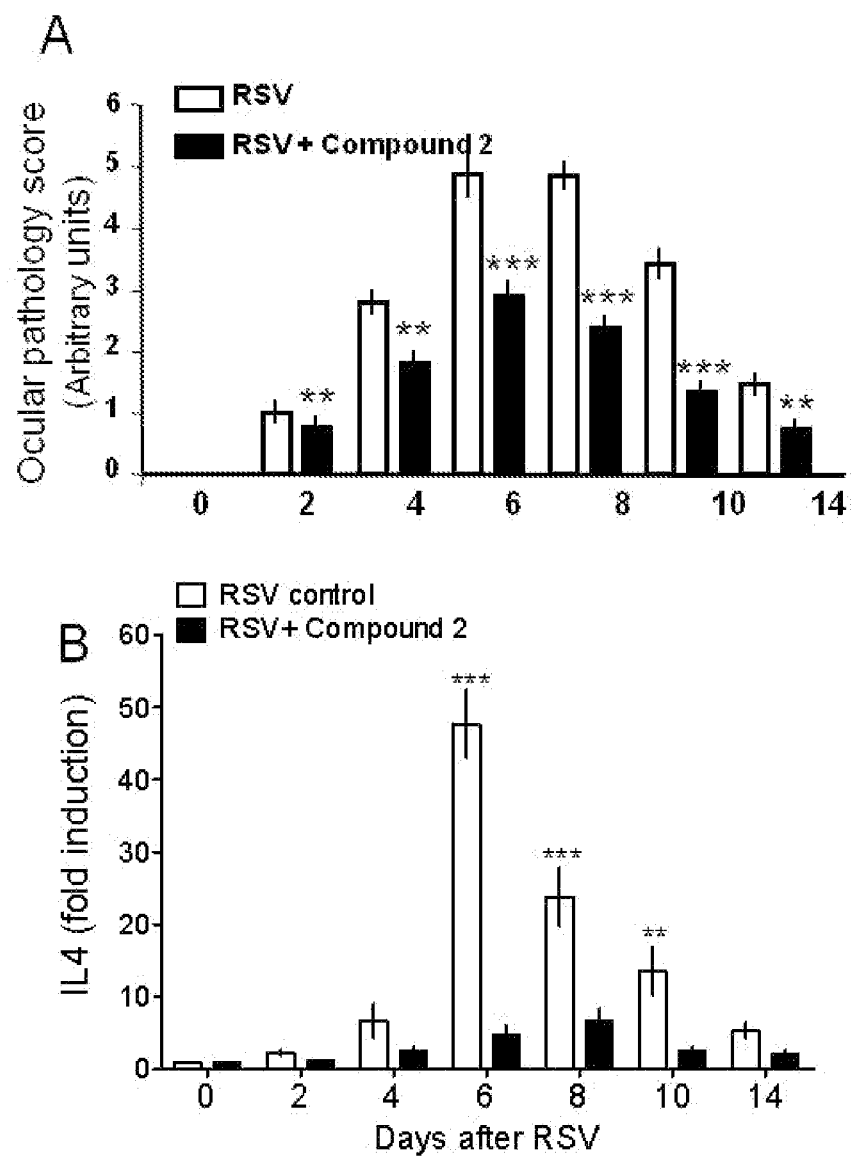
FIG. 4 illustrates the effect of a $DP_2$ receptor antagonist on RSV eye pathology and eye IL4 induction in a mouse model of RSV-infected eye.

The $DP_2$ receptor antagonist (compound 2; {2'-[(N-cyclopropanecarbonyl-N-ethyl-amino)-methyl]-6-methoxy-4'-trifluoromethyl-biphenyl-3-yl}-acetic acid) reduced (A) RSV eye pathology and (B) eye IL4 induction (see FIG. 4).

Example 13

Combination Therapy in a Mouse Subchronic Smoke Model

Figure 2:
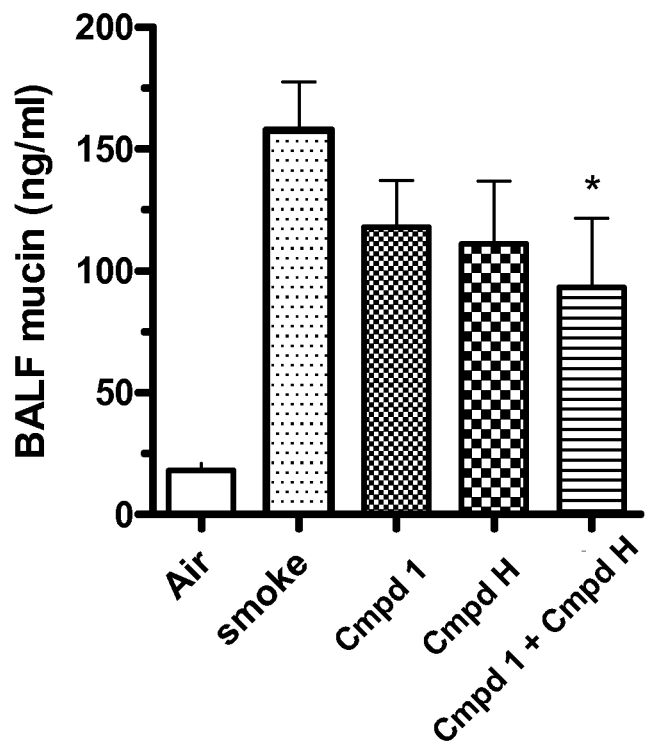
FIG. 2 illustrates the effect of a $DP_2$ receptor antagonist, alone or in combination with a FLAP inhibitor, on the presence of mucin in BALF.

BALB/c mice were divided into groups and acclimatized in cages for 24 hours (day 0). The control group was exposed to air and the test group was exposed to smoke from seven unfiltered cigarettes per day for 8 days (day 1 to day 8). A $DP_2$ receptor antagonist 5-{2-[(N-benzyloxycarbonyl-N-ethyl-amino)-methyl]-4-trifluoromethyl-phenyl}-pyridin-3-yl)-acetic acid (Compound 1; 10 mg/kg qd), alone or in combination with a FLAP inhibitor compound H (3-(3-(tert-butylthio)-1-(4-(6-methoxypyridin-3-yl)benzyl)-5-((5-methylpyridin-2-yl)methoxy)-1H-indol-2-yl)-2,2-dimethylpropanoic acid) (30 mg/kg, b.i.d.) are administered starting at day 1 and up to day 13. On day 14, bronchoalveolar lavage fluid (BALF) is tested for influx of cells, cytokines, chemokines (e.g., KC, IL-17, MIP-2, IL-6), mucin, and/or proteins. Lung histology is also examined. FIG. 1 illustrates the effect of $DP_2$ receptor antagonism, alone or in combination with FLAP inhibition on the number of total cells, neutrophils and lymhocytes present in BALF. FIG. 2 illustrates the effect of a $DP_2$ receptor antagonist, alone or in combination with a FLAP inhibitor on the presence of mucin in BALF. In the subchronic smoking mouse model, the effects of a combination of a $DP_2$ receptor antagonist compound and a FLAP inhibitor compound on mucin secretion in BALF were additive, i.e., a combination of Compound 1 and Compound H reduced the amount of mucin in BALF more than each compound alone. In one aspect, the effects of topical administration of a $DP_2$ receptor antagonist, either alone or in combination with a FLAP inhibitor compound, to the eyes has the same effects in the eyes (e.g., mechanistically expected) as observed in the BALF.

Example 14

Clinical Trial Evaluating Effect of Topical Administration of a $DP_2$ Receptor Antagonist to the Eye in Reducing Signs and Symptoms of Allergic Conjunctivitis A single-center, double-blind, randomized, two way cross-over, placebo-controlled study to evaluate the safety and efficacy of topical administration of a $DP_2$ receptor antagonist compound to the eye of individuals with allergic conjunctivitis (AC) following conjunctival allergen challenge (CAC). Each subject will receive the active treatment (e.g. a topical formulation of a $DP_2$ receptor antagonist compound administered to the eye) or placebo.

Ten subjects aged 18-65 years of either gender are to participate in the study. All subjects should have a medical history of ocular allergies (allergic conjunctivitis or rhinoconjunctivitis). Their allergic status should have been confirmed by (1) positive skin prick test to a seasonal or perennial allergen, (2) a positive ocular allergen challenge to the same allergen.

No subject should have glaucoma, anterior or posterior uveitis, clinically significant blepharitis, follicular conjunctivitis, iritis or dry eye; diabetic retinopathy, or progressive retinal disease; presence of an active ocular infection; a positive history of an ocular herpetic infection. Also excluded are subjects that have had previous treatment (within 2 weeks prior to randomization) with any systemically administered or ophthalmically administered corticosteroids; or any systemically administered or ophthalmically administered mast cell stabilizers; subjects who had an upper respiratory tract infection 4 weeks before randomization, or subjects who have undergone ocular surgery within 6 months or had a history of retinal detachment. Female subjects of child bearing potential must have a documented negative urine pregnancy test and must be practicing a medically proven form of contraception during the course of the study period. Written informed consent is obtained from each subject.

Conjunctival Allergen Challenge (CAC) Protocol

Demographic, medical and medication histories are obtained from patients. Patients that are eligible will have CAC performed bilaterally with an allergen to which the patient had previously reacted positively following a skin test. Allergen is instilled at increasing concentrations at 10-minute intervals until a positive reaction is observed. Patients and physician will then assess signs and symptoms of ocular inflammation: ocular itching, tearing, and redness/burning sensation using a 5 point scale (0=none to 4=incapacitating) for each symptom at 3, 7 and 20 minutes and 12 hours post CAC. The patient symptom score is the sum of individual scores as rated by the patient. The concentration of allergen inducing a 30% change in the patient symptom score (PD 30), as measured by the AUC symptom score 0 to 20 minutes, will be established. Each patient will then receive the allergen challenge with PD 30 concentration at day 1 of the first period of the cross over and again at day 1 of the second period of the cross over. Each patient will receive the treatment (active or placebo) immediately after allergen challenge. The two periods of the cross over will be separated by a seven-day wash out period.

The primary endpoint of the study is the variation of patient symptom score (AUC symptom score 0 to 20 minutes) treated versus placebo. Secondary endpoints include the individual ocular signs and symptoms as assessed by the patient and the physician, the overall assessment of the patient, the overall assessment of the physician, safety and tolerability, nasal symptoms, and biomarkers in the lachrymal secretions.

The examples and embodiments described herein are for illustrative purposes and various modifications or changes suggested to persons skilled in the art are to be included within the spirit and purview of this application and scope of the appended claims. The section headings used herein are for organizational purposes only and are not to be construed as limiting the subject matter described.

What is claimed is:

1. A method of treating an ophthalmic disease or condition in a mammal comprising topically administering an ophthalmic pharmaceutical composition comprising a $DP_2$ receptor antagonist compound and at least one pharmaceutically acceptable excipient to the eyes of the mammal, wherein the $DP_2$ receptor antagonist compound is a compound having the structure of Formula (II), or a pharmaceutically acceptable salt thereof:

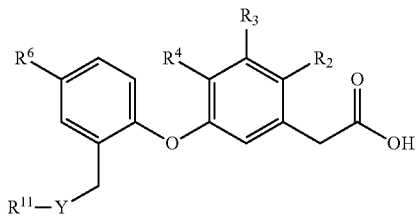

Formula (II)

wherein,
each of $R^2$, $R^3$, and $R^4$ is independently H, F, Cl, Br, I, —CN, —$C_1$-$C_6$alkyl, $C_1$-$C_6$fluoroalkyl, $C_1$-$C_6$fluoroalkoxy, $C_1$-$C_6$alkoxy, or $C_1$-$C_6$heteroalkyl;
$R^6$ is F, Cl, Br, I, —CN, —$NO_2$, —OH, —O($C_1$-$C_6$alkyl), —S(=O)$_2R^{12}$, —N($C_1$-$C_4$alkyl)S(=O)$_2R^{12}$, —NHS(=O)$_2R^{12}$, —S(=O)$_2$N($R^{13}$)$_2$, —C(=O)$R^{12}$, —$CO_2$($C_1$-$C_6$alkyl), —$NH_2$, —C(=O)NH($R^{13}$), —C(=O)N($R^{13}$)$_2$, —OC(=O)NH($R^{13}$), —OC(=O)N($R^{13}$)$_2$, —N($C_1$-$C_4$alkyl)C(=O)N($R^{13}$)$_2$, —NHC(=O) N($R^{13}$)$_2$, —NHC(=O)NH($R^{13}$), —N($C_1$-$C_4$alkyl)C (=O)$R^{12}$, —NHC(=O)$R^{12}$, —NH—$C_1$-$C_4$alkyl-C (=O)$R^{12}$, —N($C_1$-$C_4$alkyl)C(=O)O$R^{12}$, —NHC (=O)OR$^{12}$, C$_1$-C$_6$alkyl, C$_1$-C$_6$fluoroalkyl, C$_1$-C$_6$fluoroalkoxy, C$_1$-C$_6$heteroalkyl, a substituted or unsubstituted C$_2$-C$_{10}$heterocycloalkyl, a substituted or unsubstituted phenyl, or a substituted or unsubstituted monocyclic or bicyclic heteroaryl containing 0-3 heteroatoms selected from N, O or S;

R$^{11}$ is C$_1$-C$_6$alkyl, C$_1$-C$_6$haloalkyl, C$_1$-C$_6$heteroalkyl, a substituted or unsubstituted phenyl, a substituted or unsubstituted monocyclic or bicyclic heteroaryl containing 0-3 heteroatoms selected from N, O or S, a substituted or unsubstituted —C$_1$-C$_6$alkyl-phenyl, —C$_1$-C$_6$alkylene-N(R$^{17}$)$_2$, —C$_1$-C$_6$alkylene-C(=O)O—R$^{17}$, or —C$_1$-C$_6$alkylene-C(=O)N(R$^{17}$)$_2$; R$^{17}$ is H, or C$_1$-C$_6$alkyl;

R$^{12}$ is C$_1$-C$_6$alkyl, C$_1$-C$_6$heteroalkyl, C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted phenyl, a substituted or unsubstituted monocyclic heteroaryl containing 0-3 heteroatoms selected from N, O or S, a substituted or unsubstituted —C$_1$-C$_4$alkyl-C$_3$-C$_{10}$cycloalkyl, a substituted or unsubstituted —C$_1$-C$_4$alkyl-phenyl, or a substituted or unsubstituted —C$_1$-C$_4$alkyl-(monocyclic heteroaryl containing 0 to 3 heteroatoms selected from N, O or S);

each R$^{13}$ is independently selected from H, C$_1$-C$_6$alkyl, C$_1$-C$_6$ heteroalkyl, C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted phenyl, a substituted or unsubstituted monocyclic heteroaryl containing 0-3 heteroatoms selected from N, O or S, a substituted or unsubstituted —C$_1$-C$_4$alkyl-C$_3$-C$_{10}$cycloalkyl, a substituted or unsubstituted —C$_1$-C$_4$alkyl-C$_2$-C$_{10}$heterocycloalkyl, a substituted or unsubstituted —C$_1$-C$_4$alkyl-phenyl, and a substituted or unsubstituted —C$_1$-C$_4$alkyl-(monocyclic heteroaryl containing 0 to 3 heteroatoms selected from N, O or S); or two R$^{13}$ groups attached to the same N atom are taken together with the N atom to which they are attached to form a substituted or unsubstituted C$_2$-C$_{10}$heterocycloalkyl; and Y is —S—, —S(=O)—, or —S(=O)$_2$—.

2. The method of claim 1, wherein the ophthalmic pharmaceutical composition is in a form suitable for administration to the eyes of a mammal.

3. The method of claim 2, wherein the ophthalmic pharmaceutical composition compound is in the form of an ophthalmic solution, ophthalmic suspension, ophthalmic drops, ophthalmic emulsion, ophthalmic ointment, ophthalmic gel or an ophthalmic insert.

4. The method of claim 2, wherein the ophthalmic pharmaceutical composition is administered to the eye of the mammal via implantation, insertion, injection, spraying, washing, or combinations thereof.

5. The method of claim 1, wherein the ophthalmic disease or condition is an immune disorder; a proliferation disorder; contact with an allergen and/or an irritant; a mast cell mediated disease or condition; a Th2 lymphocyte mediated disease or condition; an infection, or combinations thereof.

6. The method of claim 1, wherein the ophthalmic disease or condition is age-related macular degeneration, allergic conjunctivitis, eosinophilic keratitis, anterior segment scarring, blepharitis, blepharoconjunctivitis, a bullous disorder, cicatricial pemphigoid, conjunctival melanoma, conjunctivitis, contact lens-associated giant papillary conjunctivitis, diabetic retinopathy, dry eye, episcleritis, glaucoma, gliosis, granuloma annulare, Graves' ophthalmopathy, intraocular melanoma, keratitis, keratoconjunctivitis, pain, pinguecula, post-surgical pain, proliferative vitreoretinopathy, pterygia, scarring, scleritis, Sjögren's syndrome, uveitis, vernal keratoconjunctivitis or combinations thereof.

7. The method of claim 1, wherein the ophthalmic disease or condition is ocular itching or ocular inflammation.

8. The method of claim 1, wherein the ophthalmic disease or condition comprises redness, irritation, swelling, lachrymal secretions, or a combination thereof in the eye of a mammal.

9. The method of claim 1, wherein the method comprises administering a second therapeutic agent to the mammal.

10. The method of claim 9, wherein the second therapeutic agent is an antibiotic, an anti-fungal agent, a steroid anti-inflammatory agent, a non-steroidal anti-inflammatory agent, an antiviral agent, an alpha agonist, a beta blocker, a carbonic anhydrase inhibitor, a prostaglandin, an anti-angiogenesis agent, loteprednol etabonate, a mast cell stabilizer, cyclosporine, or a leukotriene modulator.

11. The method of claim 9, wherein the second therapeutic agent is a leukotriene modulator selected from 5-lipoxygenase (5-LO) inhibitors, 5-lipoxygenase activating protein (FLAP) inhibitors, and leukotriene receptor antagonists.

12. An ophthalmic pharmaceutical composition comprising a DP$_2$ receptor antagonist compound and at least one pharmaceutically acceptable excipient to provide a solution suspension drop, emulsion, ointment, gel or an insert; wherein the ophthalmic pharmaceutical composition is in a form suitable for administration to an eye of a mammal; wherein at least one pharmaceutically acceptable excipient is selected from a pH adjusting component, cosolvent, emulsifier, penetration enhancer, preservative system, and emollient, or combination thereof; and wherein the DP$_2$ receptor antagonist compound is a compound having the structure of Formula (II), or a pharmaceutically acceptable salt thereof:

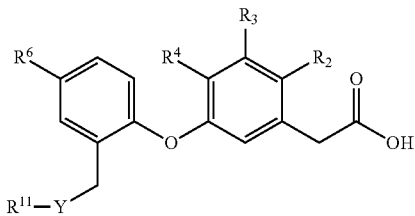

Formula (II)

wherein, each of R$^2$, R$^3$, and R$^4$ is independently H, F, Cl, Br, I, —CN, —C$_1$-C$_6$alkyl, C$_1$-C$_6$fluoroalkyl, C$_1$-C$_6$fluoroalkoxy, C$_1$-C$_6$alkoxy, or C$_1$-C$_6$heteroalkyl;

R$^6$ is F, Cl, Br, I, —CN, —NO$_2$, —OH, —O(C$_1$-C$_6$alkyl), —S(=O)$_2$R$^{12}$, —N(C$_1$-C$_4$alkyl)S(=O)$_2$R$^{12}$, —NHS(=O)$_2$R$^{12}$, —S(=O)$_2$N(R$^{13}$)$_2$, —C(=O)R$^{12}$, —CO$_2$(C$_1$-C$_6$alkyl), —NH$_2$, —C(=O)NH(R$^{13}$), —C(=O)N(R$^{13}$)$_2$, —OC(=O)NH(R$^{13}$), —OC(=O)N(R$^{13}$)$_2$, —N(C$_1$-C$_4$alkyl)C(=O)N(R$^{13}$)$_2$, —NHC(=O)N(R$^{13}$)$_2$, —NHC(=O)NH(R$^{13}$), —N(C$_1$-C$_4$alkyl)C(=O)R$^{12}$, —NHC(=O)R$^{12}$, —NH—C$_1$-C$_4$alkyl-C(=O)R$^{12}$, —N(C$_1$-C$_4$alkyl)C(=O)OR$^{12}$, —NHC(=O)OR$^{12}$, C$_1$-C$_6$alkyl, C$_1$-C$_6$fluoroalkyl, C$_1$-C$_6$fluoroalkoxy, C$_1$-C$_6$heteroalkyl, a substituted or unsubstituted C$_2$-C$_{10}$heterocycloalkyl, a substituted or unsubstituted phenyl, or a substituted or unsubstituted monocyclic or bicyclic heteroaryl containing 0-3 heteroatoms selected from N, O or S;

$R^{11}$ is $C_1$-$C_6$alkyl, $C_1$-$C_6$haloalkyl, $C_1$-$C_6$heteroalkyl, a substituted or unsubstituted phenyl, a substituted or unsubstituted monocyclic or bicyclic heteroaryl containing 0-3 heteroatoms selected from N, O or S, a substituted or unsubstituted —$C_1$-$C_4$alkyl-phenyl, —$C_1$-$C_6$alkylene-N($R^{17}$)$_2$, —$C_1$-$C_6$alkylene-C(=O)O—$R^{17}$, or —$C_1$-$C_6$alkylene-C(=O)N($R^{17}$)$_2$; $R^{17}$ is H, or $C_1$-$C_6$alkyl;

$R^{12}$ is $C_1$-$C_6$alkyl, $C_1$-$C_6$heteroalkyl, $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted phenyl, a substituted or unsubstituted monocyclic heteroaryl containing 0-3 heteroatoms selected from N, O or S, a substituted or unsubstituted —$C_1$-$C_4$alkyl-$C_3$-$C_{10}$cycloalkyl, a substituted or unsubstituted —$C_1$-$C_4$alkyl-phenyl, or a substituted or unsubstituted —$C_1$-$C_4$alkyl-(monocyclic heteroaryl containing 0 to 3 heteroatoms selected from N, O or S);

each $R^{13}$ is independently selected from H, $C_1$-$C_6$alkyl, $C_1$-$C_6$heteroalkyl, $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted phenyl, a substituted or unsubstituted monocyclic heteroaryl containing 0-3 heteroatoms selected from N, O or S, a substituted or unsubstituted —$C_1$-$C_4$alkyl-$C_3$-$C_{10}$cycloalkyl, a substituted or unsubstituted —$C_1$-$C_4$alkyl-$C_2$-$C_{10}$heterocycloalkyl, a substituted or unsubstituted —$C_1$-$C_4$alkyl-phenyl, and a substituted or unsubstituted —$C_1$-$C_4$alkyl-(monocyclic heteroaryl containing 0 to 3 heteroatoms selected from N, O or S); or two $R^{13}$ groups attached to the same N atom are taken together with the N atom to which they are attached to form a substituted or unsubstituted $C_2$-$C_{10}$heterocycloalkyl; and Y is —S—, —S(=O)—, or —S(=O)$_2$—.

13. The ophthalmic pharmaceutical composition of claim 12, wherein:
$R^2$ is H;
$R^3$ is H;
$R^4$ is H, halogen, —CN, $C_1$-$C_4$alkyl, $C_1$-$C_4$fluoroalkyl, $C_1$-$C_4$fluoroalkoxy, $C_1$-$C_4$alkoxy, or $C_1$-$C_4$heteroalkyl;
$R^6$ is —N($C_1$-$C_4$alkyl)S(=O)$_2R^{12}$, —NHS(=O)$_2R^{12}$, —S(=O)$_2$N($R^{13}$)$_2$, —NH$_2$, —C(=O)NH($R^{13}$), —C(=O)N($R^{13}$)$_2$, —N($C_1$-$C_4$alkyl)C(=O)N($R^{13}$)$_2$, —NHC(=O)N($R^{13}$)$_2$, —NHC(=O)NH($R^{13}$), —N($C_1$-$C_4$alkyl)C(=O)$R^{12}$, —NHC(=O)$R^{12}$, —N($C_1$-$C_4$alkyl)C(=O)O$R^{12}$, or —NHC(=O)O$R^{12}$;
$R^{11}$ is $C_1$-$C_6$alkyl, $C_1$-$C_6$haloalkyl, $C_1$-$C_6$heteroalkyl, a substituted or unsubstituted phenyl, a substituted or unsubstituted 5-membered heteroaryl, a substituted or unsubstituted 6-membered heteroaryl, or —$C_1$-$C_4$alkyl-(substituted or unsubstituted phenyl);
$R^{12}$ is $C_1$-$C_6$alkyl, $C_1$-$C_6$heteroalkyl, $C_1$-$C_6$fluoroalkyl, $C_3$-$C_6$cycloalkyl, a substituted or unsubstituted phenyl, a substituted or unsubstituted 6-membered heteroaryl, or —$C_1$-$C_4$alkyl-(substituted or unsubstituted phenyl); and
$R^{13}$ is H or $C_1$-$C_4$alkyl.

14. The ophthalmic pharmaceutical composition of claim 13, wherein:
$R^6$ is —N($C_1$-$C_4$alkyl)C(=O)$R^{12}$ or —NHC(=O)$R^{12}$;
$R^{11}$ is $C_1$-$C_6$alkyl, $C_1$-$C_6$haloalkyl, a substituted or unsubstituted phenyl, or —$C_1$-$C_4$alkyl-(substituted or unsubstituted phenyl); and
$R^{12}$ is $C_1$-$C_6$alkyl, $C_3$-$C_6$cycloalkyl, or a substituted or unsubstituted phenyl.

15. The ophthalmic pharmaceutical composition of claim 14, wherein:
$R^4$ is F, Cl, —OCH$_3$, —CF$_3$, or —OCF$_3$;
$R^{11}$ is —C(CH$_3$)$_3$; and
$R^{12}$ is —C(CH$_3$)$_3$.

16. The ophthalmic pharmaceutical composition of claim 12, wherein the DP$_2$ receptor antagonist compound is {3-[2-tert-butylsulfanylmethyl-4-(2,2-dimethyl-propionylamino)-phenoxy]-4-methoxy-phenyl}-acetic acid, or a pharmaceutically acceptable salt thereof.

17. The ophthalmic pharmaceutical composition of claim 12, wherein the ophthalmic pharmaceutical composition further comprises a tonicity adjusting component.

18. The ophthalmic pharmaceutical composition of claim 17, wherein the tonicity adjusting component is sodium borate, boric acid, sodium chloride, potassium chloride, mannitol, dextrose, glycerin, propylene glycol or mixtures thereof.

19. The ophthalmic pharmaceutical composition of claim 12, wherein the concentration of the DP$_2$ receptor antagonist compound in the ophthalmic pharmaceutical composition is about 0.1% to about 10% by weight of the ophthalmic pharmaceutical composition.

20. The ophthalmic pharmaceutical composition of claim 12, wherein the ophthalmic pharmaceutical composition is used for treating an ophthalmic disease or condition selected from an immune disease or condition; a proliferative disease or condition; contact with an allergen and/or an irritant; a mast cell mediated disease or condition; a Th2 lymphocyte mediated disease or condition; an infection or combinations thereof.

21. The ophthalmic pharmaceutical composition of claim 12, wherein the ophthalmic pharmaceutical composition is used for treating age-related macular degeneration, allergic conjunctivitis, eosinophilic keratitis, anterior segment scarring, blepharitis, blepharoconjunctivitis, a bullous disorder, cicatricial pemphigoid, conjunctival melanoma, conjunctivitis, contact lens-associated giant papillary conjunctivitis, diabetic retinopathy, dry eye, episcleritis, glaucoma, gliosis, granuloma annulare, Graves' ophthalmopathy, intraocular melanoma, keratitis, keratoconjunctivitis, pain, pinguecula, post-surgical pain, proliferative vitreoretinopathy, pterygia, scarring, scleritis, Sjögren's syndrome, uveitis, vernal keratoconjunctivitis or combinations thereof.

22. The method of claim 1, wherein the DP$_2$ receptor antagonist compound is {3-[2-tert-butylsulfanylmethyl-4-(2,2-dimethyl-propionylamino)-phenoxy]-4-methoxy-phenyl}-acetic acid, or a pharmaceutically acceptable salt thereof.

* * * * *